United States Patent [19]

Edwards et al.

[11] Patent Number: 5,098,930
[45] Date of Patent: Mar. 24, 1992

[54] HETEROCYCLIC DERIVATIVES

[75] Inventors: Philip N. Edwards, Bramhall, England; Jean-Marc M. M. Girodeau, Rilly la Montagne, France

[73] Assignees: Imperial Chemical Industries PLC, London, England; ICI Pharma, Reims Cedex, France

[21] Appl. No.: 455,173

[22] Filed: Dec. 22, 1989

[30] Foreign Application Priority Data

Dec. 23, 1988 [EP] European Pat. Off. ............ 88403313
May 31, 1989 [EP] European Pat. Off. ............ 89401491

[51] Int. Cl.$^5$ .................... A61K 31/35; C07D 309/10; C07D 309/12
[52] U.S. Cl. .................... 514/459; 514/460; 549/416; 549/417; 549/420; 549/423
[58] Field of Search ............... 549/416, 417, 420, 423; 514/459, 460

[56] References Cited

U.S. PATENT DOCUMENTS

| 3,661,917 | 5/1972 | Kalser et al. | |
| 3,743,737 | 7/1973 | Kalser et al. | |
| 4,918,081 | 4/1990 | Huang | 514/311 |
| 4,920,130 | 4/1990 | Huang | 514/314 |
| 4,920,131 | 4/1990 | Huang | 514/311 |
| 4,920,132 | 4/1990 | Huang | 514/314 |
| 4,920,133 | 4/1990 | Huang | 514/314 |

FOREIGN PATENT DOCUMENTS

| 0110405 | 6/1984 | European Pat. Off. . |
| 0181568 | 5/1986 | European Pat. Off. . |
| 0190722 | 8/1986 | European Pat. Off. . |
| 0200101 | 12/1986 | European Pat. Off. . |
| 0271287 | 6/1988 | European Pat. Off. . |
| 0349062 | 1/1990 | European Pat. Off. . |

Primary Examiner—Nicky Chan
Attorney, Agent, or Firm—Cushman, Darby & Cushman

[57] ABSTRACT

The invention concerns a heterocyclic derivative of the formula I,

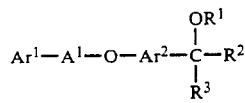

wherein
Ar$^1$ is optionally substituted phenyl or naphthyl;
A$^1$ is (1-6C)alkylene, (3-6C)alkenylene, (3-6C)alkynylene or cyclo-(3-6C)alkylene;
Ar$^2$ is optionally substituted phenylene, or a 6 membered heterocyclene moiety containing up to three nitrogen atoms;
R$^1$ is hydrogen, (1-6C)alkyl, (3-6C)alkenyl, (3-6C)alkynyl, cyano-(1-4C)alkyl or (2-4C)alkanoyl, or optionally substituted benzoyl; and
R$^2$ and R$^3$ together form a group of the formula -A$^2$-X-A$^3$- wherein each of A$^2$ and A$^3$ is (1-4C)alkylene and X is oxy, thio, sulphinyl, sulphonyl or imino;
or a pharmaceutically-acceptable salt thereof.

The compounds of the invention are inhibitors of the enzyme 5-lipoxygenase.

9 Claims, No Drawings

HETEROCYCLIC DERIVATIVES

This invention concerns novel heterocyclic derivatives and more particularly novel heterocyclic derivatives which are inhibitors of the enzyme 5-lipoxygenase (hereinafter referred to as 5-LO). The invention also concerns processes for the manufacture of said derivatives and novel pharmaceutical compositions containing said derivatives. Also included in the invention is the use of said derivatives in the treatment of various inflammatory and/or allergic diseases in which the direct or indirect products of 5-LO catalysed oxidation of arachidonic acid are involved, and the production of new medicaments for such use.

As stated above the heterocyclic derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100-103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain heterocyclic derivatives are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a heterocyclic derivative of the formula I (set out hereinafter)

wherein $Ar^1$ is phenyl or naphthyl which may optionally bear one or more substituents selected from amino, halogeno, hydroxy, carboxy, cyano, (1–6C)alkyl, (2–6C)alkenyl, (2–6C)alkynyl, (1–4C)alkoxy, (1–4C)alkylthio, (1–4C)alkysulphinyl, (1–4C)alkylsulphonyl, (1–4C)alkylamino, di-[(1–4C)alkyl]amino, (1–4C)alkoxycarbonyl, (2–4C)alkanoyl, (2–4C)alkanoylamino, hydroxy-(1–4C)alkyl, fluoro-(1–4C)alkyl, amino-(1–4C)alkyl, cyano-(1–4C)alkyl and cyano-(1–4C)alkoxy; wherein $A^1$ is (1–6C)alkylene, (3–6C)alkenylene, (3–6C)alkynylene or cyclo(3–6C)alkylene;

wherein $Ar^2$ is phenylene which may optionally bear one or two substituents selected from halogeno, hydroxy, amino, nitro, cyano, carbamoyl, ureido, (1–4C)alkyl, (3–4C)alkenyloxy, (1–4C)alkoxy, (1–4C)alkylthio, (1–4C)alkylsulphinyl, (1–4C)alkylsulphonyl, (1–4C)alkylamino, di-[(1–4C)alkyl]amino, fluoro-(1–4C)alkyl, (1–4C)alkoxycarbonyl, N-[(1–4C)alkyl]carbamoyl, N,N-di-[(1–4C)alkyl]carbamoyl, (2–4C)alkanoylamino, cyano-(1–4C)alkoxy, carbamoyl-(1–4C)alkoxy, (1–4C)alkoxycarbonyl-(1–4C)alkoxy, hydroxy-(2–4C)alkylamino, cyano-(1–4C)alkylamino, carboxy-(1–4C)alkylamino and (1–4C)alkoxycarbonyl-(1–4C)alkylamino; or $Ar^2$ is a 6-membered heterocyclene moiety containing up to three nitrogen atoms; wherein $R^1$ is hydrogen, (1–6C)alkyl, (3–6C)alkenyl, (3–6C)alkynyl, cyano-(1–4C)alkyl or (2–4C)alkanoyl, or $R^1$ is benzoyl which may optionally bear a substituent selected from halogeno, (1–4C)alkyl and (1–4C)alkoxy; and wherein $R^2$ and $R^3$ together form a group of the formula $-A^2-X-A^3-$ which, together with the carbon atom to which $A^2$ and $A^3$ are attached, defines a ring having 4 to 7 ring atoms, wherein $A^2$ and $A^3$, which may be the same or different, each is (1–4C)alkylene and X is oxy, thio, sulphinyl, sulphonyl or imino, and which ring may bear one, two or three substituents, which may be the same or different, selected from hydroxy, (1–4C)alkyl, (1–4C)alkoxy, (3–4C)alkenyloxy and (3–4C)alkynyloxy; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for a halogeno substituent which may be present on $Ar^1$, $Ar^2$ or $R^1$ is, for example, fluoro, chloro, bromo or iodo.

A suitable value for a (1–6C)alkyl substituent which may be present on $Ar^1$ is, for example, methyl, ethyl, propyl, isopropyl, butyl, isobutyl, sec-butyl, tert-butyl, pentyl or hexyl.

A suitable value for a (1–4C)alkyl substituent which may be present on $Ar^2$ or $R^1$ is, for example, methyl, ethyl, propyl, isopropyl, butyl, isobutyl or sec-butyl.

A suitable value for a (2–6C)alkenyl substituent on $Ar^1$ is, for example, vinyl, allyl, 2-butenyl or 3-butenyl.

A suitable value for a (2–6C)alkynyl substituent on $Ar^1$ is, for example, ethynyl, 1-propynyl, 2-propynyl, 1-butynyl or 2-butynyl.

A suitable value for a (1–4C)alkoxy substituent which may be present on $Ar^1$, $Ar^2$ or $R^1$ is, for example, methoxy, ethoxy, propoxy, isopropoxy or butoxy.

A suitable value for a (2–4C)alkanoyl substituent which may be present on $Ar^1$ or for $R^1$ when it is (2–4C)alkanoyl is, for example acetyl, propionyl or butyryl.

Suitable values for substituents which may be present on $Ar^1$ or $Ar^2$ include, for example:

for (1-4C)alkylthio: methylthio, ethylthio, propylthio, isopropylthio and butylthio;

for (1-4C)alkylsulphinyl: methylsulphinyl, ethylsulphinyl, propylsulphinyl, isopropylsulphinyl and butylsulphinyl;

for (1-4C)alkylsulphonyl: methysulphonyl, ethylsulphonyl, propylsulphonyl, isopropylsulphonyl and butylsulphonyl;

for (1-4C)alkylamino: methylamino, ethylamino propylamino and butylamino;

for di-[(1-4C)alkyl]amino: dimethylamino, diethylamino and dipropylamino;

for (1-4C)alkoxycarbonyl: methoxycarbonyl, ethoxycarbonyl and tert-butoxycarbonyl;

for fluoro-(1-4C)alkyl: fluoromethyl, difluoromethyl, trifluoromethyl, 2-fluoroethyl, 2,2,2-trifluoroethyl and pentafluoroethyl;

for cyano-(1-4C)alkoxy: cyanomethoxy, 2-cyanoethoxy and 3-cyanopropoxy;

for (2-4C)alkanoylamino: acetamido, propionamido and butyramido.

A suitable value for a substituent which may be present on $Ar^1$ when it is hydroxy-(1-4C)alkyl is, for example, hydroxymethyl, 1-hydroxyethyl, 2-hydroxyethyl, 1-hydroxypropyl, 2-hydroxypropyl or 3-hydroxypropyl; when it is cyano-(1-4C)alkyl is, for example, cyanomethyl, 1-cyanoethyl, 2-cyanoethyl, 3-cyanopropyl or 2-cyanoprop-2-yl; and when it is amino-(1-4C)alkyl is, for example, aminomethyl, 2-aminoethyl or 3-aminopropyl.

A suitable value for the number of substituents which may be present on $Ar^1$ is, for example, one, two or three.

A suitable value for $A^1$ when it is (1-6C)alkylene is, for example, methylene, ethylene, ethylidene, trimethylene, propylidene, tetramethylene or pentamethylene; when it is (3-6C)alkenylene is, for example, 1-propenylene, 2-methylprop-1-enylene, 3-methylprop-1-enylene, 1-butenylene or 2-butenylene; and when it is (3-6C)alkynylene is, for example, 1-propynylene, 3-methylprop-1-enylene, 1-butynylene or 2-butynylene.

A suitable value for $A^1$ when it is cyclo(3-6C)alkylene is, for example, cyclopropylidene, 1,2-cyclopropylene, cyclopentylidene, 1,2-cyclopentylene, cyclohexylidene or 1,4-cyclohexylene.

A suitable value for $Ar^2$ when it is phenylene is, for example, 1,3-phenylene or 1,4-phenylene.

A suitable value for $Ar^2$ when it is a 6-membered heterocyclene moiety containing up to three nitrogen atoms is, for example, pyridylene, pyrimidinylene, pyridazinylene, pyrazinylene or 1,3,5-triazinylene. Conveniently $Ar^2$ when it is a 6-membered heterocyclene moiety containing up to three nitrogen atoms is, for example, 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene.

Suitable values for substituents which may be present on $Ar^2$ include, for example:

for (3-4C)alkenyloxy: allyloxy, methylallyoxy, but-2-enyloxy and but-3-enyloxy;

for N-[(1-4C)alkyl]carbamoyl: N-methylcarbamoyl, N-ethyl-carbamoyl and N-propylcarbamoyl;

for N,N-di-[(1-4C)alkyl]-carbamoyl: N,N-dimethylcarbamoyl and N,N-diethylcarbamoyl;

for carbamoyl-(1-4C)alkoxy: carbamoylmethoxy, 2-carbamoyl ethoxy and 3-carbamoyl propoxy;

for (1-4C)alkoxycarbonyl-(1-4C)-alkoxy: methoxycarbonylmethoxy, 2-methoxycarbonylethoxy, ethoxycarbonylmethoxy and 2-ethoxycarbonylethoxy.

for hydroxy-(2-4C)alkylamino: 2-hydroxyethylamino, 3-hydroxypropylamino and 4-hydroxyalkylamino;

for cyano-(1-4C)alkylamino: cyanomethylamino, 2-cyanoethylamino and 3-cyanopropylamino;

for carboxy-(1-4C)alkylamino: carboxymethylamino, 2-carboxyethylamino and 3-carboxypropylamino;

for (1-4C)alkoxycarbonyl-(1-4C)alkylamino: methoxycarbonylmethylamino, ethoxycarbonylmethylamino, 2-methoxycarbonylethylamino and 2-ethoxycarbonylethylamino.

A suitable value for $R^1$ when it is (1-6C)alkyl is, for example, methyl, ethyl, propyl, butyl, pentyl or hexyl.

A suitable value for $R^1$ when it is (3-6C)alkenyl is, for example, allyl, 2-butenyl or 3-butenyl; and when it is (3-6C)alkynyl is, for example, 2-propynyl or 2-butynyl.

A suitable value for $R^1$ when it is cyano-(1-4C)alkyl is, for example, cyanomethyl, 2-cyanoethyl or 3-cyanopropyl.

When $R^2$ and $R^3$ together form a group of the formula $-A^2-X-A^3-$ which, together with the carbon atom to which $A^2$ and $A^3$ are attached, defines a ring having 4 to 7 ring atoms then a a suitable value for $A^2$ or $A^3$, which may be the same or different, when each is (1-4C)alkylene is, for example, methylene, ethylene, trimethylene or tetramethylene.

Suitable values for the one, two or three substituents which may be present on said 4- to 7-membered ring included for example:

for (1-4C)alkyl: methyl, ethyl, propyl, isopropyl and butyl;

for (1-4C)alkoxy: methoxy, ethoxy, propoxy, isopropoxy and butoxy;

for (3-4C)alkenyloxy: allyloxy, methylallyloxy and but-2-enyloxy;

for (3-4C)alkynyloxy: 2-propynyloxy and 2-butynyloxy.

When $R^2$ and $R^3$ together form a group of the formula $-A^2-X-A^3-$ which, together with the carbon atom to which $A^2$ and $A^3$ are attached, defines a ring having 4 to 7 ring atoms, and when said ring bears one, two or three (1-4C)alkyl substituents, then suitable values for the (1-4C)alkyl-substituted $A^2$ and $A^3$ groups include, for example, ethylidene, propylidene, isopropylidene, propylene, 2-methyltrimethylene, but-1,2-diyl, 2-methylprop-1,2-diyl, pent-1,2-diyl and hex-1,2-diyl.

A suitable pharmaceutically-acceptable salt of a heterocyclic derivative of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a heterocyclic derivative of the invention which is sufficiently acidic (for example a heterocyclic derivative of the invention which contains a carboxy group) is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

According to a further aspect of the invention there is provided a heterocyclic derivative of the formula I wherein $Ar^1$ is phenyl or naphthyl which may optionally bear one or more substituents selected from halogeno, hydroxy, carboxy, cyano, (1-4C)alkyl, (2-4C)alkenyl, (2-4C)alkynyl, (1-4C)alkoxy, (1-4C)alkylthio, (1-4C)alkysulphinyl, (1-4C)alkylsulphonyl, (1-4C)alkylamino, di-[(1-4C)alkyl]amino, (1-4C)alkoxycarbonyl, (2-4C)alkanoyl, hydroxy-(1-4C)alkyl and fluoro-(1-4C)alkyl;

wherein $A^1$ is (1-6C)alkylene, (3-6C)alkenylene, (3-6C)alkenylene or cyclo(3-6C)alkylene;

wherein $Ar^2$ is phenylene which may optionally bear one or two substituents selected from halogeno, hydroxy, amino, nitro, cyano, carbamoyl, (1-4C)alkyl, (3-4C)alkenyl, (1-4C)alkoxy, (1-4C)alkylthio, (1-4C)alkylsulphinyl, (1-4C)alkysulphonyl, (1-4C)alkylamino, di-[(1-4C)alkyl]amino, fluoro-(1-4C)alkyl, (1-4C)alkoxycarbonyl, N-[(1-4C)alkyl]carbamoyl, N,N-di-[(1-4C)alkyl]carbamoyl, (2-4C)alkanoylamino, cyano-(1-4C)alkoxy, carbamoyl-(1-4C)alkoxy and (1-4C)alkoxycarbonyl-(1-4C)alkoxy; or $Ar^2$ is a 6-membered heterocyclene moiety containing up to three nitrogen atoms;

wherein $R^1$ is hydrogen, (1-6C)alkyl, (3-6C)alkenyl, (3-6C)alkynyl, cyano-(1-4C)alkyl or (2-4C)alkanoyl, or $R^1$ is benzoyl which may optionally bear a substituent selected from halogeno, (1-4C)alkyl and (1-4C)alkoxy; and wherein $R^2$ and $R^3$ together form a group of the formula $-A^2-X-A^3-$ which, together with the carbon atom to which $A^2$ and $A^3$ are attached, defines a ring having 5 to 7 ring atoms, wherein $A^2$ and $A^3$, which may be the same or different, each is (1-4C)alkylene and X is oxy, thio, sulphinyl, sulphonyl or imino; or a pharmaceutically-acceptable salt thereof.

When, as defined immediately above, $R^2$ and $R^3$ together form a group of the formula $-A^2-X-A^3-$ which, together with the carbon atom to which $A^2$ and $A^3$ are attached, defines a ring having 5 to 7 ring atoms then a suitable value for $A^2$ or $A^3$, which may be the same or different, when each is (1-4C)alkylene is, for example, methylene, ethylene, ethylidene, trimethylene, propylidene, isopropylidene, propylene, 2-methyltrimethylene, tetramethylene, but-1,2-diyl or but-1,3-diyl.

Particular novel compounds of the invention are, for example, heterocyclic derivatives of the formula I wherein:

(a) $Ar^1$ is phenyl, naphth-1-yl or naphth-2-yl which may optionally bear one, two or three substituents selected from amino, fluoro, chloro, bromo, cyano, methyl, ethyl, propyl, isopropyl, butyl, tert-butyl, methoxy, methylthio, methylsulphinyl, methylsulphonyl, methoxycarbonyl, acetamido, difluoromethyl, trifluoromethyl, aminomethyl, cyanomethyl, 1-cyanoethyl, 2-cyanoprop-2-yl, cyanomethoxy and 2-cyanoethoxy; and $A^1$, $Ar^2$, $R^1$, $R^2$ and $R^3$ have any of the meanings defined hereinbefore;

(b) $Ar^1$ is phenyl, naphth-1-yl or naphth-2-yl which may optionally bear one, two or three substituents selected from fluoro, chloro, bromo, iodo, cyano, methyl, methoxy, methylthio, methylsulphinyl, methylsulphonyl, methoxycarbonyl, difluoromethyl and trifluoromethyl; and $A^1$, $Ar^2$, $R^1$, $R^2$ and $R^3$ have any of the meanings defined hereinbefore;

(c) $A^1$ is methylene, ethylene, trimethylene, 1-propenylene, 2-methylprop-1-enylene or 1-propynylene and $Ar^1$, $Ar^2$, $R^1$, $R^2$ and $R^3$ have any of the meanings defined hereinbefore;

(d) $Ar^2$ is 1,3-phenylene or 1,4-phenylene which may optionally bear one substituent selected from fluoro, chloro, bromo, hydroxy, amino, nitro, cyano, carbamoyl, ureido, methyl, methoxy, allyloxy, methylthio, methylsulphinyl, methylsulphonyl, methylamino, dimethylamino, trifluoromethyl, acetamido, cyanomethoxy, carbamoylmethoxy, 2-hydroxyethylamino, cyanomethylamino, carboxymethylamino, methoxycarbonylmethylamino and ethoxycarbonylmethylamino; and $Ar^1$, $A^1$, X, $R^1$, $R^2$ and $R^3$ have any of the meanings defined hereinbefore;

(e) $Ar^2$ is 1,3-phenylene or 1,4-phenylene which may optionally bear one substituent selected from fluoro, chloro, bromo, hydroxy, amino, nitro, methyl, methoxy, allyloxy, methylthio, methylsulphinyl, methylsulphonyl, methylamino, dimethylamino, trifluoromethyl, acetamido, cyanomethoxy and carbamoylmethoxy and $Ar^1$, $A^1$, X, $R^1$, $R^2$ and $R^3$ have any of the meanings defined hereinbefore;

(f) $Ar^2$ is 1,3-phenylene or 1,4-phenylene which may optionally bear one substituent selected from chloro, bromo, hydroxy, amino, nitro, methyl, methoxy, allyloxy, methylthio, methylsulphinyl, methylsulphonyl, methylamino, dimethylamino, trifluoromethyl, acetamido, cyanomethoxy and carbamoylmethoxy and $Ar^1$, $A^1$, X, $R^1$, $R^2$ and $R^3$ have any of the meanings defined hereinbefore;

(g) $Ar^2$ is 3,5-pyridylene or 3,5-pyridazinylene; and $Ar^1$, $A^1$, $R^1$, $R^2$ and $R^3$ have any of the meanings defined hereinbefore;

(h) $Ar^2$ is 2,4-, 2,5-, 3,5- or 2,6-pyridylene or 4,6-pyrimidinylene; and $Ar^1$, $A^1$, $R^1$, $R^2$ and $R^3$ have any of the meanings defined hereinbefore;

(i) $R^1$ is hydrogen, methyl, ethyl, propyl, allyl, 2-propynyl or cyanomethyl; and $Ar^1$, $A^1$, $Ar^2$, $R^2$ and $R^3$ have any of the meanings defined hereinbefore;

(j) $R^1$ is hydrogen, methyl, ethyl, allyl, 2-propynyl or cyanomethyl; and $Ar^1$, $A^1$, $Ar^2$, $R^2$ and $R^3$ have any of the meanings defined hereinbefore;

(k) $R^2$ and $R^3$ together form a group of the formula $-A^2-X-A^3-$ which, together with the carbon atom to which $A^2$ and $A^3$ are attached, defines a ring having 4 to 7 ring atoms, wherein $A^2$ and $A^3$, which may be the same or different, each is methylene, ethylene, trimethylene or tetramethylene and X is oxy, thio, sulphinyl or sulphonyl, and which ring may bear one or two substituents, which may be the same or different, selected from hydroxy, methyl, ethyl, propyl, isopropyl, methoxy, ethoxy, allyloxy and 2-propynyloxy; and $Ar^1$, $A^1$, $Ar^2$ and $R^1$ have any of the meanings defined hereinbefore;

(l) $R^2$ and $R^3$ together form a group of the formula $-A^2-X-A^3-$ which, together with the carbon atom to which $A^2$ and $A^3$ are attached, defines a ring having 4 to 7 ring atoms, and said ring bears one or two (1-4C)alkyl substituents such that particular values for the (1-4C)alkyl substituted $A^2$ and $A^3$ groups, include, for example, ethylidene, isopropylidene, propylene, but-1,2-diyl, 2-methylprop-1,2-diyl and pent-1,2-diyl; and $Ar^1$, $A^1$, $Ar^2$ and $R^1$ have any of the meanings defined hereinbefore;

(m) $R^2$ and $R^3$ together form a group of the formula $-A^2-X-A^3-$ which, together with the carbon atom to which $A^2$ and $A^3$ are attached, defines a ring having 5 to 7 ring atoms, wherein $A^2$ and $A^3$, which may be the same or different, each is methylene, ethylene, ethylidene, trimethylene, propylene or tetramethylene and X is oxy, thio, sulphinyl or sulphonyl; and $Ar^1$, $A^1$, $Ar^2$ and $R^1$ have any of the meanings defined hereinbefore; or (n) $R^2$ and $R^3$ together form a group of the formula —$A^2$-X-$A^3$- which, together with the carbon atom to which $A^2$ and $A^3$ are attached, defines a ring having 5 to 7 ring atoms, wherein $A^2$ and $A^3$, which may be the same or different, each is methylene, ethylene, ethylidene, trimethylene or tetramethylene and X is oxy, thio, sulphinyl or sulphonyl; and $Ar^1$, $A^1$, $Ar^2$ and $R^1$ have any of the meanings defined hereinbefore;

or a pharmaceutically-acceptable salt thereof.

A preferred compound of the invention comprises a heterocyclic derivative of the formula I wherein $Ar^1$ is phenyl or naphth-2-yl which may optionally bear one or two substituents selected from amino, fluoro, chloro, bromo, cyano, methyl, ethyl, propyl, isopropyl, butyl, tert-butyl, methoxy, methylthio, methylsulphinyl, methylsulphonyl, difluoromethyl, trifluoromethyl, cyanomethyl, 1-cyanoethyl, 2-cyanoprop-2-yl, cyanomethoxy and 2-cyanoethoxy;

$A^1$ is methylene, 1-propenylene or 1-propynylene;

$Ar^2$ is 1,3-phenylene or 1,4-phenylene which may optionally bear one substituent selected from fluoro, hydroxy, amino, nitro, ureido, methoxy, methylamino, dimethylamino, trifluoromethyl, acetamido, cyanomethoxy, 2-hydroxyethylamino, cyanomethylamino and carboxymethylamino; or $Ar^2$ is 3,5-pyridylene or 3,5-pyridazinylene;

$R^1$ is hydrogen, methyl, ethyl, allyl or 2-propynyl; and $R^2$ and $R^3$ together form a group of the formula —$A^2$-X-$A^3$- which, together with the carbon atom to which $A^2$ and $A^3$ are attached, defines a ring having 5 to 7 ring atoms, wherein $A^2$ is ethylene, $A^3$ is methylene, ethylene or trimethylene, and X is oxy or thio, and which ring may bear one or two substituents, which may be the same or different, selected from hydroxy, methyl, ethyl, propyl and methoxy; or a pharmaceutically-acceptable salt thereof.

A further preferred compound of the invention comprises a heterocyclic derivative of the formula I wherein $Ar^1$ is phenyl or naphth-2-yl which may optionally bear one or two substituents selected from fluoro, chloro, bromo, cyano, methyl, ethyl, tert-butyl, methylthio, methylsulphinyl, difluoromethyl, trifluoromethyl and cyanomethoxy;

$A^1$ is methylene or 1-propynylene;

$Ar^2$ is 1,3-phenylene which may optionally bear one substituent selected from fluoro, amino, nitro, ureido, dimethylamino, trifluoromethyl and cyanomethylamino; or $Ar^2$ is 3,5-pyridylene;

$R^1$ is methyl, ethyl or allyl; and $R^2$ and $R^3$ together form a group of the formula —$A^2$-X-$A^3$- which, together with the carbon atom to which $A^2$ and $A^3$ are attached, defines a ring having 5 to 6 ring atoms, wherein $A^2$ is ethylene, $A^3$ is methylene or ethylene and X is oxy, and which ring may bear a methyl or ethyl substituent alpha to X;

or a pharmaceutically-acceptable salt thereof.

A further preferred compound of the invention comprises a heterocyclic derivative of the formula I wherein $Ar^1$ is phenyl, naphth-1-yl or naphth-2-yl which may optionally bear one or two substituents selected from fluoro, chloro, cyano, methyl, methoxy, difluoromethyl and trifluoromethyl;

$A^1$ is methylene, 1-propenylene or 1-propynylene;

$Ar^2$ is 1,3-phenylene or 1,4-phenylene which may optionally bear one substituent selected from fluoro, hydroxy, amino, nitro, methoxy, methylamino, cyanomethoxy and trifluoromethyl; or $Ar^2$ is 3,5-pyridylene; and $R^1$ is hydrogen, methyl, allyl or cyanomethyl; and $R^2$ and $R^3$ together form a group of the formula —$A^2$-X-$A^3$- which, together with the carbon atom to which $A^2$ and $A^3$ are attached, defines a ring having 5 or 6 ring atoms, wherein $A^2$ is ethylene, $A^3$ is methylene, ethylene, ethylidene, trimethylene, propylene or tetramethylene and X is oxy or thio; or a pharmaceutically-acceptable salt thereof.

A further preferred compound of the invention comprises a heterocyclic derivative of the formula I wherein $Ar^1$ is naphth-2-yl;

$A^1$ is methylene;

$Ar^2$ is 1,3-phenylene;

$R^1$ is hydrogen or methyl; and $R^2$ and $R^3$ together form a group of the formula —$A^2$-X-$A^3$- which, together with the carbon atom to which $A^2$ and $A^3$ are attached, defines a ring having 5 or 6 ring atoms, wherein $A^2$ is ethylene, $A^3$ is methylene, ethylene or ethylidene and X is oxy or thio; or a pharmaceutically-acceptable salt thereof.

An especially preferred compound of the invention comprises a heterocyclic derivative of the formula I wherein $Ar^1$ is phenyl or naphth-2-yl; $A^1$ is methylene or 1-propynylene;

$Ar^2$ is 1,3-phenylene or 5-fluoro-1,3-phenylene;

$R^1$ is methyl; and $R^2$ and $R^3$ together form a group of the formula —$A^2$-X-$A^3$- which, together with the carbon atom to which $A^2$ and $A^3$ are attached, defines a ring having 5 or 6 ring atoms, wherein $A^2$ is ethylene, $A^3$ is ethylene, ethylidene or propylene and X is oxy; or a pharmaceutically-acceptable salt thereof.

A further especially preferred compound of the invention comprises a heterocyclic derivative of the formula I wherein $Ar^1$ is phenyl, 4-fluorophenyl, 2,4-difluorophenyl, 2-chlorophenyl, 3-chlorophenyl, 3,5-dichlorophenyl, 2,5-dimethylphenyl, 4-ethylphenyl, 4-tert-butylphenyl, 4-methylthiophenyl, 4-methylsulphinylphenyl, 2-trifluoromethylphenyl, 2-cyanomethoxyphenyl, 3-cyanomethoxyphenyl, 2-cyano-3-fluorophenyl or 2-methylthio-5-trifluoromethylphenyl;

$A^1$ is 1-propynylene;

$Ar^2$ is 1,3-phenylene, 5-fluoro-1,3-phenylene, 5-amino-1,3-phenylene, 5-nitro-1,3-phenylene, 5-ureido-1,3-phenylene, 5-dimethylamino-1,3-phenylene, 5-trifluoromethyl-1,3-phenylene, 5-acetamido-1,3-phenylene, 5-(2-hydroxyethylamino)-1,3-phenylene or 5-cyanomethylamino-1,3-phenylene; or $Ar^2$ is 3,5-pyridylene;

$R^1$ is methyl, ethyl or allyl; and $R^2$ and $R^3$ together form a group of the formula —$A^2$-X-$A^3$- which, together with the carbon atom to which $A^2$ and $A^3$ are attached, defines a ring having 6 ring atoms, wherein each of $A^2$ and $A^3$ is ethylene and X is oxy, and which ring may bear a methyl or ethyl substituent alpha to X;

or a pharmaceutically-acceptable salt thereof.

A further especially preferred compound of the invention comprises a heterocyclic derivative of the formula I wherein Ar$^1$ is naphth-2-yl, 7-fluoronaphth-2-yl, 6,7-difluoronaphth-2-yl, 7-methylnaphth-2-yl, 7-difluoromethylnaphth-2-yl, 5-bromonaphth-2-yl or 5-trifluoromethylnaphth-2-yl;

A$^1$ is methylene;

Ar$^2$ is 1,3-phenylene, 5-fluoro-1,3-phenylene or 5-trifluoromethyl-1,3-phenylene;

R$^1$ is methyl, ethyl or allyl; and

R$^2$ and R$^3$ together form a group of the formula —A$^2$-X-A$^3$- which, together with the carbon atom to which A$^2$ and A$^3$ are attached, defines a ring having 6 ring atoms, wherein each of A$^2$ and A$^3$ is ethylene and X is oxy, and which ring may bear a methyl or ethyl substituent alpha to X;

or a pharmaceutically-acceptable salt thereof.

Specific especially preferred compounds of the invention include, for example, the following heterocyclic derivatives of the formula I, or pharmaceutically-acceptable salts thereof:

4-methoxy-4-[3-(naphth-2-ylmethoxy)phenyl]tetrahydropyran, 3-methoxy-2-methyl-3-[3-(naphth-2-ylmethoxy)phenyl]tetrahydrofuran, (2RS,4SR)-4-[5-fluoro-3-(3-phenylprop-2-ynyloxy)phenyl]-4-methoxy-2-methyltetrahydropyran, 4-[5-fluoro-3-(3-phenylprop-2-ynyloxy)phenyl]-4-methoxytetrahydropyran, 4-[5-amino-3-(3-phenylprop-2-ynyloxy)phenyl]-4-methoxytetrahydropyran, 4-methoxy-4-[3-(3-phenylprop-2-ynyloxy)-5-trifluoromethylphenyl]tetrahydropyran, 4-[5-fluoro-3-(3-(4-fluorophenyl)prop-2-ynyloxy)phenyl]-4-methoxytetrahydropyran, 4-[5-(2-hydroxyethylamino)-3-(3-phenylprop-2-ynyloxy)phenyl]-4-methoxytetrahydropyran, 4-methoxy-4-[3-(3-phenylprop-2-ynyloxy)-5-ureidophenyl]tetrahydropyran, 4-[3-(3-(2-chlorophenyl)prop-2-ynyloxy)-5-fluorophenyl]-4-methoxytetrahydropyran,.

4-[5-fluoro-3-(3-(2-trifluoromethyl)phenylprop-2-ynyloxy)phenyl]-4-methoxytetrahydropyran, 4-[3-(3-(3,5-dichlorophenyl)prop-2-ynyloxy)-5-fluorophenyl]-4-methoxytetrahydropyran, 4-[3-(7-fluoronaphth-2-ylmethoxy)-5-trifluoromethylphenyl]-4-methoxytetrahydropyran, 4-allyloxy-4-[3-(7-fluoronaphth-2-ylmethoxy)-5-trifluoromethylphenyl]tetrahydropyran, 4-[3-(5-bromonaphth-2-ylmethoxy)-5-fluorophenyl]-4-methoxytetrahydropyran, (2RS,4SR)-4-[3-(7-fluoronaphth-2-ylmethoxy)phenyl]-4-methoxy-2-methyltetrahydropyran, (2RS,4SR)-4-methoxy-2-methyl-4-[3-(7-methylnaphth-2-ylmethoxy)phenyl]tetrahydropyran, (2RS,4SR)-4-[3-(7-fluoronaphth-2-ylmethoxy)-5-trifluoromethylphenyl]-4-methoxy-2-methyltetrahydropyran, (2RS,4SR)-4-ethoxy-4-[3-(7-fluronaphth-2-ylmethoxy)-5-trifluoromethylphenyl]-2-methyltetrahydropyran, (2RS,4SR)-4-[5-fluoro-3-(7-fluoronaphth-2-ylmethoxy)phenyl]-4-methoxy-2-methyltetrahydropyran, (2RS,4SR)-4-ethoxy-4-[5-fluoro-3-(7-fluoronaphth-2-ylmethoxy)phenyl]-2-methyltetrahydropyran, (2RS,4SR)-4-allyloxy-4-[3-(7-fluoronaphth-2-ylmethoxy)phenyl]-2-methyltetrahydropyran and (2RS,4SR)-4-allyloxy-2-ethyl-4-[3-(naphth-2-ylmethoxy)phenyl]tetrahydropyran.

A compound of the invention comprising a heterocyclic derivative of the formula I. or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, Ar$^1$, A$^1$, Ar$^2$, R$^1$, R$^2$ and R$^3$ have any of the meanings defined hereinbefore.

(a) The alkylation, in the presence of a suitable base, of a compound of the formula II with a compound of the formula Ar$^1$-A$^1$-Z wherein Z is a displaceable group; provided that, when there is an amino, imino, alkylamino, hydroxy or carboxy group in Ar$^1$, Ar$^2$, R$^1$, R$^2$ or R$^3$, any amino, imino, alkylamino or carboxy group is protected by a conventional protecting group and any hydroxy group may be protected by a conventional protecting group or alternatively any hydroxy group need not be protected;

whereafter any undesired protecting group in Ar$^1$, Ar$^2$, R$^1$, R$^2$ or R$^3$ is removed by conventional means.

A suitable displaceable group Z is, for example, a halogeno or sulphonyloxy group, for example a chloro, bromo, iodo, methanesulphonyloxy or toluene-p-sulphonyloxy group.

A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near ambient temperature.

A suitable protecting group for an amino, imino or alkylamino group is, for example, an acyl group for example a (1-4C)alkanoyl group (especially acetyl), a (1-4C)alkoxycarbonyl group (especially methoxycarbonyl, ethoxycarbonyl or t-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulphuric or phosphoric acid or trifluoroacetic acid and an arylmethoxycarbonyl group such as benzyloxycarbonyl group may be removed, for example, by hydrogenation over a catalyst such as palladium-on-charcoal.

A suitable protecting group for a carboxy group is, for example, an esterifying group, for example a (1-4C)alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal.

A suitable protecting group for a hydroxy group is, for example, an acyl group, for example a (1-4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula II may be obtained by standard procedures of organic chemistry. The preparation of examples of such starting materials is described within the accompanying non-limiting Examples which are provided for the purposes of illustration only. Other necessary starting materials are obtainable by analogous procedures to those described or by modifications thereto which are within the ordinary skill of an organic chemist. The starting material of the formula II may be obtained, for example, by deprotecting a protected ether derivative of the formula III wherein $R^4$ is a protecting group and $Ar^2$, $R^1$, $R^2$ and $R^3$ have the meanings defined hereinbefore.

A suitable protecting group $R^4$ is, for example, an arylmethyl group (especially benzyl), a tri-(1-4C)alkylsilyl group (especially trimethylsilyl or t-butyldimethylsilyl), an aryldi-(1-4C)-alkylsilyl group (especially dimethylphenylsilyl), a (1-4C)alkyl group (especially methyl), a (1-4C)alkoxymethyl group (especially methoxymethyl) or a tetrahydropyranyl group (especially tetrahydropyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryl dialkylsilyl group such as a t-butyldimethylsilyl or a dimethylphenylsilyl group may be removed, for example, by treatment with a suitable acid such as hydrochloric, sulphuric, phosphoric or trifluoroacetic acid or with an alkali metal or ammonium fluoride such as sodium fluoride or, preferably, tetrabutylammonium fluoride. Alternatively an alkyl group may be removed, for example, by treatment with an alkali metal (1-4C)alkylsulphide such as sodium thioethoxide or, for example, by treatment with an alkali metal diarylphosphide such as lithium diphenylphosphide. Alternatively a (1-4C)alkoxymethyl group or tetrahydropyranyl group may be removed, for example, by treatment with a suitable acid such as hydrochloric or trifluoroacetic acid.

The protecting group $R^4$ may be, for example, a tri-(1-4C)-alkylsilyl group which can be removed while the protecting group for any amino, imino, alkylamino, carboxy or hydroxy group in $Ar^2$, $R^1$, $R^2$ or $R^3$ is retained.

The protected ether derivative of the formula III, wherein $R^4$ has the meaning defined hereinbefore, may be obtained by the alkylation of the tertiary alcohol of the formula IV with an alkylating agent of the formula $R^1$-Z, wherein Z is a displaceable group as defined hereinbefore, in the presence of a suitable base as defined hereinbefore, and provided that any amino, imino, alkylamino or hydroxy group in $Ar^2$, $R^2$ or $R^3$ is protected by a conventional protecting group.

The tertiary alcohol starting material of the formula IV may be obtained by the reaction of a compound of the formula $R^4$-O-$Ar^2$-Z, wherein $R^4$ and $Ar^2$ have the meanings defined hereinbefore and Z is a halogeno group as defined hereinbefore and provided that any amino, alkylamino or hydroxy group in $Ar^2$ is protected with a conventional protecting group, with either an organometallic compound of the formula $R^6$-M, wherein $R^6$ is a (1-6C)alkyl group such as butyl and M is a metallic group, for example lithium, to give an organometallic compound of the formula $R^4$-O-$Ar^2$-M, or with a metal such as magnesium to given an organometallic compound of the formula $R^4$-O-$Ar^2$-M-Z; whereafter either of these organometallic compounds may be reacted with a ketone of the formula $R^2$-CO-$R^3$, wherein $R^2$ and $R^3$ have the meanings defined hereinbefore, and provided that any imino or hydroxy group in $R^2$ and $R^3$ is protected by a conventional protecting group.

(b) The alkylation, in the presence of a suitable base as defined hereinbefore, of a compound of the formula V with a compound of the formula $R^1$-Z, wherein $R^1$ and Z have the meanings defined hereinbefore, provided that, when there is an amino, imino, alkylamino, hydroxy or carboxy group in $Ar^1$, $Ar^2$, $R^2$ or $R^3$, any amino, imino, alkylamino, hydroxy or carboxy group is protected by a conventional protecting group; whereafter any undesired protecting group in $Ar^1$, $Ar^2$, $R^2$ or $R^3$ is removed by conventional means.

The starting materials of the formula V may be obtained by standard procedures of organic chemistry. The preparation of examples of such starting materials is described within the accompanying nonlimiting Examples which are provided for the purpose of illustration only. Other necessary starting materials are obtainable by analogous procedures to those described or by modifications thereto which are within the ordinary skill of an organic chemist. The tertiary alcohol starting material of the formula V may be obtained, for example, by the alkylation, in the presence of a suitable base, of a compound of the formula HO-$Ar^2$-Z, wherein $Ar^2$ has the meaning defined hereinbefore and Z is a halogeno group as defined hereinbefore, with a compound of the formula $Ar^1$-$A^1$-Z, wherein $Ar^1$, $A^1$ and Z have the meanings defined hereinbefore, and provided that any amino, alkylamino, carboxy or hydroxy group in $Ar^1$ or $Ar^2$ is protected by a conventional protecting group, to give a compound of the formula $Ar^1$-$A^1$-O-$Ar^2$-Z. Alternatively a compound of the formula $Ar^1$-$A^1$-O-$Ar^2$-Z may be obtained, for example, by the alkylation, in the presence of a suitable base, of a compound of the formula $Ar^1$-$A^1$-OH, wherein $Ar^1$ and $A^1$ have the meanings defined hereinbefore, with a compound of the formula Z-$Ar^2$-Z, wherein Z and $Ar^2$ have the meanings defined hereinbefore. The product so obtained may be treated either with an organometallic compound of the formula $R^6$-M, wherein $R^6$ is a (1-6C)alkyl group such as butyl and M is a metallic group, for example lithium, to give an organometallic compound of the formula $Ar^1$-$A^1$-O-$Ar^2$-M, or with a metal such as magnesium to give an organometallic compound of the formula $Ar^1$-$A^1$-O-$Ar^2$-M-Z. Either of these organometallic compounds may be reacted with a ketone of the formula $R^2$-CO-$R^3$, provided that any imino or hydroxy group in $R^2$ or $R^3$ is protected by a conventional protecting group, to give the required tertiary alcohol starting material of the formula V.

(c) For the production of those compounds of the formula I wherein $A^1$ is a (3-6C)alkynylene group, the coupling, in the presence of a suitable organometallic catalyst, of a compound of the formula $Ar^1$-Z wherein $Ar^1$ has the meaning defined hereinbefore and Z is a halogeno group such as iodo, with an ethynyl compound of the formula VI, wherein A is (1-4C)alkylene and $Ar^2$, $R^1$, $R^2$ and $R^3$ have the meanings defined hereinbefore.

A suitable organometallic catalyst is, for example, any agent known in the art for such a coupling reaction. Thus, for example, a suitable reagent is formed when, for example, bis(triphenylphosphine)palladium chloride or tetrakis(triphenylphosphine)palladium and a copper halide, for example curpous iodide, are mixed. The coupling is generally carried out in suitable inert solvent or diluent, for example acetonitrile, 1,2-dimethoxyethane, toluene or tetrahydrofuran, at a temperature in the range, for example, 10° to 80° C., conveniently at or near 50° C., and in the presence of a suitable base such as, for example, a tri-(1-4C)alkylamine such as triethylamine, or a cyclic amine such as piperidine.

The ethynyl compound of the formula VI, used as a starting material, may be obtained, for example, by the alkylation, in the presence of a suitable base, of a compound of the formula II, wherein $Ar^2$, $R^1$, $R^2$ and $R^3$ have the meanings defined hereinbefore, with an alkylating agent of the formula H—C≡C—A—Z, wherein A has the meaning defined hereinbefore and Z is a halogeno group, and provided that any amino, imino, alkylamino, carboxy or hydroxy group in $Ar^2$, $R^1$, $R^2$ or $R^3$ is protected by a conventional protecting group.

(d) For the production of those compounds of the formula I wherein $Ar^1$ or $Ar^2$ bears an alkylsulphinyl or alkylsulphonyl substituent, or wherein $R^2$ and $R^3$ together form a group of the formula —$A^2$-X-$A^3$- and X is a sulphinyl or sulphonyl group, the oxidation of a compound of the formula I wherein $Ar^1$ or $Ar^2$ bears an alkylthio substituent or wherein X is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or t-butyl methyl ether and at a temperature, for example, at or near ambient temperature, that is in the range 15 to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein $Ar^1$ or $Ar^2$ bears an alkanoylamino substituent, the acylation of a compound of the formula I wherein $Ar^1$ or $Ar^2$ bears an amino substituent.

A suitable acylating agent is, for example, any agent known in the art for the acylation of amino to acylamino; for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or t-butyl methyl ether and at a temperature, for example, at or near ambient temperature, that is in the range 15° to 35° C. A suitable base when it is required is, for example, pyridine, 4-dimethylamino-pyridine, triethylamine, ethyldiisopropylamine, N-methylmorpholine, an alkali metal carbonate, for example potassium carbonate, or an alkali metal carboxylate, for example sodium acetate.

(f) For the production of those compounds of the formula I wherein $R^1$ is alkanoyl or benzoyl optionally bearing a substituent as defined hereinbefore, the acylation of a compound of the formula I wherein $R^1$ is hydrogen. For the production of those compounds of the formula I wherein $R^1$ is alkanoyl the acylation reaction may be carried out using, for example, a suitable acylating agent as defined hereinbefore. For the production of those compounds of the formula I wherein $R^1$ is benzoyl optionally bearing a substituent the acylation may be carried out using, for example, a benzoyl halide, for example a benzoyl chloride or bromide, in the presence of a suitable base as defined hereinbefore.

(g) For the production of those compounds of the formula I wherein $Ar^1$ bears an alkenyl substituent or $A^1$ is alkenylene, the reduction of the corresponding compound wherein $Ar^1$ bears an alkynyl substituent or $A^1$ is alkynylene. In general conditions which are standard in the art for the reduction of an alkynyl or alkynylene group are used. Thus, for example, the reduction may be carried out by the hydrogenation of a solution of the alkynyl or alkynylene compound in an inert solvent or diluent in the presence of a suitable metal catalyst. A suitable inert solvent is, for example, an alcohol, for example methanol or ethanol, or an ether, for example tetrahydrofuran or t-butyl methyl ether. A suitable metal catalyst is, for example, palladium or platinum on an inert support, for example charcoal or barium sulphate.

Preferably a palladium-on-barium sulphate catalyst is used to substantially prevent over-reduction of the alkynyl or alkynylene group to an alkyl or alkylene group respectively. The reaction is generally carried out at a temperature at or near ambient temperature, that is in the range 15° to 35° C.

Alternatively the reduction may be carried out by treating a solution of the alkynyl or alkynylene compound in an inert solvent or diluent with a suitable mixture such as a 1:1 mixture of an organometallic hydride, for example a di-(1-6C)alkylaluminium hydride such as diisobutylaluminium hydride, and an alkyl metal, for example a (1-6C)alkyl lithium such as methyl lithium. A suitable inert solvent or diluent is, for example, tetrahydrofuran, diethyl ether or t-butyl methyl ether and, in general, the reaction is carried out at a temperature, for example, in the range −25° C. to ambient temperature (especially −10° to 10° C).

(h) For the production of those compounds of the formula I wherein $Ar^2$ bears an alkoxy or substituted alkoxy substituent, or an alkylamino, dialkylamino or substituted alkylamino substituent, the alkylation of a compound of the formula I wherein $Ar^2$ bears a hydroxy substituent, or an amino substituent.

A suitable alkylating agent is, for example any agent known in the art for the alkylation of hydroxy to alkoxy or substituted alkoxy, or for the alkylation of amino to alkylamino, dialkylamino or substituted alkylamino, for example an alkyl or substituted alkyl halide, for example a (1-6C)alkyl chloride, bromide or iodide or a substituted (1-4C)alkyl chloride, bromide or iodide, in the presence of a suitable base. A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

(i) For the production of those compounds of the formula I wherein $Ar^1$ or $Ar^2$ bears an amino substituent, the reduction of a compound of the formula I wherein $Ar^1$ or $Ar^2$ bears a nitro substituent.

A suitable reducing agent is, for example, any agent known in the art for the reduction of a nitro group to an amino group. Thus, for example, the reduction may be carried out by the hydrogenation of a solution of the nitro compound in an inert solvent or diluent in the presence of a suitable metal catalyst, for example finely divided platinum metal (obtained by the reduction of platinum oxide in situ). A suitable inert solvent or diluent is, for example, an alcohol, for example methanol, ethanol or isopropanol, or an ether, for example tetrahydrofuran.

A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50° to 150° C., conveniently at or near 70° C.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae II, III, IV and V and these are provided as a further feature of the invention.

As stated previously, the heterocyclic derivatives of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512–11519). This test provides a measure of the intrinsic inhibitory properties against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, *Brit. J. Pharmacol.* 1985, 84, 34P) which involves the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319–2322) and conventional radioimmunoassay sistems to meassur $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431–438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a β-adrenergic blocking agent (propranolol) and a cyclooxygenase inhibitor (indometacin), using the procedure of W. H. Anderson et alia (*British J Pharmacology*, 1983, 78(1), 67–574). This test provides a further in vivo test for detecting 5-LO inhibitors.

Although the pharmacological properties of the compounds of the formula I vary with structural changes as expected, in general compounds of the formula I possess 5-LO inhibitory effects at the following concentrations or doses in one or more of the above tests a)-f):

Test a): $IC_{50}$ in the range, for example, 0.01–30 μM;

Test b): $IC_{50}$ ($LTB_4$) in the range, for example, 0.01–40 μM $IC_{50}$ ($TxB_2$) in the range, for example, 40–200 μM;

Test c): oral $ED_{50}$ ($LTB_4$) in the range, for example, 1–200 mg/kg;

Test d): $IC_{50}$ ($LTC_4$) in the range, for example, 0.001–1 μM, $IC_{50}$ ($PGE_2$) in the range, for example, 20–1000 μM;

Test e): inhibition of inflammation in the range, for example, 0.3–100 μg intradermally;

Test f): $ED_{50}$ in the range, for example, 0.5–10 mg/kg i.v.

No overt toxicity or other untoward effects are present in tests c), e) and/or f) when compounds of the formula I are administered at several multiples of their minimum inhibitory dose or concentration.

Thus, by way of example, the compound 4-methoxy-4-[3-(naphth-2-ylmethoxy)phenyl]tetrahydropyran has an $IC_{50}$ of 0.1 μM against $LTB_4$ and of >40 μM against $TxB_2$ in test b), and an oral $ED_{50}$ of 5 mg/kg against $LTB_4$ in test c). In general those compounds of the formula I which are particularly preferred have an $IC_{50}$ of <1 μM against $LTB_4$ and >40 μM against $TxB_2$ in test b), and an oral $ED_{50}$ of <100 mg/kg against $LTB_4$ in test c).

These compounds are examples of heterocyclic derivatives of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a heterocyclic derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is a heterocyclic derivative of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocyclic derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a heterocyclic derivative of the formula I will naturally vary according to the nature and severity of the conditions, the age and sex of the animal or patient and the route of administration, according to well known principles of medicine. As mentioned above, heterocyclic derivatives of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a heterocyclic derivative of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The compounds of the formula I may also be used in combination with leukotriene antagonists such as those disclosed in European Patent Specification Nos. 179619, 199543, 220066, 227241, 242167, 290145, 337765, 337766 and 337767, which are incorporated herein by way of reference.

The invention will now be illustrated in the following non-limiting Examples in which, unless otherwise stated:

(i) evaporations were carried out by rotary evaporations in vacuo and work-up procedures were carried out after removal of residual solids by filtration;

(ii) operations were carried out at room temperature, that is in the range 18°-20° and under an atmosphere of an inert gas such as argon;

(iii) column chromatography (by the flash procedure) and medium pressure liquid chromatography (MPLC) were performed on Merck Kieselgel silica (Art. 9385) obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally full characterised and purity was assessed by thin layer chromatographic, infra-red (IR) or NMR analysis;

(vii) melting points are uncorrected and were determined using a Mettler SP62 automatic melting point apparatus; melting points for the end-products of the formula I were determined after recrystallisation from a conventional organic solvent such as ethanol, methanol, acetone, ether or hexane, alone or in admixture; and (viii) the specific rotation, $[\alpha]'$, of plane polarised light was determined using the sodium D line (5890 Angstroms), at 20° C., and generally using sample concentrations of approximately 1 g/100 ml of solvent.

EXAMPLE 1

A mixture of 4-hydroxy-4-[3-(naphth-2-ylmethoxy)-phenyl]-tetrahydropyran (1.9 g), sodium hydride (0.27 g of a 50% w/w dispersion in mineral oil), 1,4,7,10,13-pentaoxacyclopentadecane (hereinafter 15-crown-5, 0.2 g) and tetrahydrofuran (10 ml) was stirred at ambient temperature for 15 minutes. Methyl iodide (0.35 ml) was added and the mixture was stirred at ambient temperature for 15 hours. The mixture was evaporated and the residue was partitioned between diethyl ether and water. The organic layer was separated, washed with a saturated aqueous sodium chloride solution, dried (MgSO$_4$) and evaporated. The residue was purified by column chromatography using a 9:1 v/v mixture of methylene chloride and diethyl ether as eluent. There was thus obtained 4-methoxy-4-[3-(naphth-2-ylmethoxy)phenyl]tetrahydropyran (1.8 g, 94%), m.p. 66.5°-67.5° C.

The 4-hydroxy-4-[3-(naphth-2-ylmethoxy)phenyl]tetrahydropyran starting material was obtained as follows:

A Grignard reagent was prepared by heating a mixture of 3-(naphth-2-ylmethoxy)bromobenzene (3 g), magnesium powder (0.23 g) and tetrahydrofuran (12 ml) to 30° C. for 1.5 hours. The reagent was cooled to 20° C. and a solution of tetrahydropyran-4-one (0.88 ml) in tetrahydrofuran (5 ml) was added dropwise. The mixture was heated to 30° C. for 15 hours, evaporated and the residue was partitioned between ethyl acetate and water. The organic layer was separated, washed with a saturated aqueous sodium chloride solution, dried (MgSO$_4$) and evaporated. The residue was purified by column chromatography using a 7:3 v/v mixture of methylene chloride and diethyl ether as eluent. There was thus obtained 4-hydroxy-4-[3-(naphth-2-ylmethoxy)phenyl]-tetrahydropyran (2.06 g, 42%), m.p. 130°-131° C.

EXAMPLE 2

The procedure described in Example 1 was repeated except that the appropriate cyclic ether was used in place of 4-hydroxy-4-[3-(naphth-2-ylmethoxy)phenyl]-tetrahydropyran. There were thus obtained the compounds described in the following table:

TABLE IA

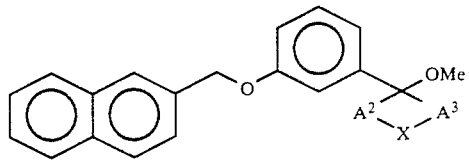

| Example 2:- Compound No. | $A^2$ | X | $A^3$ | m.p. (°C.) | Yield (%) |
|---|---|---|---|---|---|
| 1 | CH$_2$ | O | (CH$_2$)$_2$ | 89-90 | 37 |
| 2 | (CH$_2$)$_2$ | O | CH(Me) | 106-107 | 70 |
| 3 | (CH$_2$)$_2$ | S | (CH$_2$)$_2$ | 106-107 | 57 |
| 4$^a$ | CH$_2$ | O | (CH$_2$)$_4$ | oil | 58 |
| 5 | CH$_2$ | O | (CH$_2$)$_3$ | 79-80 | 47 |

NOTES a. The product displayed the following characteristic NMR signals (CDCl$_3$, & values):- 1.6-2.25(m, 6H), 3.05(s, 3H), 3.5-4.15(m, 4H), 5.23(s, 2H), 6.8-7.7(m, 7H), 7.7-7.8(m, 4H).

The appropriate cyclic ether starting materials were obtained using the procedure described in the portion of Example 1 which is concerned with the preparation of starting materials except that the appropriate aldehyde or ketone was used in place of tetrahydropyran-4-one. There were thus obtained the cyclic ether starting materials described in the following table:

TABLE IB

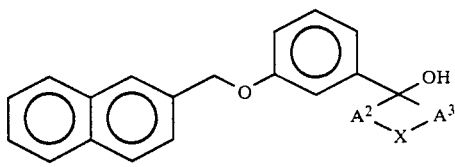

| Starting Material for Example 2:- Compound No. | A² | X | A³ | m.p. (°C.) | Yield (%) |
|---|---|---|---|---|---|
| 1a | $CH_2$ | O | $(CH_2)_2$ | 89–90 | 65 |
| 2 | $(CH_2)_2$ | O | CH(Me) | 100–101 | 30 |
| 3 | $(CH_2)_2$ | S | $(CH_2)_2$ | 140–141 | 59 |
| 4[b] | $CH_2$ | O | $(CH_2)_4$ | 115–116 | 30 |
| 5[c] | $CH_2$ | O | $(CH_2)_3$ | oil | 46 |

NOTES a. 3-Ketotetrahydrofuran, used as a starting material, was obtained by Swern oxidation of 3-hydroxytetrahydrofuran using the procedure described in J. Org. Chem., 1978, 43, 2480.

b. 3-Ketooxepane (0.17 g; 26%), used as a starting material, was obtained by hydrogenation of a solution of 2,3,4,5-tetrahydrooxepin-3-ol (0.6 g; Chem & Ind., 1985, 600) in ethanol (30 ml) in the presence of 5% palladium-on-charcoal catalyst; followed by Swern oxidation of the resulting 3-hydroxyoxepane using the procedure described in J. Org. Chem., 1978, 43, 2480.

c. 3-Ketotetrahydropyran, used as a starting material, was obtained by Swern oxidation of 3-hydroxytetrahydropyran (J. Org. Chem., 1985, 50, 1587) using the procedure described in J. Org. Chem., 1978, 43, 2480.

EXAMPLE 3

A mixture of (2RS, 4SR)-4-(3-benzyloxy-5-fluorophenyl)-4-hydroxy-2-methyltetrahydropyran (0.45 g) and dimethylformamide (5 ml) cooled in an ice bath, sodium hydride (0.068 g of a 55% w/w dispersion in mineral oil) was added and the mixture was stirred for 45 minutes. Methyl iodide (0.11 ml) was added and the mixture was stirred for 15 minutes. The ice bath was removed and the mixture was stirred at ambient temperature for 30 minutes. The mixture was poured into water (15 ml) and extracted with ethyl acetate (3×15 ml). The combined organic extracts were washed with a saturated aqueous sodium chloride solution, dried (MgSO4) and evaporated. The residue was purified by column chromatography using a 10:1 v/v mixture of toluene and ethyl acetate as eluent. There was thus obtained as an oil, (2RS, 4SR)-4-(3-benzyloxy-5-fluorophenyl)-4-methoxy-2-methyltetrahydropyran (0.33 g, 71%);

NMR Spectrum (CDCl3; δ values) 1.18 (d, 3H), 1.52 (doublet of doublets, 1H), 1.86–1.98 (m, 3H), 2.97 (s, 3H), 3.8–3.95 (m, 3H), 5.05 (s, 2H), 6.60 (doublet of triplets, 1H), 6.70 (doublet of triplets, 1H), 6.80 (t, 1H), 7.3–7.44 (m, 5H);

Mass Spectrum P m/e 330;

Elemental Analysis Found C, 72.5; H, 7.1; $C_{20}H_{23}FO_3$ requires C, 72.7; H, 7.0%.

The (2RS, 4SR)-4-(3-benzyloxy-5-fluorophenyl)-4-hydroxy-2-methyltetrahydropyran starting material was obtained as follows:

A mixture of benzyl alcohol (10 g), sodium hydride (4.44 g of a 50% w/w dispersion in meneral oil) and dimethylacetamide (180 ml) was stirred at ambient temperature for 1 hour; 1-bromo-3,5-difluorobenzene (10.65 ml) was added and the exothermic reaction mixture was stirred for 2 hours. The mixture was evaporated and the residue was partitioned between methylene chloride and water. The organic layer was separated, washed with water, dried (MgSO4) and evaporated. The residue was purified by column chromatography using a 20:1 v/v mixture of petroleum ether (b.p. 60°–80° C.) and ethyl acetate as eluent. There was thus obtained, as a liquid, benzyl 3-bromo-5-fluorophenyl ether (19.5 g, 75%).

A solution of n-butyl-lithium (6.5 ml of a 1.6 M solution in hexane) was added to a solution of a portion (2.81 g) of the benzyl ether so obtained in tetrahydrofuran (50 ml) which had been cooled to −78° C. and the mixture was stirred at this temperature for 40 minutes. A solution of 2-methyltetrahydropyran-4-one (1.14 g; J. Amer. Chem. Soc., 1982, 4666) in tetrahydrofuran (5ml) was added, the mixture was stirred at −78° C. for 30 minutes, and then allowed to warm to ambient temperature. A saturated aqueous ammonium chloride solution (30 ml) was added and the mixture was extracted with ethyl acetate (3×30 ml). The organic extracts were combined, washed with a saturated aqueous sodium chloride solution, dried (MgSO4) and evaporated. The residue, containing a mixture of diastereoisomers, was purified and the isomers were separated by colum chromatography using a 5:1 v/v mixture of toluene and ethyl acetate as eluent. There was thus obtained (2RS, 4SR)-4-(3-benzyloxy-5-fluorophenyl)-4-hydroxy-2-methyltetrahydropyran (0.74 g, 24%) as an oil, i.e. the 2-methyl and 4-hydroxy substituents are in trans relationship;

NMR Spectrum (CDCl3, δ values) 1.20 (d, 3H), 1.58 (broad s, 1H, OH), 1.52 (s, 2H), 1.99–2.14 (m, 1H), 3.86–4.02 (m, 3H), 5.05 (s, 2H), 6.60 (doublet of triplets, 1H), 6.80 (doublet of triplets, 1H), 6.90 (s, 1H), 7.28–7.48 (m, 5H, aromatic); and (2SR, 4SR)-4-(3-benzyloxy-5-fluorophenyl)-4-hydroxy-2-methyltetrahydropyran (1.52 g, 48%), m.p. 82°–83° C., i.e. the 2-methyl and 4-hydroxy substituents are in a cis relationship;

NMR Spectrum (CDCl3, δ values) 1.21 (t, 3H), 1.66 (doublet of doublets, 1H), 1.80 (broad s, 1H), 1.96 (triplet of doublets, 1H), 2.23–2.35 (m, 2H), 3.30–3.42 (m, 2H), 3.94 (doublet of quartets, 1H), 5.05 (s, 2H), 6.64 (doublet of triplets, 1H), 6.79 (doublet of triplets, 1H), 6.87 (s, 1H), 7.30–7.42 (m, 5H, aromatic).

EXAMPLE 4

The procedure described in Example 3 was repeated except that the other diasteroisomer described in the portion of Example 18 which is concerned with the preparation of starting materials, namely (2SR, 4SR)-4-(3-benzyloxy-5-fluorophenyl)-4-hydroxy-2-methyltetrahydropyran was used as a starting material. There was thus obtained (2SR, 4SR)-4-(3-benzyloxy-5-fluorophenyl)-4-methoxy-2-methyltetrahydropyran, as an oil (75%);

NMR Spectrum (CDCl3, δ values) 1.20 (d, 3H), 1.60 (doublet of doublets, 1H), 1.91 (triplet of doublets, 1H), 2.22–2.32 (m, 2H), 2.88 (s, 3H), 3.3–3.43 (m, 2H), 3.9–4.14 (m, 1H), 5.06 (s, 2H), 6.65 (doublet of triplets, 1H), 6.74 (doublet of triplets, 1H), 6.81 (t, 1H), 7.3–7.44 (m, 5H);

Mass Spectrum P m/e 330;

Elemental Analysis Found C, 72.6; H, 7.1; $C_{20}H_{23}FO_3$ requires C, 72.7; H, 7.0%.

EXAMPLE 5

A mixture of (2RS, 4SR)-4-(5-fluoro-3-hydroxyphenyl)-4-methoxy-2-methyltetrahydropyran (0.35 g), 3-phenylprop-2-ynyl bromide (0.315 g), potassium carbonate (0.3 g) and dimethylformamide (5 ml) was stirred at ambient temperature for 15 hours. The mixture was partitioned between ethyl acetate and water. The organic layer was washed with a saturated aqueous sodium chloride solution, dried (MgSO$_4$) and evaporated. The residue was purified by column chromatography using a 97.5: 2.5 v/v mixture of toluene and ethyl acetate as eluent. There was thus obtained (2RS, 4SR)-4-[5-fluoro-3-(3-phenylprop-2-ynyloxy)phenyl]-4-methoxy-2-methyltetrahydropyran (0.37 g, 72%), as an oil;

NMR Spectrum (CDCl$_3$, δ values) 1.19 (d, 3H), 1.55 (doublet of doublets, 1H), 1.87–2.02 (m, 5H), 3.0 (s, 3H), 3.8–3.95 (m, 3H), 4.92 (s, 2H), 6.64–6.78 (m, 2H), 6.88 (s, 1H), 7.24–7.98 (m, 5H);

Mass Spectrum P m/e 354;

Elemental Analysis Found, C, 72.0; H, 6.2; C$_{22}$H$_{23}$FO$_3$. 0.5 EtOAc requires C, 72.3; H, 6.8%.

The (2RS, 4SR)-4-(5-fluoro-3-hydroxyphenyl)-4-methoxy-2-methyltetrahydropyran used as a starting material was obtained as follows:

A mixture of (2RS, 4SR)-4-(3-benzyloxy-5-fluorophenyl)-4-methoxy-2-methyltetrahydropyran (1.58 g; Ex. 3), 10% palladium-on-charcoal catalyst (0.16 g) and ethanol (30 ml) was stirred under an atmosphere of hydrogen for 4 hours. The mixture was filtered and the filtrate was evaporated. There was thus obtained the required starting material (1 g, 87%), m.p. 127° C.

EXAMPLE 6

The procedure described in Example 5 was repeated except that the other diastereoisomer, namely (2SR, 4SR)-4-(5-fluoro-3-hydroxyphenyl)-4-methoxy-2-methyltetrahydropyran, was used as a starting material. There was thus obtained (2SR, 4SR)-4-[5-fluoro-3-(3-phenylprop-2-ynyloxy)phenyl]-4-methoxy-2-methyltetrahydropyran as an oil (78%);

NMR Spectrum (CDCl$_3$, δ values) 1.18 (d, 3H), 1.62 (doublet of doublets, 1H), 1.93 (triplet of doublets, 1H), 2.3 (m, 2H), 2.90 (s, 3H), 3.4 (m, 2H), 3.96 (doublet of quartets, 1H), 4.93 (s, 2H), 6.68–6.83 (m, 2H), 6.91 (s, 1H), 7.25–7.48 (m, 5H);

Mass Spectrum P m/e 354;

Elemental Analysis Found C, 72.6; H, 6.3; C$_{22}$H$_{23}$FO$_3$. 0.33 EtOAc requires C, 73.0; H, 6.7%.

The (2SR, 4SR)-4-(5-fluoro-3-hydroxyphenyl)-4-methoxy-2-methyltetrahydropyran used as a starting material was obtained using the hydrogenolysis procedure described in the portion of Example 5 which is concerned with the preparation of starting materials provided that the appropriate diastereoisomer (Ex. 4) was selected. There was thus obtained the required starting material (95%), m.p. 116° C.

EXAMPLE 7

The procedure described in Example 5 was repeated using the appropriate alkylating agent and the appropriate phenol. There was thus obtained the compounds described in the following table:

TABLE II

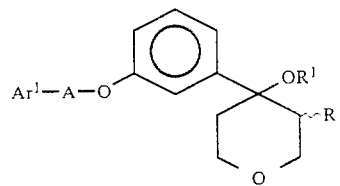

| Ex. 7 Compd. No. | Ar$^1$—A$^1$ | R$^1$ | R | m.p. (°C.) | Yield (%) |
|---|---|---|---|---|---|

NOTES a. The product displayed the following character NMR signals (CDCl$_3$, delta values): 2.0(m, 4H), 2.98(s, 3H), 3.82(m, 4H), 4.92(s, 2H), 7.0–7.4(m, 9H).

The 4-(3-hydroxyphenyl)-4-methoxytetrahydropyran used as a starting material was obtained as follows:-3-Methoxymethoxyphenyl bromide was prepared by the reaction of 3-bromophenol and dimethoxymethane using the general procedure described in Synthesis, 1976, 244. A Grignard reagent was prepared by heating a mixture of 3-methoxymethoxyphenyl bromide (6 g), magnesium (0.66 g) and tetrahydrofuran (34 ml) to 30° C. for 2 hours. The reagent was cooled to ambient temperature and a solution of tetrahydropyran-4-one (2.76 g) in tetrahydrofuran (2 ml) was added dropwise. The mixture was stirred at ambient temperature for 15 hours and evaporated. The residue was partitioned between ethyl acetate and water. The organic layer was washed with a saturated aqueous sodium chloride solution, dried (MgSO$_4$) and evaporated. The residue was purified by column chromatography using a 9:1 v/v mixture of methylene chloride and diethyl ether as eluent. There was thus obtained 4-hydroxy-4-(3-methoxymethoxyphenyl)tetrahydropyran (4.5 g, 69%), as an oil.

A mixture of a portion (2 g) of the product so obtained, sodium hydride (55% w/w dispersion in mineral oil, 0.74 g) and tetrahydrofuran (50 ml) was stirred at ambient temperature for 15 minutes. Methyl iodide (1.42 ml) and 15-crown-5 (0.1 g) were added and the mixture was stirred at ambient temperature for 15 hours. The mixture was evaporated and the residue was partitioned between methylene chloride and water. The organic layer was separated, washed with water, dried (MgSO$_4$) and evaporated. There was thus obtained 4-methoxy-4-(3-methoxymethoxyphenyl)tetrahydropyran (2.1 g, 98%), as an oil.

A mixture of the product so obtained, concentrated hydrochloric acid (0.8 ml), isopropanol (3.5 ml) and tetrahydrofuran (15 ml) was stirred at ambient temperature for 24 hours. The mixture was evaporated and the residue was partitioned between ethyl acetate and water. The organic layer was washed with a saturated aqueous sodium chloride solution, dried (MgSO$_4$) and evaporated. There was thus obtained 4-(3-hydroxyphenyl)-4-methoxytetrahydropyran (1.54 g, 93%), as a colourless oil, which was used without further purification.

b. The product displayed the following characteristic NMR signals (CDCl$_3$, delta values) 1.75–2.0(m, 1H), 2.3–2.75(m, 1H), 2.93(s, 3H), 2.94(s, 3H), 3.0–3.91(m, 5H), 4.91(s, 2H), 6.85–7.6(m, 9H). The 3- and 4-methoxy groups were in a trans-relationship.

The (3RS, 4SR)-4-(3-hydroxyphenyl)-3,4-dimethoxytetrahydropyran used as a starting material was obtained as follows:

A mixture of 4-hydroxy-4-(3methoxymethoxyphenyl)tetrahydropyran (2 g), 5-angstrom molecular sieves (20 g) and toluene (20 ml) was heated to 80° C. for 5 hours. The mixture was filtered and the residue was washed in succession with toluene and acetone. The combined filtrate and washings were combined and evaporated. The residue was purified by column chromatography using a 19:1 v/v mixture of methylene chloride and diethyl ether as eluent. There was thus obtained 2,3-dihydro-4-(3-methoxymethoxyphenyl)-6H-pyran (1.3 g, 70%), as an oil.

m-Chloroperbenzoic acid (1.53 g) was added to a stirred suspension of the product so obtained (1.3 g), sodium bicarbonate (0.75 g) and methylene chloride (15 ml) which had been cooled to 0° C., and the mixture was stirred at 0° C. for 1 hour and then at ambient temperature for 15 hours. The mixture was filtered and the residue was washed with methylene chloride. The combined filtrate and washings were washed with dilute aqueous sodium hydroxide solution, and with water, dried (MgSO$_4$) and evaporated. The epoxide (1.2 g, 92%) so obtained was used without further purification.

The procedure described in Tet. Let., 1968, 24, 1755 was used to react the epoxide (1.2 g) obtained above with sodium hydroxide. The product so obtained was purified by column chromatography using a 3:2 v/v mixture of methylene chloride and diethyl ether as eluent. There was thus obtained (3RS, 4SR)-3,4-dihydroxy-4-(3-methoxymethoxyphenyl) tetrahydropyran (0.7 g, 65%) as an oil; the 3-and 4-hydroxy groups being in a trans-relationship.

The product so obtained was reacted with methyl iodide (4 equivalents) in the presence of sodium hydride (2.5 equivalents) using the procedure described in Example 1. There was thus obtained (3RS, 4SR)-3,4-dimethoxy-4-(3-methoxymethoxyphenyl)tetrahydropyran (0.58 g, 77%) as an oil.

The product so obtained was reacted with hydrochloric acid using the procedure described in the third paragraph of the portion of Note a. There was thus obtained the required starting material (0.44 g, 92%), m.p. 146°-148° C.

c. The (3RS, 4SR)-3-hydroxy-4-(3-hydroxyphenyl)-4-methoxymethoxytetrahydropyran used as a starting material was obtained as follows:

The procedure described in the first paragraph of the portion of Note a. above which is concerned with the preparation of starting materials was repeated, except that 3-benzyloxyphenyl bromide was used in place of 3-methoxymethoxyphenyl bromide. The product so obtained was dehydrated using the procedure described in the first paragraph of the portion of Note b. above which is concerned with the preparation of starting materials. There was thus obtained 4-(3-benzyloxyphenyl)-2,3-dihydro-6H-pyran which was oxidised and the epoxide so obtained was reacted with sodium hydroxide using the procedures described in the second and third paragraphs of the portion of Note b. above which is concerned with the preparation of starting materials. There was thus obtained (3RS, 4SR)-4-(3-benzyloxyphenyl)-3,4-dihydroxytetrahydropyran in an overall yield of 42%, as an oil, the 3- and 4-hydroxy groups being in a trans-relationship.

A mixture of the product so obtained (1.76 g), imidazole (2 g), tert-butyldimethylsilyl chloride (2.26 g) and dimethylformamide (6 ml) was stirred at ambient temperature for 15 hours. The mixture was partitioned between diethyl ether and water. The organic layer was washed with water, dried (MgSO$_4$) and evaporated. The residue was purified by column chromatography using a 9:1 v/v mixture of methylene chloride and diethyl ether as eluent. There was thus obtained (3RS, 4SR)-4-(3-benzyloxyphenyl)-3-(tert-butyldimethylsilyloxy)-4-hydroxytetrahyropyran (1.9 g, 78%), m.p. 90°-92° C.

The product so obtained was methylated using the procedure described in Example 1. There was thus obtained (3RS, 4SR)-4-(3-benzyloxyphenyl)-3-(tert-butyldimethylsilyloxy)-4-methoxytetrahydropyran (1.69 g, 89%), as an oil.

Tetra-n-butylammonium fluoride (1 M in tetrahydrofuran; 16 ml) was added to a mixture of the compound so otained and tetrahydrofuran (32 ml) and the mixture was stirred at ambient temperature for 15 hours. The mixture was evaporated and the residue was partitioned between diethyl ether and water. The organic phase was dried (MgSO$_4$) and evaporated. The residue was purified by column chromatography using a 9:1 v/v mixture of methylene chloride and diethyl ether as eluent. There was thus obtained (3RS, 4SR)-4-methoxytetrahydropyran (1.06 g, 86%), m.p. 85°-86° C.

A mixture of the product so obtained, 10% palladium-on-charcoal catalyst (0.1 g) and ethanol (20 ml) was stirred at ambient temperature under an atmosphere of hydrogen for 15 hours. The mixture was filtered and evaporated and there was thus obtained the required starting material (0.7 g, 92%), m.p. 159°-160° C.

d. The (3SR, 4SR)-4-(3-hydroxyphenyl)-3,4-dimethoxytetrahydropyran used as a starting material was obtained as follows:

4-(3-Benzyloxyphenyl)-2,3-dihydro-6H-pyran, obtained as described in Note c. above, was oxidised using the procedure described in the second paragraph of the portion of Note b. above which is concerned with the preparation of starting materials. The epoxide (1 g) so produced was cleaved, using the procedure described in J. Org. Chem., 1979, 44 1646, to give (3SR, 4SR)-4-(3-benzyloxyphenyl)-3,4-dihydroxytetrahydropyran (1.06 g, 98%) which was used without further purification.

A portion (0.5 g) of the product so obtained was reacted with methyl iodide (4 equivalents) in the presence of sodium hydride (2.5 equivalents) using the procedure described in Example 1. The product so obtained was treated with hydrogen in the presence of palladium using the procedure described in the last paragraph of Note c. above. There was thus obtained the required starting material (0.3 g, 67%), m.p. 155°-156° C.

EXAMPLE 8

The procedure described in Example 5 was repeated using the appropriate alkylating agent and the appropriate phenol. There was thus obtained the compounds described in the following table:

TABLE III

Ar¹—A¹—O—Ar²—[tetrahydrofuran ring with R¹ and Me substituents, and O in ring]

| Ex. 8 Compd. No. | Ar¹—A¹ | Ar² | R¹ | m.p. (°C.) | Yield (%) |
|---|---|---|---|---|---|
| 1[a] | 7-fluoronaphth-2-ylmethyl | 1,3-phenylene | Me | 48–50 | 90 |
| 2[b] | 7-methylnaphth-2-ylmethyl | 1,3-phenylene | Me | 96–97 | 96 |
| 3[c] | 7-methylnaphth-2-ylmethyl | 5-fluoro-1,3-phenylene | Et | oil | 74 |
| 4[d] | 7-fluoronaphth-2-ylmethyl | 5-fluoro-1,3-phenylene | Et | oil | 86 |
| 5[e] | 3-phenylprop-2-ynyl | 1,3-phenylene | Me | oil | 87 |

NOTES a. The (2RS,3SR)-3-(3-hydroxyphenyl)-3-methoxy-2-methyltetrahydrofuran used as a starting material was obtained as follows:

The procedures described in Note a. of Example 7 were repeated except that 2-methyltetrahydrofuran-3-one was used in place of tetrahydropyran-4-one. There was thus obtained the required starting material in 54% yield, m.p. 170°–171° C.; the 2-methyl and 3-methoxy groups being in a cis-relationship.

The 2-bromomethyl-7-fluoronaphthalene used as starting material was obtained as described in the Notes below Table IV within Example 15 below.

b. The 2-bromomethyl-7-methylnaphthalene used as starting material was obtained from 2,7-dimethylnaphthalene using the methods described in the Notes below Table IV within Example 15 below.

c. The product displayed the following characteristic NMR signals (CDCl₃, delta values) 1.09(t, 3H), 1.25(s, 3H), 2.57(m, 2H), 2.59(s, 3H), 3.0–4.14(m, 5H), 5.19(s, 2H), 6.5–7.9(m, 9H).

The (2RS,3SR)-3-ethoxy-3-(5-fluoro-3-hydroxyphenyl)-2-methyltetrahydrofuran used as a starting material was obtained as follows:

A Grignard reagent was prepared by heating a mixture of 3-benzyloxy-5-fluorophenyl bromide (4.2 g), magnesium powder (0.365 g) and tetrahydrofuran (20 ml) to 40° C. for 1 hour. The reagent was cooled to ambient temperature and 2-methyltetrahydrofuran-3-one (1.16 ml) was added dropwise. The mixture was stirred at ambient temperature for 3 hours and then partitioned between ethyl acetate and water. The organic layer was washed with water, dried (MgSO₄) and evaporated. The residue was purified by column chromatography using a 19:1 v/v mixture of methylene chloride and diethyl ether as eluent. There was thus obtained (2RS,3SR)-3-(3-benzyloxy-5-fluorophenyl)-3-hydroxy-2-methyltetrahydrofuran (2.3 g, 64%), m.p. 83°–84° C.; the 2-methyl and 3-hydroxy groups being in a cis-relationship. A portion (1.1 g) of the product so obtained was reacted with ethyl iodide using the procedure described in Example 1. There was thus obtained (2RS,3SR)-3-(3-benzyloxy-5-fluorophenyl)-3-ethoxy-2-methyltetrahydrofuran (0.82 g, 68%), as an oil.

A mixture of the product so obtained, 10% palladium-on-charcoal (0.1 g) and ethanol (5 ml) was stirred at ambient temperature under an atmosphere of hydrogen for 4 hours. The mixture was filtered and evaporated. There was thus obtained the required starting material (0.54 g, 92%), m.p. 136°–137° C.

d. The product displayed the following characteristic NMR signals (CDCl₃, delta values) 1.09–1.25(2 t's, 6H), 2.43(t, 2H), 3.0–4.2(m, 5H), 5.20(s, 2H), 6.5–7.98(m, 9H).

e. The product displayed the following characteristic NMR signals (CDCl₃, delta values) 1.2(d, 3H), 2.35–2.6(m, 2H), 3.17(s, 3H), 3.72(q, 1H), 3.9–4.25(m, 2H), 4.93(s, 2H), 6.8–7.5(m, 9H).

EXAMPLE 9

The procedure described in Example 1 was repeated except that allyl bromide was used in place of methyl iodide and dimethylformamide was used in place of tetrahydrofuran. There was thus obtained 4-allyloxy-4-[3-(naphth-2-ylmethoxy)phenyl]tetrahydropyran (57%), as an oil.

NMR Spectrum (CDCl₃, delta values) 1.8–2.2(m, 4H), 3.5–3.65(m, 2H), 3.75–4.1(m, 4H), 5.0–5.4(m, 4H), 5.6–6.1(m, 1H), 6.8–8.0(m, 11H).

EXAMPLE 10

The procedure described in Example 1 was repeated except that ethyl iodide was used in place of methyl iodide and dimethylformamide was used in place of tetrahydrofuran. There was thus obtained 4-ethoxy-4-[3-(naphth-2-ylmethoxy)phenyl]tetrahydropyran (60%), as an oil.

NMR Spectrum (CDCl₃, delta values) 1.1(t, 3H), 1.96(m, 4H), 3.07(q, 2H), 3.8(m, 4H), 5.23(s, 2H), 6.8–7.9(m, 11H).

EXAMPLE 11

Using the procedure described in Example 1, (3RS,4SR)-3-hydroxy-4-methoxy-4-[3-(naphth-2-ylmethoxy)phenyl]tetrahydropyran [Example 7, Compound No. 3] was reacted with methyl iodide to give (3RS,4SR)-3,4-dimethoxy-4-[3-(naphth-2-ylmethoxy)phenyl]tetrahydropyran (90%), m.p. 131°–133° C.

The reaction described immediately above was repeated except that propargyl bromide was used in place of methyl iodide. There was thus obtained (3RS,4SR)-4-methoxy-4-[3-(naphth-2-ylmethoxy)phenyl]-3-(prop-2-ynyloxy)tetrahydropyran (62%), m.p. 86°–88° C.

EXAMPLE 12

Using the procedure described in Example 1, 4-hydroxy-4-[3-(naphth-2-ylmethoxy)phenyl]oxepane was reacted with methyl iodide to give 4-methoxy-4-[3-(naphth-2-ylmethoxy)phenyl]oxepane (36%), m.p. 69°–70° C.

The reaction described immediately above was repeated except that allyl bromide was used in place of methyl iodide and dimethylformamide was used as the reaction solvent. There was thus obtained 4-allyloxy-4-[3-(naphth-2-ylmethoxy)phenyl]oxepane (25%), m.p. 57°–58° C.

The 4-hydroxy-4-[3-(naphth-2-ylmethoxy)phenyl]oxepane used as a starting material was obtained using the procedure described in the portion of Example 1 which is concerned with the preparation of starting materials except that 4-ketooxepane (*Chem. Ber.*, 1958, 91, 1589) was used in place of tetrahydropyran-4-one.

EXAMPLE 13

A solution of n-butyl-lithium (0.625 ml of a 1.6M solution in hexane) was added dropwise to a solution of 2-methoxy-2-[3-(naphth-2-ylmethoxy)phenyl]propane-1,3-diol and tetrahydrofuran which had been cooled to 0° C. A solution of p-toluenesulphonyl chloride (0.19 g) in tetrahydrofuran (1 ml) was added and the mixture was stirred at 0° C. for 30 minutes.

A solution of n-butyl-lithium (0.625 ml, 1.6M) was added and the mixture was heated to 60° C. for 4 hours. The mixture was evaporated and the residue was partitioned between diethyl ether and water. The organic layer was separated, washed with water, dried (MgSO$_4$) and evaporated. The residue was purified by column chromatography using a 5:1 v/v mixture of methylene chloride and diethyl ether as eluent. There was thus obtained 3-methoxy-3-[3-(naphth-2-ylmethoxy)phenyl]oxetane (0.072 g, 22%), m.p. 71°–72° C.

The 2-methoxy-2-[3-(naphth-2-ylmethoxy)phenyl]propane-1,3-diol used as a starting material was obtained as follows:

A Grignard reagent was prepared by heating a mixture of 3-benzyloxyphenyl bromide (2.55 g), magnesium powder (0.232 g) and tetrahydrofuran (20 ml) to 60° C. for 1 hour. A solution of benzyloxyacetonitrile (1.36 g) in tetrahydrofuran (1 ml) was added dropwise and the mixture was heated to 60° C. for 60 minutes. The mixture was acidified by the addition of 1N hydrochloric acid solution (50 ml) and extracted with diethyl ether. The organic layer was washed with water and with a saturated aqueous sodium chloride solution, dried (MgSO$_4$) and evaporated. The residue was purified by column chromatography using methylene chloride as eluent. There was thus obtained benzyloxymethyl 3-(naphth-2-ylmethoxy)phenyl ketone (2.11 g, 65%) as an oil.

A solution of this product (2.1 g) in tetrahydrofuran (3 ml) was added dropwise to a solution of isopropoxydimethylsilymethylmagnesium chloride [prepared as described in *J. Org. Chem.*, 1983, 48, 2120, from chloromethylisopropoxydimethylsilane (1.88 g) and magnesium powder (0.27 g) in tetrahydrofuran (15 ml)]. The mixture was stirred at ambient temperature for 1 hour, washed with a saturated aqueous solution of ammonium chloride and then with a saturated aqueous solution of sodium chloride. The organic layer was separated, dried (Na$_2$SO$_4$) and evaporated to give 3-benzyloxy-2-(3-benzyloxyphenyl)-1-isopropoxydimethylsilylpropan-2-ol, as a yellow oil.

A mixture of the product so obtained, sodium bicarbonate (0.58 g), hydrogen peroxide (3 ml, 30% w/v in water), methanol (10 ml) and tetrahydrofuran (10 ml) was heated to reflux for 15 hours. The mixture was evaporated to remove the organic solvents and the residue was extracted with diethyl ether. The organic layer was separated, washed with a saturated aqueous solution of sodium chloride, dried (MgSO$_4$) and evaporated. The residue was purified by column chromatography using initially methylene chloride and then increasingly polar mixtures of methylene chloride and acetone, up to a 9:1 v/v mixture, as eluent. There was thus obtained 3-benzyloxy-2-(3-benzyloxyphenyl)propane-1,2-diol (2 g, 87%), as an oil.

A mixture of the product so obtained, tert-butyldimethylsilyl chloride (0.99 g), imidazole (0.45 g) and dimethylformamide (10 ml) was stirred at ambient temperature for 15 hours. The mixture was evaporated and the residue was purified by column chromatography using methylene chloride as eluent. There was thus obtained 3-benzyloxy-2-(3-benzyloxyphenyl)-1-tert-butyldimethylsilyloxypropan-2-ol as a colourless oil (2.14 g, 81%).

This product was methylated using the procedure described in Example 1. There was thus obtained 3-benzyloxy-2-(3-benzyloxyphenyl)-2-methoxyprop-1-yl tert-butyldimethylsilyl ether (2.02 g, 70%), as an oil.

A mixture of a portion (2 g) of the product so obtained, tetrahydrofuran (20 ml) and tetrabutylammonium fluoride (9 ml of a 1M solution in tetrahydrofuran) was stirred at ambient temperature for 15 hours. The mixture was evaporated and the residue was partitioned between methylene chloride and water. The organic layer was separated, washed with water, dried (MgSO$_4$) and evaporated. The residue was purified by column chromatography using initially methylene chloride and then increasingly polar mixtures of methylene chloride and diethyl ether, up to a 9:1 v/v mixture, as eluent. There was thus obtained 3-benzyloxy-2-(3-benzyloxyphenyl)-2-methoxypropan-1-ol (1.54 g, 99%).

A mixture of the product so obtained, 10% palladium-on-charcoal (0.18 g) and ethanol (12 ml) was stirred at ambient temperature under an atmosphere of hydrogen for 48 hours. The mixture was filtered and evaporated. There was thus obtained 2-(3-hydroxyphenyl)-2-methoxypropane-1,3-diol (0.67 g, 82%), as an oil.

The product so obtained was reacted with 2-bromomethylnaphthalene using the procedure described in Example 5. There was thus obtained the required starting material (0.68 g, 60%), m.p. 128°–129° C.

EXAMPLE 14

Sodium hydride (50% w/w dispersion in mineral oil, 0.024 g) was added to a mixture of (2RS,3SR)-3-(5-hydroxypyrid-3-yl)-3-methoxy-2-methyltetrahydrofuran (0.104 g) and dimethylformamide (5 ml) which had been cooled to −10° C. and the mixture was stirred at that temperature for 1 hour. The mixture was cooled to −15° C., 3-phenylprop-2-ynyl bromide (0.097 g) was added and the mixture was stirred for 1 hour. The mixture was partitioned between diethyl ether and a saturated aqueous ammonium chloride solution. The organic phase was dried (MgSO$_4$) and evaporated. The residue was purified by column chromatography using a 3:2 v/v mixture of methylene chloride and diethyl ether as eluent. There was thus obtained (2RS,3SR)-3-methoxy-2-methyl-3-[5-(3-phenylprop-2-ynyloxy)pyrid-3-yl]tetrahydrofuran (0.11 g, 68%), as an oil.

NMR Spectrum (CDCl$_3$, delta values) 1.2(d, 3H), 2.25–2.8(m, 4H), 3.25(s, 3H), 3.6–3.95(m, 1H), 3.95–4.3(m, 2H), 5.15(s, 2H), 7.25–7.5(m, 5H), 8.0–8.15(m, 1H), 8.4–8.6(m, 2H).

The (2RS,3SR)-3-(5-hydroxyprid-5-yl)-3-methoxy-2-methyltetrahydrofuran used as a starting material was obtained as follows:

Sodium hydride (50% w/w dispersion in mineral oil, 5 g) was added portionwise to a mixture of benzyl alcohol (12.4 g) and dimethylformamide (150 ml) which had been cooled to 0° C. The mixture was allowed to warm to ambient temperature and was stirred for 1 hour. 3,5-Dibromopyridine (25.2 g) was added and the mixture was heated to 60° C. for 2 hours. The mixture was cooled to ambient temperature and partitioned between ethyl acetate and a dilute aqueous potassium carbonate solution. The organic layer was washed with a dilute aqueous hydrochloric acid solution and with a saturated aqueous sodium chloride solution, dried (MgSO$_4$) and evaporated. The residue was a red oil which on trituration under petroleum ether (b.p. 60°-80° C.) gave 5-benzyloxy-3-bromopyridine (18.6 g, 67%), m.p. 65°-67° C.

A solution of a portion (11.5 g) of this product in diethyl ether (500 ml) was cooled to −50° C. and n-butyl-lithium (1.5M in hexane, 32 ml) was added dropwise. The mixture was stirred at −50° C. for 20 minutes, further cooled to −60° C. and a solution of 2-methyltetrahydrofuran-3-one (5 g) in diethyl ether (50 ml) was added. The mixture was stirred at −60° C. for 1 hour and at −30° C. for 30 minutes. A saturated aqueous ammonium chloride solution (200 ml) was added and the mixture was extracted with ethyl acetate (3×50 ml). The combined organic extracts were washed with a saturated aqueous sodium chloride solution, dried (MgSO4) and evaporated. The residue was purified by column chromatography using a 7:3 v/v mixture of toluene and ethyl acetate as eluent. There was thus obtained (2RS,3SR)-3-(5-benzyloxypyrid-3-yl)-3-hydroxy-2-methyltetrahydrofuran (7.8 g, 63%), as an oil; the 2-methyl and 3-hydroxy groups being in a cis-relationship.

NMR Spectrum (CDCl3, delta values) 1.1(d, 3H), 2.3-2.8(m, 2H), 3.8-4.3(m, 3H), 5.1(s, 2H), 7.35(s, 5H), 7.6(m, 1H), 8.3(m, 2H).

The product so obtained was converted, using the procedures described in Example 3 and in the portion of Example 5 which is concerned with the preparation of starting materials, to the required starting material (90%), as an oil.

NMR Spectrum (CDCl3, delta value) 1.15(d, 3H), 2.45(t, 2H), 3.10(s, 3H), 3.69-3.9(m, 1H), 3.9-4.3(m, 2H), 7.25-7.4(m, 1H), 8.0-8.3(m, 2H).

EXAMPLE 15

The procedure described in Example 5 was repeated using the appropriate alkyl bromide and the appropriate phenol. There were thus obtained the compounds described in the following table:

TABLE IV $Ar^1-CH_2-O-Ar^2$ (tetrahydropyran with $OR^1$)

| Ex. 15 Compd. No. | Ar$^1$ | Ar$^2$ | R$^1$ | m.p. (°C.) | Yield (%) |
|---|---|---|---|---|---|
| 1$^a$ | 6-fluoro-naphth-2-yl | 5-fluoro-1,3-phenylene | Me | 85 | 88 |
| 2 | 7-fluoro-naphth-2-yl | 5-fluoro-1,3-phenylene | Me | 109–110 | 76 |
| 3$^b$ | 6,7-difluoro-naphth-2-yl | 5-fluoro-1,3-phenylene | Me | oil | 54 |
| 4 | 5-cyano-naphth-2-yl | 5-fluoro-1,3-phenylene | Me | 134–136 | 41 |
| 5 | 7-difluoromethyl-naphth-2-yl | 5-fluoro-1,3-phenylene | Me | 89 | 84 |
| 6 | 7-methyl-naphth-2-yl | 5-fluoro-1,3-phenylene | Me | 114 | 91 |
| 7 | 4-cyano-phenyl | 5-fluoro-1,3-phenylene | Me | 133–134 | 82 |
| 8* | 4-methyl-thiophenyl | 5-fluoro-1,3-phenylene | Me | 72–74 | 66 |
| 9 | 3-methoxycarbonyl-phenyl | 5-fluoro-1,3-phenylene | Me | 97–100 | 85 |
| 10$^c$ | 4-tert-butyl-phenyl | 5-fluoro-1,3-phenylene | Me | oil | 70 |
| 11$^d$ | 4-n-propyl-phenyl | 5-fluoro-1,3-phenylene | Me | oil | 84 |
| 12$^e$ | 7-fluoro- | 5-trifluoro- | Et | 88–89 | 86 |

TABLE IV-continued $Ar^1-CH_2-O-Ar^2$ (tetrahydropyran with $OR^1$)

| Ex. 15 Compd. No. | Ar$^1$ | Ar$^2$ | R$^1$ | m.p. (°C.) | Yield (%) |
|---|---|---|---|---|---|
| | naphth-2-yl | methyl-1,3-phenylene | | | | a. The 4-(5-fluoro-3-hydroxyphenyl)-4-methoxytetrahydropyran used as a starting material was obtained as follows:

A solution of n-butyl-lithium (22 ml of a 1.6M solution in hexane) was added over 15 minutes to a solution of benzyl 3-bromo-5-fluorophenyl ether (9.75 g) in tetrahydrofuran (150 ml) which had been cooled to −75° C. and the mixture was stirred at this temperature for 1 hour. A solution of tetrahydropyran-4-one (3.47 g) in tetrahydrofuran (10 ml) was added over a further 15 minutes and the mixture was stirred at −75° C. for 1 hour. The mixture was allowed to warm to 0° C. over approximately 2 hours. A saturated aqueous ammonium chloride solution (50 ml) was added and the organic phase was separated. The aqueous phase was extracted with ethyl acetate (3×30 ml). The combined organic phases were dried (MgSO4) and evaporated. The residue was purified by column chromatography using a 2:1 v/v mixture of toluene and ethyl acetate as eluent. There was thus obtained 4-(3-benzyloxy-5-fluorophenyl)-4-hydroxytetrahydropyran (7.4 g, 70%), as an oil.

NMR Spectrum (CDCl3, delta values) 1.6(m, 2H), 2.05-2.2(m, 2H), 3.8-4.0(m, 4H), 5.05(s, 2H), 6.6(d, 1H), 6.8(d 1H), 6.9(s, 1H), 7.15-7.45(m, 5H).

After appropriate repetition of the above reaction, a mixture of the product so obtained (12.1 g), sodium hydride (50% w/w dispersion in mineral oil; 2.11 g) and tetrahydrofuran (150 ml) was stirred at ambient temperature for 1 hour. The mixture was cooled to 0° C. and methyl iodide (3.75 ml) was added. The mixture was stirred at ambient temperature for 15 hours. Aqueous 2N hydrochloric acid solution was added until no further effervescence occurred and the organic solvent was evaporated. The residue was partitioned between ethyl acetate and water. The organic phase was washed with a saturated aqueous sodium chloride solution, dried (MgSO4) and evaporated. There was thus obtained 4-(3-benzyloxy-5-fluorophenyl)-4-methoxytetrahydropyran, as a light yellow oil (12.5 g), which was used without further purification.

A mixture of the product so obtained, 10% palladium-on-charcoal catalyst (0.7 g) and absolute ethanol (100 ml) was stirred under an atmosphere of hydrogen for 3 hours. The mixture was filtered and evaporated. There was thus obtained the required starting material (7.7 g, 86%), m.p. 123°–124° C.

b. The product displayed the following characteristic NMR signals (CDCl3, delta values) 1.92(m, 4H), 2.97(s, 3H), 3.80(m, 4H), 5.19(s, 2H), 6.66-6.85(m, 3H), 7.5-7.61(m, 3H), 7.81(d, 2H).

c. The product displayed the following characteristic NMR signals (CDCl3, delta values) 1.35(s, 9H), 1.85-2.05(m, 4H), 3.0(s, 3H), 3.75-3.90(m, 4H), 5.0(s, 2H), 6.6(d of t's, 1H), 6.7(d of t's, 1H), 6.8(t, 1H), 7.35(d, 2H), 7.4(d, 2H).

d. The product displayed the following characteristic NMR signals (CDCl$_3$, delta values) 0.98(t, 3H), 1.62(m, 2H), 1.9–1.98(m, 4H), 2.6(t, 2H), 2.97(s, 3H), 3.78–3.85(m, 4H), 5.01(s, 2H), 6.61(d of t's, 1H), 6.7(d of t's, 1H), 6.78(t, 1H), 7.19(d, 2H), 7.23(d, 2H).

e. The 4-ethoxy-4-(3-hydroxy-5-trifluoromethylphenyl)tetrahydropyran used as a starting material was obtained as follows:

Sodium hydride (55% w/w dispersion in mineral oil; 4.36 g) was added portionwise to a mixture of benzyl alcohol (9.82 ml) and dimethylacetamide (136 ml) which had been cooled in an ice-bath. The mixture was stirred at ambient temperature for 1.5 hours and then recooled in an ice-bath. A solution of 3-fluoro-5-trifluoromethylbromobenzene (22.1 g) in dimethylacetamide (136 ml) was added and the mixture was stirred at ambient temperature for 2 hours. The mixture was evaporated and the residue was partitioned between diethyl ether and water. The organic phase was washed with a saturated aqueous sodium chloride solution, dried (MgSO$_4$) and evaporated. The residue was purified by column chromatography using hexane as eluent. There was thus obtained 3-benzyloxy-5-trifluoromethylbromobenzene (23.1 g, 77%), as a colourless liquid.

NMR Spectrum 5.07(s, 2H), 7.15–7.35(3 s's, 3H), 7.36–7.42(m, 5H).

A solution of n-butyl-lithium (25.9 ml of a 1.6M solution in hexane) was added dropwise to a solution of a portion (13.75 g) of the compound so obtained in tetrahydrofuran (150 ml) which had been cooled to −70° C. The mixture was stirred at this temperature for 1 hour. A solution of tetrahydropyran-4-one (4.15 g) in tetrahydrofuran (5 ml) was added dropwise and the mixture was stirred at −70° C. for 1 hour, and then allowed to warm to 0° C. A saturated aqueous ammonium chloride solution (100 ml) was added and the mixture was extracted with diethyl ether. The organic phase was washed with a saturated aqueous sodium chloride solution, dried (MgSO$_4$) and evaporated. The residue was purified by column chromatography using a 4:1 v/v mixture of toluene and ethyl acetate as eluent. There was thus obtained 4-(3-benzyloxy-5-trifluoromethylphenyl)-4-hydroxytetrahydropyran (11.5 g, 79%), as a solid.

NMR Spectrum (CDCl$_3$, delta values) 1.6–1.72(m, 2H), 2.05–2.25(m, 2H), 3.6–4.0(m, 4H), 5.12(s, 2H), 7.1–7.5(m, 8H).

Powdered potassium hydroxide (1.5 g) was added to a solution of a portion (2.17 g) of the product so obtained in dimethylsulphoxide (15 ml) and the mixture was stirred at ambient temperature for 10 minutes. Ethyl iodide (1.24 ml) was added and the mixture was stirred at ambient temperature for 4 hours. The mixture was poured onto a mixture of diethyl ether and ice. The organic phase was separated, washed with water, dried (MgSO$_4$) and evaporated. The residue was purified by column chromatography using a 10:1 v/v mixture of toluene and ethyl acetate as eluent. There was thus obtained 4-(3-benzyloxy-5-trifluoromethylphenyl)-4-ethoxytetrahydropyran (1.75 g, 74%), as an oil.

NMR Spectrum (CDCl$_3$, delta values) 1.1–1.2(t, 3H), 1.8–2.1(m, 4H), 3.0–3.1(q, 2H), 3.75–3.95(m, 4H), 5.1(s, 2H), 7.1–7.5(m, 8H).

A mixture of the product so obtained, 10% palladium-on-charcoal catalyst (0.35 g) and isopropanol (25 ml) was stirred under an atmosphere of hydrogen for 3.5 hours. The mixture was filtered and evaporated. There was thus obtained the required starting material (1.3 g, 97%), as an oil.

NMR Spectrum (CDCl$_3$, delta values) 1.1–1.2(t, 3H), 1.9–2.1(m, 4H), 3.05–3.15(q, 2H), 3.8–4.0(m, 4H), 7.0(m, 1H), 7.1(m, 1H), 7.2(s, 1H).

Information concerning the preparation of appropriate starting materials for the compounds described within Example 15 is provided below:

(i) The procedure used to prepare the appropriate 2bromomethylnaphthalenes for use in the preparation of compounds Nos. 1 to 6 is illustrated below by the description of the preparation of 2-bromomethyl-5-cyanonaphthalene. The other 2-bromomethylnaphthalenes were prepared in analogous fashion. Thus:

A mixture of 5-cyano-2-methylnaphthalene (0.75 g), N-bromosuccinimide (0.81 g), 2,2'-azobisisobutyronitrile (0.05 g) and carbon tetrachloride (25 ml) was heated to reflux and irradiated with the light from a 275 watt bulb for 1 hour. The mixture was cooled to ambient temperature and filtered. The filtrate was evaporated and the residue was recrystallised from carbon tetrachloride. There was thus obtained 2-bromomethyl-5-cyanonaphthalene (0.64 g), m.p. 104°–106° C.

The procedure described immediately above was repeated except that the appropriate 2-methylnaphthalene was used in place of 5-cyano-2-methylnaphthalene and the reaction product was purified by column chromatography using increasingly polar mixtures of petroleum ether (b.p. 60°–80° C.) and toluene as eluent. There were thus obtained the 2-bromomethylnaphthalenes listed below:

2-bromomethyl-6-fluoronaphthalene[a], m.p. 48° C.;
2-bromomethyl-7-fluoronaphthalene[b], m.p. 62° C.;
2-bromomethyl-6,7-difluoronaphthalene[c], oil;
2-bromomethyl-7-difluoromethylnaphthalene[d], m.p. 70°–71° C.; and
2-bromomethyl-7-methylnaphthalene, m.p. 100° C.

NOTES a. 2-Methyl-6-fluoronaphthalene used as a starting material was obtained as follows: 4-Fluorobenzyl chloride was reacted with acetylacetaldehyde dimethylacetal using the procedure described for the corresponding reaction of 3-methylbenzyl chloride (*Synthesis*, 1974, 566). There was thus obtained 4-(4-fluorophenyl)-3-hydroxy-3-methylbutanal dimethylacetal (b.p. 122°–130° C. at 0.2 mm Hg). A mixture of the material so obtained (15 g), glacial acetic acid (60 ml) and hydrobromic acid (48% w/v, 48 ml) was heated on a steam bath for 1 hour. The mixture was evaporated and the residue was purified by column chromatography using petroleum ether (b.p. 60°–80° C.) as eluent. There was thus obtained 6-fluoro-2-methylnaphthalene (1 g).

b. The procedure described in Note a. above was repeated except that 3-fluorobenzyl chloride was used. There was thus obtained 7-fluoro-2-methylnaphthalene as a white solid.

c. The procedure described in Note a. above was repeated except that 3,4-difluorobenzyl bromide was used as a starting material. There was thus obtained 6,7-difluoro-2-methylnaphthalene as a white solid (11%), m.p. 63°–64° C.

d. 7-Difluoromethyl-2-methylnaphthalene used as a starting material was obtained as follows:

A mixture of 2-methyl-7-naphthaldehyde (0.37 g; *Bull Soc. Chim. Belg.*, 1985, 94, 205), diethylaminosulphur trifluoride (0.3 ml) and methylene chloride (3 ml) was stirred at ambient temperature for 16 hours. A second portion of the trifluoride (0.6 ml) was added and the reaction was continued for a further 24 hours. The mixture was partitioned between methylene chloride and water. The organic layer was washed with water, dried (MgSO$_4$) and evaporated. The residue was purified by column chromatography using a 19:1 v/v mixture of petroleum ether (b.p. 60°–80° C.) and toluene as eluent. There was thus obtained 7-difluoromethyl-2-methylnaphthalene as a solid (0.13 g).

(ii) 4-Methylthiobenzyl chloride used in the preparation of Compound No. 8 was obtained as follows:

Thionyl chloride (1.56 ml) was added dropwise to a solution of 4-methylthiobenzyl alcohol (3 g) in toluene (15 ml) which had been cooled to 0° C. The mixture was stirred for 1 hour and allowed to warm to ambient temperature. The mixture was evaporated and the residue was purified by being washed through a small amount of silica using a 10:1 v/v mixture of toluene and ethyl acetate as eluent. There was thus obtained the required starting material (2.8 g, 85%), as a liquid.

(iii) 4-n-Propylbenzyl bromide used in the preparation of Compound No. 11 was obtained from 4-n-propylbenzoic acid by the conventional procedure of reduction with lithium aluminium hydride to form 4-n-propylbenzyl alcohol and reaction of that product with phosphorus tribromide.

EXAMPLE 16

Using the procedure described in Example 3, 4-[5-fluoro-3-(naphth-2-ylmethoxy)phenyl]-4-hydroxytetrahydropyran was reacted with methyl iodide to give 4-[5-fluoro-3-(naphth-2-ylmethoxy)phenyl]-4-methoxytetrahydropyran in 98% yield, m.p. 109°–111° C.

The 4-(5-fluoro-3-(naphth-2-ylmethoxy)phenyl)-4-hydroxytetrahydropyran used as a starting material was obtained as follows:

The procedures described in Note a. of Example 15 were repeated except that the methylation step was omitted. There was thus obtained 4-(5-fluoro-3-hydroxyphenyl)-4-hydroxytetrahydropyran (60%), m.p. 158°–160° C.

A portion of (2.12 g) of the product so obtained was reacted with 2-bromomethylnaphthalene (2.21 g) in the presence of potassium carbonate (2.8 g) and dimethylformamide (20 ml) using the procedure described in Example 5. There was thus obtained the required starting material (3.02 g, 85%), m.p. 99°–101° C.

EXAMPLE 17

Powdered potassium hydroxide (0.2 g) and 1,4,7,10,13,16-hexaoxacyclooctadecane (hereinafter 18-crown-6; 0.04 g) were added in succession to a mixture of 4-[5-fluoro-3-(naphth-2-ylmethoxy)phenyl]-4-hydroxytetrahydropyran (0.352 g) and tetrahydrofuran (2.5 ml) and the mixture was stirred at ambient temperature for 5 minutes. Propargyl bromide (80% w/v solution in toluene; 0.3 ml) was added and the mixture was stirred at ambient temperature for 18 hours. The mixture was partitioned between ethyl acetate and a saturated aqueous ammonium chloride solution. The organic phase was washed with a saturated aqueous sodium chloride solution, dried (MgSO$_4$) and evaporated. The residue was purified by column chromatography using increasingly polar mixtures of hexane and ethyl acetate as eluent. There was thus obtained 4-[5-fluoro-3-(naphth-2-ylmethoxy)phenyl]-4-(prop-2-ynyloxy)tetrahydropyran (0.32 g, 82%), m.p. 85°–87° C.

EXAMPLE 18

The procedure described in Example 17 was repeated using the appropriate alkyl halide and the appropriate 4-hydroxytetrahydropyran. There were thus obtained the compounds described in the following table:

TABLE V

Ar$^1$—CH$_2$—O—Ar$^2$ [tetrahydropyran with OR$^1$]

| Ex. 18 Compd. No. | Ar$^1$ | Ar$^2$ | R$^1$ | m.p. (°C.) | Yield (%) |
|---|---|---|---|---|---|
| 1$^a$ | 2-naphthyl | 5-fluoro-1,3-phenylene | Et | 64–65 | 66 |
| 2$^b$ | 2-naphthyl | 5-fluoro-1,3-phenylene | allyl | oil | 71 |

NOTES a. Ethyl iodide was used.

b. Allyl bromide was used. The product displayed the following characteristic NMR signals (CDCl$_3$, delta values) 1.89–2.05(m, 4H), 3.6(d of t's, 2H), 3.75–3.95(m, 4H), 5.06–5.3(m, 2H), 5.2(s, 2H), 5.7–5.9(m, 1H), 6.6–6.8(m, 2H), 6.88(t, 1H), 7.45–7.55(m, 3H), 7.8–7.9(m, 4H).

EXAMPLE 19

The procedure described in Example 5 was repeated using 4-(5-fluoro-3-hydroxyphenyl)-4-methoxytetrahydropyran in place of the corresponding 2-methyltetrahydropyran. There was thus obtained 4-[5-fluoro-3-(3-phenylprop-2-ynyloxy)phenyl]-4-methoxytetrahydropyran (70%), as an oil.

NMR Spectrum (CDCl$_3$, delta values) 1.94(m, 4H), 2.99(s, 3H), 3.82(m, 4H), 4.91(s, 2H), 6.65–6.88(m, 3H), 7.18–7.45(m, 5H);

Mass Spectrum P m/e 340;

Elemental Analysis Found C, 73.9; H, 5.6; C$_{21}$H$_{21}$FO$_3$ requires C, 74.1; H, 6.2%.

EXAMPLE 20

A solution of 4-[5-fluoro-3-(2-propynyloxy)phenyl]-4-methoxytetrahydropyran (0.35 g) in acetonitrile (1.5 ml) was added to a mixture of 2-chlorophenyl iodide (0.36 g), bis(triphenylphosphine)palladium chloride (0.015 g), triethylamine (0.2 ml), cuprous iodide (0.015 g), and acetonitrile (4 ml) and the mixture was stirred at 55° C. for 2 hours. The mixture was cooled to ambient temperature and partitioned between diethyl ether and water. The organic phase was washed with water and with a saturated aqueous sodium chloride solution, dried (MgSO$_4$) and evaporated. The residue was purified by column chromatography using a 2:1 v/v mixture of hexane and ethyl acetate as eluent. There was thus obtained 4-[5-fluoro-3-(3-(2-chlorophenyl)prop-2-ynyloxy)phenyl]-4-methoxytetrahydropyran (0.26 g, 53%), m.p. 120°–122° C.

The 4-[5-fluoro-3-(2-propynyloxy)phenyl]-4-methoxytetrahydropyran used as a starting material was obtained as follows:

A mixture of 4-(5-fluoro-3-hydroxyphenyl)-4-methoxytetrahydropyran (5.34 g), propargyl bromide (80% w/v in toluene, 4.46 ml), potassium carbonate (5.52 g) and acetone (150 ml) was heated to reflux for 16 hours. The mixture was filtered and evaporated. The residue was partitioned between ethyl acetate and water. The organic phase was washed with water and with a saturated aqueous sodium chloride solution, dried (MgSO4) and evaporated. The residue was purified by column chromatography using a 2:1 v/v mixture of ethyl acetate and hexane as eluent. There was thus obtained the required starting material (5.77 g, 91%), m.p. 71°–72° C.

EXAMPLE 21

The procedure described in Example 20 was repeated using the appropriate phenyl iodide and the appropriate alkyne. There was thus obtained the compounds described in the following table:

TABLE VI $$Ar^1-C\equiv C-CH_2-O-\text{[phenyl]}-\text{[tetrahydropyran with }OR^1\text{]}$$

| Ex. 21 Compd. No. | Ar$^1$ | R$^1$ | m.p. (°C.) | Yield (%) |
|---|---|---|---|---|
| 1$^a$ | 3-chlorophenyl | Me | oil | 64 |
| 2 | 4-chlorophenyl | Me | oil | 55 |
| 3 | 4-fluorophenyl | Me | oil | 52 |
| 4$^b$ | 2-cyanophenyl | Me | oil | 43 |
| 5$^c$ | 3-cyanophenyl | Me | oil | 72 |
| 6 | 4-cyanophenyl | Me | oil | 43 |
| 7 | 2-trifluoromethylphenyl | Me | 60–61 | 21 |
| 8 | 3-trifluoromethylphenyl | Me | oil | 65 |
| 9 | 2-aminophenyl | Me | oil | 38 |
| 10 | 3-aminophenyl | Me | oil | 16 |
| 11 | 4-aminophenyl | Me | oil | 23 |
| 12$^d$ | 2-methylsulphonylphenyl | Me | oil | 35 |
| 13$^e$ | 2-cyanomethoxyphenyl | Me | oil | 46 |
| 14$^f$ | 3-cyanomethoxyphenyl | Me | oil | 65 |
| 15$^g$ | 3-aminomethylphenyl | Me | oil | 36 |
| 16$^h$ | 3-(2-cyanoprop-2-yl)phenyl | Me | 78–81 | 71 |
| 17 | 3,5-dichlorophenyl | Me | oil | 73 |
| 18 | 2,4-difluorophenyl | Me | oil | 46 |
| 19 | 3,4-difluorophenyl | Me | oil | 29 |
| 20 | 3,5-di(trifluoromethyl)phenyl | Me | oil | 77 |
| 21$^i$ | 2,5-dimethylphenyl | Me | oil | 41 |
| 22 | 2-chloro-5-trifluoromethylphenyl | Me | oil | 77 |
| 23 | 2-cyano-3-fluorophenyl | Me | oil | 57 |
| 24$^j$ | 2-methylthio-5-trifluoromethylphenyl | Me | oil | 48 |

NOTES

Unless otherwise stated the required substituted phenyl iodides were commercially available.

For those products which were obtained as oils, characterisation was by way of NMR spectral data and by mass spectral analysis. Full NMR Spectral data are given below for Compound No. 1 of Table VI. Much of the corresponding data for the other compounds were very similar as expected, therefore only characteristic signals are given. Unless otherwise stated, each compound was dissolved in CDCl$_3$ and chemical shift values are given on the delta scale.

a. NMR Spectrum 1.9(m, 4H), 2.95(s, 3H), 3.8(m, 4H), 4.9(s, 2H), 6.6–6.9(m, 3H), 7.1–7.7(m, 4H).

b. 2-Cyanophenyl iodide, used as a starting material, was obtained from 2-aminobenzonitrile using the process described in Note c. immediately below. The product was obtained in 68% yield, m.p. 52°–54° C.

c. 3-Cyanophenyl iodide, used as a starting material, was obtained as follows:

A solution of sodium nitrite (1.88 g) in water (5 ml) was added to a mixture of 3-aminobenzonitrile (2.36 g) and aqueous hydrochloric acid solution (50% w/v; 24 ml) which had been cooled in an ice-bath to a temperature in the range of 0°–5° C. The mixture was stirred at this temperature for 5 minutes. A solution of potassium iodide (4.33 g) in water (5 ml) was added and the mixture was stirred at 0°–5° C. for 30 minutes and then at ambient temperature for 2 hours. The mixture was extracted with ethyl acetate (3×25 ml). The combined extracts were washed with water, dried (MgSO4) and evaporated. The residue was purified by column chromatography to give the required starting material (2.7 g, 59%), as an oily solid.

NMR Spectrum (CDCl$_3$, delta values) 7.2(m, 1H), 7.6(m, 1H), 7.98(m, 2H).

d. NMR Spectrum 3.5(s, 3H, SO$_2$Me). 2-Methylsulphonylphenyl iodide, used as a starting material, was obtained as follows:

A solution of potassium peroxymonosulphate (5 g) in water (50 ml) was added to a mixture of 2-methylthiophenyl iodide (1.25 g) and methanol (60 ml) and the mixture was stirred at ambient temperature for 18 hours. The mixture was partitioned between methylene chloride and water. The organic phase was dried (MgSO4) and evaporated. The residue was purified by column chromatography using a 10:3 v/v mixture of hexane and ethyl acetate as eluent. There was thus obtained the required starting material (0.52 g, 37%), m.p. 110°–112° C.

e. NMR Spectrum 4.8(s, 2H, OCH$_2$CN).

f. NMR Spectrum 4.75(s, 2H, OCH$_2$CN).

g. NMR Spectrum 3.8(s, 2H, CH$_2$NH$_2$).

h. 3-(2-Cyanoprop-2-yl)phenyl iodide, used as a starting material, was obtained as follows:

A mixture of potassium cyanide (4 g) and tetra-n-butylammonium bromide (0.32 g) in water (20 ml) was added to a solution of 3-iodobenzyl bromide (5.92 g) in methylene chloride (20 ml) and the mixture was heated to reflux for 2 hours. The organic phase was separated, washed with water, dried (MgSO4) and evaporated. The residue was purified by column chromatography using methylene chloride as eluent to give 3-iodophenylacetonitrile (4.4 g).

A mixture of the product so obtained, methyl iodide (5.6 ml) and dimethylformamide (20 ml) was added dropwise to a stirred suspension of sodium hydride (60% w/w dispersion in mineral oil, 1.45 g) in dimethylformamide which had been cooled to 5° C. The mixture was stirred and allowed to warm to ambient temperature. The mixture was partitioned between ethyl acetate and water. The organic phase was washed with water, dried (MgSO4) and evaporated to give the required starting material (4.5 g) which was used without further purification.

NMR Spectrum (CDCl$_3$, delta values) 1.7(s, 6H), 7.1(t, 1H), 7.45(d, 1H), 7.65(d, 1H), 7.8(t, 1H).

i. NMR Spectrum 2.5(s, 6H, 2×CH$_3$).

j. NMR Spectrum 2.5(s, 3H, MeS).

EXAMPLE 22

The procedure described in Example 5 was repeated using the appropriate alkyl bromide and the appropriate phenol. There were thus obtained the compounds described in the following table:

TABLE VII $$Ar^1-C\equiv C-CH_2-O-Ar^2 \diagdown \bigcirc \diagup OR^1$$

| Ex. 22 Compd. No. | Ar$^1$ | Ar$^2$ | R$^1$ | m.p. (°C.) | Yield (%) |
|---|---|---|---|---|---|
| 1$^a$ | phenyl | 5-trifluoromethyl-1,3-phenylene | Me | oil | 91 |
| 2$^b$ | phenyl | 5-trifluoromethyl-1,3-phenylene | Et | oil | 91 |

NOTES a. The product displayed the following characteristic NMR signals (CDCl$_3$, delta values) 1.9–2.0(m, 4H), 2.9(s, 3H), 3.7(m, 4H), 5.2(s, 2H), 7.1–7.5(m, 8H).

The 4-(3-hydroxy-5-trifluoromethylphenyl)-4-methoxytetrahydropyran, used as a starting material, was obtained from 4-(3-benzyloxy-5-trifluoromethylphenyl)-4-hydroxytetrahydropyran using the procedures described in the 3rd and 4th paragraphs of Note e. below Table IV in Example 15 except that methyl iodide was used in place of ethyl iodide. There was thus obtained the required starting material (78%), as an oil.

NMR Spectrum (CDCl$_3$, delta values) 1.9–2.1(m, 4H), 3.0(s, 3H), 3.8–4.0(m, 4H), 5.95(s, 1H), 7.0(m, 1H), 7.1(m, 1H), 7.2(s, 1H).

b. The product displayed the following characteristic NMR signals (CDCl$_3$, delta values) 1.1–1.2(t, 3H), 1.9–2.1(m, 4H), 3.05–3.15(q, 2H), 3.8–3.9(m, 4H), 5.0(s, 2H), 7.15–7.45(m, 8H).

EXAMPLE 23

The procedure described in Example 3 was repeated using the appropriate alkyl halide and the appropriate alcohol. There was thus obtained the compounds described in the following table:

TABLE VIII $$Ar^1-CH_2-O-Ar^2 \diagdown \bigcirc \diagup OR^1$$

| Ex. 23 Compd. No. | Ar$^1$ | Ar$^2$ | R$^1$ | m.p. (°C.) | Yield (%) |
|---|---|---|---|---|---|
| 1$^a$ | 7-fluoronaphth-2-yl | 5-trifluoromethyl-1,3-phenylene | Me | 66–67 | 94 |
| 2$^b$ | 7-fluoronaphth-2-yl | 5-trifluoromethyl-1,3-phenylene | allyl | oil | 68 |
| 3$^c$ | 6,7-difluoronaphth-2-yl | 5-trifluoromethyl-1,3-phenylene | allyl | oil | 88 |

NOTES a. The 4-[3-(7-fluoronaphth-2-ylmethoxy)-5-trifluoromethylphenyl]-4-hydroxytetrahydropyran used as a starting material was obtained as follows:

4-(3-Benzyloxy-5-trifluoromethylphenyl)-4-hydroxytetrahydropyran (6 g) was hydrogenolysed using the procedure described in the 4th paragraph of Note e. below Table IV in Example 15 to give 4-hydroxy-4-(3-hydroxy-5-trifluoromethylphenyl)tetrahydropyran in quantitative yield, as an oil.

A portion (1.39 g) of the product so obtained was reacted with 2-bromomethyl-7-fluoronaphthalene (1.27 g) using the procedure described in Example 5. There was thus obtained the required starting material (2.23 g, 43%), as an oil.

NMR Spectrum (CDCl$_3$, delta values) 1.7–1.75(m, 2H), 2.05–2.25(m, 2H), 3.85–4.0(m, 4H), 5.25(s, 2H), 7.1–7.95(m, 9H).

b. The product displayed the following characterisitc NMR signals (CDCl$_3$, delta values) 1.97–2.11(m, 4H), 3.54–3.58(m, 2H), 3.84–3.95(m, 4H), 5.0–5.3(m, 2H), 5.25(s, 2H), 5.72–5.91(m, 1H), 7.18–7.89(m, 9H).

c. The product displayed the following characteristic NMR signals (CDCl$_3$, delta values) 1.85–2.10(m, 4H), 3.5–3.65(m, 2H), 3.75–4.0(m, 4H), 5.05–5.4(m, 4H), 5.7–5.9(m, 1H), 7.1–7.3(m, 3H), 7.45–7.65(m, 3H), 7.7–7.9(m, 2H).

The 4-[3-(6,7-difluoronaphth-2-ylmethoxy)-5-trifluoromethylphenyl]-4-hydroxytetrahydropyran used as a starting material was obtained using the same procedure described in Note a. above except that 2-bromomethyl-6,7-difluoronaphthalene was used in place of 2-bromomethyl-7-fluoronaphthalene.

EXAMPLE 24

4-Hydroxy-4-[5-nitro-3-(3-phenylprop-2-ynyloxy)phenyl]-tetrahydropyran was alkylated with methyl iodide using the procedure described in Example 1 except that no 15-crown-5 was added. There was thus obtained 4-methoxy-4-[5-nitro-3-(3-phenylprop-2-ynyloxy)phenyl]tetrahydropyran (72%), m.p. 112°–113° C.

The 4-hydroxy-4-[5-nitro-3-(3-phenylprop-2-ynyloxy)phenyl]tetrahydropyran, used as a starting material was obtained as follows:

A solution of 3-phenylprop-2-yn-1-ol (19 g) in dimethylacetamide (100 ml) was added to a stirred suspension of sodium hydride (50% w/w dispersion in mineral oil, 7.5 g) in dimethylacetamide (320 ml) and the mixture was stirred at ambient temperature for 1 hour. 1-Iodo-3,5-dinitrobenzene (42 g; *J. Chem. Soc.* (C), 1970, 1480) was added to the mixture portionwise and the resultant mixture was stirred at ambient temperature for 2 hours. The mixture was partitioned between diethyl ether and 2N aqueous hydrochloric acid solution. The organic phase was washed with water, dried (MgSO$_4$) and evaporated. The residue was purified by column chromatography using increasingly polar mixtures of petroleum ether (b.p. 40°–60° C.) and methylene chloride as eluent. There was thus obtained 5-nitro-3-(3-phenylprop-2-ynyloxy)phenyl iodide (31 g, 58%), as an oil.

NMR Spectrum (CD$_3$SOCD$_3$, delta values) 5.25(s, 2H), 7.45(s, 5H), 7.9(m, 2H), 8.15(m, 1H).

A solution of a portion (2.6 g) of the product so obtained in tetrahydrofuran (100 ml) was cooled to −105° C. and n-butyl-lithium (1.2M in toluene; 4.3 ml) was added dropwise. The mixture was stirred at −100° C. for 10 minutes then tetrahydropyran-4-one (0.63 ml) was added dropwise. The mixture was stirred at −100° C. for 20 minutes and then allowed to warm to ambient temperature. The mixture was partitioned between diethyl ether and 2N aqueous hydrochloric acid solution. The organic phase was washed with water, dried (MgSO$_4$) and evaporated. The residue was purified by column chromatography using a 1:1 v/v mixture of petroleum ether (b.p. 40°–60° C.) and diethyl ether as eluent. There was thus obtained the required starting material (2.2 g, 65%), as an oil.

NMR Spectrum (CDCl$_3$, delta values) 1.5-2.5(m, 5H), 3.75-4.0(m, 4H), 5.0(s, 2H), 7.2-7.6(m, 6H), 7.8(m, 1H), 8.0(m, 1H).

EXAMPLE 25

A mixture of 4-methoxy-4-[5-nitro-3-(3-phenylprop-2-ynyloxy)phenyl]tetrahydropyran (0.3 g), activated iron (1.5 g; obtained by stirring a mixture of iron powder and 2N hydrochloric acid solution for 10 minutes, filtering the mixture and washing and drying the solid), ferrous sulphate heptahydrate (0.15 g), water (4.5 ml) and methanol (21 ml) was stirred vigorously and heated to 80° C. for 45 minutes. The mixture was filtered and the filtrate was evaporated. The residue was purified by column chromatography using diethyl ether as eluent. There was thus obtained 4-[5-amino-3-(3-phenylprop-2-ynyloxy)phenyl]-4-methoxytetrahydropyran (0.23 g, 84%), as an oil.

NMR Spectrum (CDCl$_3$, delta values) 1.94(m, 4H), 3.0(s, 3H), 3.8(m, 4H), 4.9(s, 2H), 6.35(m, 2H), 6.5(m, 1H), 7.35(m, 5H).

EXAMPLE 26

Sodium cyanoborohydride (0.56 g) was added portionwise to a mixture of 4-[5-amino-3-(3-phenylprop-2-ynyloxy)phenyl]-4-methoxytetrahydropyran (1 g), formaldehyde (2.5 ml of a 37% w/v solution in water) and acetonitrile (30 ml). The mixture was stirred at ambient temperature for 15 minutes. Acetic acid (1 ml) was added and the mixture was stirred for 2 hours. The mixture was partitioned between diethyl ether and water. The organic phase was separated, washed with 1N aqueous potassium hydroxide solution and with water, dried (MgSO$_4$) and evaporated. The residue was purified by column chromatography using diethyl ether as eluent. There was thus obtained 4-[5-dimethylamino-3-(3-phenylprop-2-ynyloxy)phenyl]-4-methoxytetrahydropyran (0.87 g, 80%), as an oil.

NMR Spectrum (CDCl$_3$, delta values) 2.0(m, 4H), 2.95(s, 6H), 3.0(s, 3H), 3.75-4.0(m, 4H), 4.9(s, 2H), 6.3-6.5(m, 3H), 7.2-7.55(m, 5H).

EXAMPLE 27

Sodium cyanate (0.17 g) was added portionwise to a mixture of 4-[5-amino-3-(3-phenylprop-2-ynyloxy)phenyl]-4-methoxytetrahydropyran (0.5 g), 2N hydrochloric acid solution (1 ml), water (2.5 ml) and ethanol (2.5 ml) and the mixture was stirred at ambient temperature for 15 hours. The mixture was extracted with methylene chloride. The organic phase was dried (MgSO$_4$) and evaporated. The residue was triturated under a mixture of dichloromethane and diethyl ether. There was thus obtained 4-methoxy-4-[3-(3-phenylprop-2-ynyloxy)-5-ureidophenyl]tetrahydropyran (0.38 g, 67%), m.p. 164°-165° C.

EXAMPLE 28

Acetyl chloride (0.127 ml) was added to a mixture of 4-[5-amino-3-(3-phenylprop-2-ynyloxy)phenyl]-4-methoxytetrahydropyran (0.5 g), triethylamine (0.25 ml) and methylene chloride (10 ml) which had been cooled to 0° C. and the mixture was stirred at ambient temperature for 2 hours. The mixture was partitioned between diethyl ether and water. The organic phase was dried (MgSO$_4$) and evaporated. The residue was purified by column chromatography using diethyl ether as eluent. There was thus obtained 4-[5-acetamido-3-(3-phenylprop-2-ynyloxy)phenyl]-4-methoxytetrahydropyran (0.46 g, 83%), as an oil.

NMR Spectrum (CDCl$_3$, delta values) 2.0(m, 4H), 2.2(s, 3H), 3.0(s, 3H), 3.7-3.95(m, 4H), 4.95(s, 2H), 6.85(m, 1H), 7.0(m, 1H), 7.15-7.55(m, 6H).

EXAMPLE 29

A mixture of 4-[5-amino-3-(3-phenylprop-2-ynyloxy)phenyl]-4-methoxytetrahydropyran (1 g), bromoacetonitrile (0.4 ml), potassium carbonate (0.49 g) and dimethylformamide (10 ml) was heated to 60° C. for 3 hours and to 80° for 2 hours. The mixture was cooled to ambient temperature and partitioned between diethyl ether and water. The organic phase was dried (MgSO$_4$) and evaporated. The residue was purified by column chromatography using a 3:1 v/v mixture of toluene and ethyl acetate as eluent. There was thus obtained 4-[5-cyanomethylamino-3-(3-phenylprop-2-ynyloxy)phenyl]-4-methoxytetrahydropyran (0.9 g, 81%), as an oil.

NMR Spectrum (CDCl$_3$, delta values) 2.0(m, 4H), 3.0(s, 3H), 3.85(m, 4H), 4.1(s, 2H), 4.9(s, 2H), 6.35(m, 1H), 6.4(m, 1H), 6.65(m, 1H), 7.1-7.6(m, 5H).

EXAMPLE 30

The procedure described in Example 29 was repeated except that ethyl bromoacetate was used in place of bromoacetonitrile and that the mixture was stirred at ambient temperature for 12 hours. There was thus obtained 4-[5-ethoxycarbonylmethylamino-3-(3-phenylprop-2-ynyloxy)phenyl]-4-methoxytetrahydropyran (1.16 g, 92%), as an oil.

NMR Spectrum (CDCl$_3$, delta values) 1.29(t, 3H), 1.95(m, 4H), 2.99(s, 3H), 3.7-4.0(m, 6H), 4.25(q, 2H), 4.9(s, 2H), 6.25(m, 1H), 6.35(m, 1H), 6.55(m, 1H), 7.1-7.6(m, 5H).

EXAMPLE 31

A mixture of 4-[5-ethoxycarbonylmethylamino-3-(3-phenylprop-2-ynyloxy)phenyl]-4-methoxytetrahydropyran (0.4 g), 2N aqueous sodium hydroxide solution (2 ml) and methanol (2 ml) was stirred at ambient temperature for 2 hours. The mixture was cooled to 0° C. and acidified by the addition of 2N aqueous hydrochloric acid solution. The mixture was extracted with diethyl ether. The organic phase was dried (MgSO$_4$) and evaporated. The residue was purified by column chromatography using a 49:1 v/v mixture of methylene chloride and methanol as eluent. There was thus obtained 4-[5-carboxymethylamino-3-(3-phenylprop-2-ynyloxy)phenyl]-4-methoxytetrahydropyran (0.22 g, 59%), as an oil.

NMR Spectrum (CDCl$_3$, delta values) 2.0(m, 4H), 3.0(s, 3H), 3.6-4.1(m, 6H), 4.9(s, 2H), 5.4(m, 2H), 6.15-6.45(m, 2H), 6.5(m, 1H), 7.1-7.6(m, 5H).

EXAMPLE 32

Lithium aluminium hydride (0.03 g) was added portionwise to a solution of 4-[5-ethoxycarbonylmethylamino-3-(3-phenylprop-2-ynyloxy)phenyl]-4-methoxytetrahydropyran (0.5 g) in diethyl ether (10 ml) which had been cooled to 0° C. and the mixture was stirred at 0° C. for 30 minutes. Ice was added portionwise to hydrolyse the excess of reducing agent. The organic phase was separated, dried (MgSO$_4$) and evaporated. The residue was purified by column chromatography using a 4:1 v/v mixture of toluene and ethyl acetate as eluent. There was thus obtained 4-[5-(2-hydroxyethyl)amino-3-(3-phenylprop-2-ynyloxy)phenyl]-4-methoxytetrahydropyran (0.33 g, 73%), as an oil.

NMR Spectrum (CDCl$_3$, delta values) 1.94(m, 4H), 3.0(s, 3H), 3.3(t, 2H), 3.6-4.0(m, 6H), 4.9(s, 2H), 6.2-6.45(m, 2H), 6.5(m, 1H), 7.1-7.55(m, 5H).

EXAMPLE 33

A mixture of 4-(3,5-dihydroxyphenyl)-4-methoxytetrahydropyran (4.75 g), 3-phenylprop-2-ynyl bromide (4.2 g), potassium carbonate (2.92 g) and dimethylformamide (50 ml) was stirred at ambient temperature for 12 hours. The mixture was acidified by the addition of 2N hydrochloric acid solution and extracted with diethyl ether. The organic extract was dried (MgSO$_4$) and evaporated. The residue was purified by column chromatography using a 4:1 v/v mixture of toluene and ethyl acetate as eluent. There was thus obtained 4-[5-hydroxy-3-(3-phenylprop-2-ynyloxy)phenyl]-4-methoxytetrahydropyran (1.92 g, 27%), m.p. 141°-142° C.

The 4-(3,5-dihydroxyphenyl)-4-methoxytetrahydropyran, used as a starting material, was obtained as follows:

3,5-Dihydroxyphenyl iodide (*Tex. J. Sci.*, 1977, 28, 253) was reacted with two equivalents of benzyl bromide using the procedure described in Example 3 to give 3,5-dibenzyloxyphenyl iodide (96%), as an oil. This was reacted with n-butyl-lithium using the procedure described in the portion of Example 24 which is concerned with the preparation of starting materials and the organometallic reagent so formed was reacted with tetrahydropyran-4-one using the procedure described in that Example. There was thus obtained 4-(3,5-dibenzyloxyphenyl)-4-hydroxytetrahydropyran (60%), as an oil.

NMR Spectrum (CDCl$_3$, delta values) 1.5-2.4(m, 4H), 3.75-4.0(m, 4H), 5.05(s, 4H), 6.55(d of d's, 1H), 6.75(d, 2H), 7.4(m, 10H).

The product so obtained was methylated using the procedure described in Example 1. There was thus obtained 4-(3,5-dibenzyloxyphenyl)-4-methoxytetrahydropyran (75%), as an oil.

NMR Spectrum (CDCl$_3$, delta values) 1.7-2.0(m, 4H), 2.35(s, 3H), 3.5-3.8(m, 4H), 5.1(s, 4H), 6.7(s, 3H), 7.2-7.6(m, 10H).

The product so obtained was hydrogenolysed using the procedure described in the portion of Example 5 which is concerned with the preparation of starting materials. There was thus obtained the required starting material (90%), as an oil.

NMR Spectrum (CDCl$_3$, delta values) 1.7-2.0(m, 4H), 2.3(s, 3H), 3.5-3.8(m, 4H), 6.1-6.4(m, 3H).

EXAMPLE 34

4-[5-Hydroxy-3-(3-phenylprop-2-ynyloxy)phenyl]-4-methoxytetrahydropyran was reacted with methyl iodide using the procedure described in Example 5. There was thus obtained 4-methoxy-4-[5-methoxy-3-(3-phenylprop-2-ynyloxy)phenyl]tetrahydropyran (85%), as an oil.

NMR Spectrum (CDCl$_3$, delta values) 1.95(m, 4H), 3.0(s, 3H), 3.8(m, 7H), 4.9(s, 2H), 6.5-6.75(m, 3H), 7.2-7.6(m, 5H).

EXAMPLE 35

The procedure described in Example 34 was repeated except that bromoacetonitrile was used in place of methyl iodide and the reaction mixture was heated to 60° C. for 4 hours. There was thus obtained 4-[5-cyanomethoxy-3-(3-phenylprop-2-ynyloxy)phenyl]-4-methoxytetrahydropyran (45%), as an oil.

NMR Spectrum (CDCl$_3$, delta values) 1.95(m, 4H), 3.0(s, 3H), 3.9(m, 4H), 4.8(s, 2H), 5.0(s, 2H), 6.65-6.75(m, 2H), 6.9(m, 1H), 7.2-7.6(m, 5H).

EXAMPLE 36

4-Hydroxy-4-[5-(3-phenylprop-2-ynyloxy)pyrid-3-yl]tetrahydropyran was alkylated with methyl iodide using the procedure described in Example 1. There was thus obtained 4-methoxy-4-[5-(3-phenylprop-2-ynyloxy)pyrid-3-yl]tetrahydropyran (62%), as an oil.

NMR Spectrum (CDCl$_3$, delta values) 1.8-2.25(m, 4H), 3.0(s, 3H), 3.75-4.1(m, 4H), 4.98(s, 2H), 7.25-7.6(m, 6H), 8.25-8.5(m, 2H).

The 4-hydroxy-4-[5-(3-phenylprop-2-ynyloxy)pyrid-3-yl]tetrahydropyran, used as a starting material, was obtained as follows:

3-Phenylprop-2-ynyl bromide (0.195 g) was added dropwise to a mixture of 3-bromo-5-hydroxypyridine (0.174 g; UK Patent Applic. No. 2025953), potassium carbonate (0.14 g) and dimethylformamide (5 ml) which had been cooled to −15° C. The mixture was stirred at −15° C. for 24 hours. The mixture was partitioned between ethyl acetate and a saturated aqueous ammonium chloride solution. The organic phase was dried (MgSO$_4$) and evaporated. The residue was purified by column chromatography using methylene chloride as eluent. There was thus obtained 3-bromo-5-(3-phenylprop-2-ynyloxy)pyridine (0.14 g, 49%), as an oil.

NMR Spectrum (CDCl$_3$, delta values) 4.95(s, 2H), 7.25-8.1(m, 6H), 8.25-8.5(m, 2H).

After appropriate repetition of the above reaction the product so obtained was treated as follows:

n-Butyl-lithium (1.6M in hexane, 6.5 ml) was added dropwise to a solution of the product so obtained (2.88 g) in tetrahydrofuran (130 ml) which had been cooled to −110° C. The mixture was stirred at this temperature for 10 minutes and then tetrahydropyran-4-one (1 g) was added dropwise. The mixture was allowed to warm to −10° C. over a period of 1 hour. The mixture was partitioned between diethyl ether and a saturated aqueous ammonium chloride solution. The organic phase was dried (MgSO$_4$) and evaporated and the residue was purified by column chromatography using 50:50:1 v/v mixture of methylene chloride, diethyl ether and methanol as eluent. There was thus obtained the required starting material (1.12 g, 36%), m.p. 198°-200° C.

EXAMPLE 37

Sodium hydride (50% w/w dispersion in mineral oil, 0.048 g) was added to a solution of 4-hydroxy-4-[3-(naphth-2-ylmethoxy)pyridazin-5-yl]tetrahydropyran (0.34 g) in dimethylformamide (12 ml) which had been cooled to −20° C. and the mixture was stirred at this temperature for 1 hour. Methyl iodide (0.142 g) was added and the mixture was stirred at −20° C. for 1 hour. The mixture was partitioned between diethyl ether and water. The organic phase was dried (MgSO$_4$) and evaporated and the residue was purified by column chromatography using a 50:50:1 v/v mixture of methylene chloride, diethyl ether and methanol as eluent. There was thus obtained 4-methoxy-4-[3-(naphth-2-ylmethoxy)pyridazin-5-yl]tetrahydropyran (0.27 g, 77%), m.p. 90°-91° C.

The 4-hydroxy-4-[3-naphth-2-ylmethoxy)pyridazin-5-yl]tetrahydropyran used as a starting material was obtained as follows:

A mixture of 2-bromomethylnaphthalene (0.44 g), 5-bromo-3-hydroxypyridazine (0.175 g; Spanish Patent Application No. 454136), silver carbonate (0.167 g) and benzene (5 ml) was stirred at ambient temperature for 72 hours. The mixture was filtered and the filtrate was evaporated. The residue was purified by column chromatography using methylene chloride as eluent. There was thus obtained 5-bromo-3-(naphth-2-ylmethoxy)-pyridazine (0.165 g, 52%).

The product so obtained was reacted with tetrahydropyran-4-one using the procedure described in the second paragraph of the portion of Example 36 which is concerned with the preparation of starting materials. There was thus obtained the required starting material (52%), as an oil.

NMR Spectrum (CDCl$_3$, delta values) 1.5-2.25(m, 4H), 3.5-4.0(m, 4H), 5.6(s, 2H), 7.1(s, 1H), 7.25-8.0(m, 7H), 9.0(m, 1H).

EXAMPLE 38

Sodium periodate (0.426 g) was added to a stirred suspension of 4-[5-fluoro-3-(4-methylthiobenzyloxy)-phenyl-4-methoxytetrahydropyran (0.6 g), methanol (30 ml) and water (2 ml) which had been cooled to 0° C. The mixture was allowed to warm to ambient temperature and was stirred for 64 hours. The mixture was partitioned between ethyl acetate and water. The organic phase was washed with a saturated aqueous sodium chloride solution, dried (MgSO$_4$) and evaporated. The residue was purified by column chromatography using ethyl acetate as eluent. There was thus obtained 4-[5-fluoro-3-(4-methylsulphinylbenzyloxy)phenyl]-4-methoxytetrahydropyran (0.44 g, 70%), m.p. 104°-105° C.

EXAMPLE 39

A solution of potassium peroxymonosulphate (2 g) in water (10 ml) was added to a mixture of 4-[5-fluoro-3-(4-methylthiobenzyloxy)phenyl]-4-methoxytetrahydropyran (0.87 g), methanol (25 ml) and tetrahydrofuran (15 ml) and the cloudy mixture was stirred at ambient temperature for 16 hours. The mixture was partitioned between ethyl acetate and water. The organic phase was washed with a saturated aqueous sodium chloride solution, dried (MgSO$_4$) and evaporated. The residual solid was dissolved in ethyl acetate and precipitated by the addition of petroleum ether (b.p. 60°-80° C.). There was thus obtained 4-[5-fluoro-3-(4-methylsulphonylbenzyloxy)phenyl]-4-methoxytetrahydropyran (0.53 g, 62%), m.p. 123°-124° C.

EXAMPLE 40

A mixture of 4-[3-(3-(3-aminophenyl)prop-2-ynyloxy)-5-fluorophenyl]-4-methoxytetrahydropyran (0.21 g), acetic anhydride (1.5 ml) and pyridine (1.5 ml) was allowed to stand at ambient temperature for 16 hours. The mixture was partitioned between ethyl acetate and water. The organic phase was washed with water, dried (MgSO$_4$) and evaporated. The residue was purified by column chromatography using a 1:2 v/v mixture of hexane and ethyl acetate as eluent. There was thus obtained 4-[3-(3-(3-acetamidophenyl)prop-2-ynyloxy)-5-fluorophenyl]-4-methoxytetrahydropyran (0.14 g, 59%), m.p. 124°-126° C.

EXAMPLE 41

A mixture of 4-hydroxy-4-(4-(naphth-2-ylmethoxy)-phenyl)tetrahydropyran (0.39 g), powdered potassium hydroxide (0.262 g), methyl iodide (0.332 g) and dimethylsulphoxide (10 ml) was stirred at ambient temperature for 15 hours. The mixture was evaporated and the residue was purified by column chromatography using a 97:3 v/v mixture of methylene chloride and methanol as eluent. There was thus obtained 4-methoxy-4-(4-(naphth-2-ylmethoxy)phenyl)tetrahydropyran (0.18 g, 27%), m.p. 135°-136° C.

The 4-hydroxy-4-(4-naphth-2-ylmethoxy)phenyl)tetrahydropyran, used as a starting material, was obtained as follows:

Using the procedure described in Example 5, 2-bromomethylnaphthalene was reacted with 4-bromophenol to give 4-(naphth-2-ylmethoxy)bromobenzene (99%), m.p. 104°-106° C.

Using the procedure described in the 2nd paragraph of the portion of Example 3 which is concerned with the preparation of starting materials, the product obtained above was reacted with tetrahydropyran-4-one to give the required starting material (29%), m.p. 166°-168° C.

EXAMPLE 42

Using the procedure described in Example 3, 4-hydroxy-4-(3-methoxy-4-(naphth-2-ylmethoxy)phenyl)-tetrahydropyran (0.5 g) was reacted with methyl iodide (2 ml) to give 4-methoxy-4-(3-methoxy-4-(naphth-2-ylmethoxy)phenyl)tetrahydropyran (0.27 g, 52%), m.p. 129° C. (recrystallised from ethyl acetate).

The 4-hydroxy-4-(3-methoxy-4-(naphth-2-ylmethoxy)phenyltetrahydropyran used as a starting material was obtained as follows:

Using the procedure described in Example 5, 2-bromomethylnaphthalene was reacted with 4-bromo-2-methoxyphenol to give 3-methoxy-4-(naphth-2-ylmethoxy)bromobenzene (62%), m.p. 108° C.

Using the procedure described in the 2nd paragraph of the portion of Example 3 which is concerned with the preparation of starting materials, the product obtained above was reacted with tetrahydropyran-4-one to give the required starting material (44%), m.p. 150°-151° C. (recrystallised from ethyl acetate).

EXAMPLE 43

Using the procedure described in Example 1, except that no 15-crown-5 was used, 4-(3-cyano-4-(naphth-2-ylmethoxy)phenyl)-4-hydroxytetrahydropyran (0.18 g) was reacted with methyl iodide. There was thus obtained 4-(3-cyano-4-(naphth-2-ylmethoxy)phenyl)-4-methoxytetrahydropyran (0.11 g, 59%), m.p. 161°-164° C. [recrystallised from a mixture of petroleum ether (b.p. 60°-80° C.) and methylene chloride].

The 4-(3-cyano-4-(naphth-2-ylmethoxy)phenyl-4-hydroxytetrahydropyran, used as a starting material, was obtained as follows:

Using the procedure described in Example 5, 2-bromomethylnaphthalene was reacted with methyl 5-iodosalicylate to give methyl 5-iodo-2-(naphth-2-ylmethoxy)benzoate (68%). Using conventional procedures the ester was hydrolysed with base to give the corresponding acid; the acid chloride was prepared by reaction with oxalyl chloride; and the acid chloride was reacted with ethanolic ammonia to give 5-iodo-2-(naphth-2-ylmethoxy)benzamide (84% from the ester), m.p. 163° C. The benzamide so obtained was reacted with trifluoroacetic anhydride in the presence of pyridine and dimethoxyethane as reaction solvent. There was thus obtained 3-cyano-4-(naphth-2-ylmethoxy)phenyl iodide (72%), m.p. 108°-110° C.

Using the procedure described in the 2nd paragraph of the portion of Example 24 which is concerned with the preparation of starting materials, the iodide so obtained (0.77 g) was reacted with tetrahydropyran-4-one (0.2 ml) to give the required starting material (0.18 g, 25%), m.p. 144°-145° C.

EXAMPLE 44

The procedure described in Example 3 was repeated using the appropriate alkyl halide and the appropriate alcohol. There were thus obtained the compounds described in the following table:

the 2-methyl and 4-hydroxy substituents are in a trans relationship,

NMR Spectrum (CDCl$_3$, delta values) 1.2(d, 3H), 1.5-2.2(m, 4H), 3.9-4.0(m, 3H), 5.25(s, 2H), 6.9-7.9(m, 11H); and a more polar isomer, (2SR,4SR)-4-hydroxy-2-methyl-4-[3-(naphth-2-ylmethoxy)phenyl]tetrahydropyran (0.8 g, 23%), as an oil, i.e. the 2-methyl and 4-hydroxy substituents are in a cis-relationship, NMR Spectrum (CDCl$_3$, delta values) 1.2(d, 3H), 1.5-2.4(m, 4H), 3.4(m, 2H), 3.9(m, 1H), 5.25(s, 2H), 6.9-7.9(m, 11H).

b. The product displayed the following characteristic NMR signals (CDCl$_3$, delta values) 1.2(d, 3H), 1.6-2.4(m, 4H), 2.85(s, 3H), 3.4(m, 2H), 3.9(m, 1H),

TABLE IX

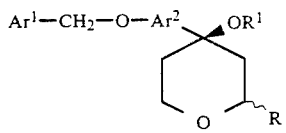

| Ex. 44 Compd. No. | Ar$^1$ | Ar$^2$ | R$^1$ | R | m.p. (°C.) | Yield (%) |
|---|---|---|---|---|---|---|
| 1$^a$ | 2-naphthyl | 1,3-phenylene | Me | alpha-Me | 48-50 | 30 |
| 2$^b$ | 2-naphthyl | 1,3-phenylene | Me | beta-Me | oil | 72 |
| 3$^c$ | 2-naphthyl | 1,3-phenylene | allyl | alpha-Me | oil | 13 |
| 4$^d$ | 2-naphthyl | 5-fluoro-1,3-phenylene | Me | alpha-Me | oil | 42 |
| 5$^e$ | 2-naphthyl | 5-fluoro-1,3-phenylene | Me | beta-Me | oil | 57 |
| 6$^f$ | 2-naphthyl | 5-fluoro-1,3-phenylene | allyl | alpha-Me | oil | 55 |
| 7$^g$ | 2-naphthyl | 5-fluoro-1,3-phenylene | allyl | beta-Me | oil | 48 |
| 8$^h$ | 2-naphthyl | 5-trifluoro-methyl-1,3-phenylene | Me | alpha-Me | oil | 66 |
| 9$^i$ | 2-naphthyl | 5-trifluoro-methyl-1,3-phenylene | Me | beta-Me | oil | 47 |
| 10$^j$ | 2-naphthyl | 5-trifluoro-methyl-1,3-phenylene | Et | beta-Me | oil | 68 |
| 11$^k$ | 7-fluoronaphth-2-yl | 1,3-phenylene | allyl | alpha-Me | oil | 55 |
| 12$^l$ | 6,7-difluoro-naphth-2-yl | 1,3-phenylene | allyl | alpha-Me | oil | 59 |
| 13$^m$ | 2-naphthyl | 5-fluoro-1,3-phenylene | Et | alpha-Me | oil | 33 |

NOTES a. Methyl iodide was used as the alkylating agent.

The (2RS,4SR)-4-hydroxy-2-methyl-4-[3-(naphth-2-ylmethoxy)phenyl]tetrahydropyran, used as a starting material, was obtained as follows:

A solution of n-butyl-lithium (1.6M in hexane, 6.25 ml) was added to a solution of 3-(naphth-2-ylmethoxy)-bromobenzene (3.13 g) in tetrahydrofuran (60 ml) which had been cooled to −70° C. and the mixture was stirred at this temperature for 5 minutes. Magnesium bromide (25 ml of a 0.5M solution in a 1:1 v/v mixture of toluene and diethyl ether; prepared as described in J. Org. Chem., 1979, 44, 3280) was added and the mixture was stirred at −70° C. for 5 minutes. A solution of 2-methyltetrahydropyran-4-one (1.14 g) in tetrahydrofuran (5 ml) was added and the mixture was stirred at −70° C. for 10 minutes and then allowed to warm to ambient temperature. The mixture was concentrated to approxmately one third of the original volume and poured into water (300 ml). The mixture was neutralised by the addition of 2N hydrochloric acid solution and extracted with diethyl ether (2×150 ml). The combined extracts were washed with water and with a saturated aqueous sodium chloride solution, dried (MgSO$_4$) and evaporated. The residue, containing a mixture of diastereoisomers, was purified and the isomers were separated by column chromatography using a 2:1 v/v mixture of hexane and ethyl acetate as eluent.

There were thus obtained: a less polar isomer, (2RS,4SR)-4-hydroxy-2-methyl-4-[3-(naphth-2-ylmethoxy)phenyl]tetrahydropyran (1 g, 29%), as an oil, i.e.

5.25(s, 2H), 6.9-7.9(m, 11H).

The (2SR,4SR)-isomer, described in Note a. above, was used as the required starting material.

c. Allyl bromide was used as the alkylating agent, potassium hydroxide as the base and dimethylsulphoxide as the solvent, and the procedure described in the 3rd paragraph of the portion of Note e. below Table IV in Example 15 was utilised. The product displayed the following characteristic NMR signals (CDCl$_3$, delta values) 1.2(d, 3H), 1.5-2.0(m, 4H), 3.6(m, 2H), 3.9(m, 3H), 5.2(m, 4H), 5.8(m, 1H), 6.8-7.9(m, 11H).

d. Methyl iodide was used as the alkylating agent. The product displayed the following characteristic NMR signals (CDCl$_3$, delta values) 1.2(m, 3H), 1.5-1.9(m, 4H), 2.94(s, 3H), 3.8(m, 3H), 5.2(s, 2H), 6.6-7.8(m, 10H).

The (2RS,4SR)-4-[5-fluoro-3-(naphth-2-ylmethoxy)-phenyl]-4-hydroxy-2-methyltetrahydropyran, used as a starting material, was obtained as follows:

Using the procedure described in the first paragraph of the portion of Example 3 which is concerned with the preparation of starting materials, 2-naphthalenemethanol was reacted with 1-bromo-3,5-difluorobenzene to give 5-fluoro-3-(naphth-2-ylmethoxy)bromobenzene (92%), m.p. 65°-67° C.

Using the procedure described in Note a. above, the product so obtained was reacted with 2-methyltetrahydropyran-4-one to give a less polar isomer, (2RS,4SR)-4-[5-fluoro-3-(naphth-2-ylmethoxy)phenyl]-4-hydroxy-2-methyltetrahydropyran (44%), as an oil, NMR Spectrum (CDCl$_3$, delta values) 1.2 (d, 3H), 1.4-1.6(m, 4H), 3.85(m, 3H), 5.2(s, 2H), 6.6-7.8(m, 10H); and a more polar isomer, the corresponding (2SR,4SR)-isomer (29%), as an oil.

NMR Spectrum (CDCl$_3$, delta values) 1.1(d, 3H), 1.6(m, 2H), 2.2(m, 2H), 3.3(m, 2H), 3.85(m, 1H), 5.2(s, 2H), 6.6–7.8(m, 10H).

e. The product displayed the following characteristic NMR signals (CDCl$_3$, delta values) 1.13(d, 3H), 1.6(m, 2H), 2.28(m, 2H), 2.88(s, 3H), 3.36(m, 2H), 3.94(m, 1H), 5.2(s, 2H), 6.7–7.8(m, 10H).

The (2SR,4SR-isomer, described in Note d. above, was used as the required starting material.

f. Allyl bromide was used as the alkylating agent. The product displayed the following characteristic NMR signals (CDCl$_3$, delta values) 1.2(m, 3H), 1.5–1.9(m, 4H), 3.6(m, 2H), 3.9(m, 3H), 5.2(m, 4H), 5.8(m, 1H), 6.6–7.8(m, 10H).

g. Allyl bromide was used as the alkylating agent and the (2SR,4SR)-isomer, described in Note d. above, was used as the alcohol. The product displayed the following NMR signals (CDCl$_3$, delta values) 1.2(m, 3H), 1.7–1.9(m, 2H), 2.3(m, 2H), 3.4(m, 2H), 3.55(m, 2H), 3.94(m, 1H), 5.1(m, 2H), 5.2(s, 2H), 5.7(m, 1H), 6.7–7.9(m, 10H).

h. Methyl iodide was used as the alkylating agent. The product displayed the following NMR signals (CDCl$_3$, delta values) 1.2(m, 3H), 1.5–1.9(m, 4H), 2.95(s, 3H), 3.8(m, 3H), 5.2(s, 2H), 7.2–7.8(m, 10H).

The (2RS,4SR)-4-hydroxy-2-methyl-4-[3-(naphth-2-ylmethoxy)-5-trifluoromethylphenyl]tetrahydropyran used as a starting material was obtained as follows:

Using the procedure described in the first paragraph of Note e. below Table IV in Example 15, 2-naphthalenemethanol was reacted with 3-fluoro-5-trifluoromethylbromobenzene to give 3-(naphth-2-ylmethoxy)-5-trifluoromethylbromobenzene (80%), m.p. 68°–70° C.

Using the procedure described in Note a. above, the product so obtained was reacted with 2-methyltetrahydropyran-4-one to give a less polar isomer, (2RS,4SR)-4-hydroxy-2-methyl-4-[3-(naphth-2-ylmethoxy)-5-trifluoromethylphenyl]tetrahydropyran (18%), as an oil; and a more polar isomer, the corresponding (2SR,4SR)-isomer (12%), as an oil.

i. The product displayed the following characterisitc NMR signals (CDCl$_3$, delta values) 1.1(d, 3H), 1.6(m, 2H), 2.3(m, 2H), 2.9(s, 3H), 3.4(m, 2H), 3.9(m, 1H), 5.2(s, 2H), 7.2–7.8(m, 10H).

j. Ethyl iodide was used as the alkylating agent. The product displayed the following characteristic NMR signals (CDCl$_3$, delta values) 0.9(t, 3H), 1.1(d, 3H), 1.6–1.9(m, 2H), 2.3(m, 2H), 3.0(q, 2H), 3.4(m, 2H), 3.9(m, 1H), 5.2(s, 2H), 7.2–7.8(m, 10H).

k. Allyl bromide was used as the alkylating agent. The product displayed the following characteristic NMR signals (CDCl$_3$, delta values) 1.2(d, 3H), 1.6(m, 1H), 2.0(m, 3H), 3.6(m, 2H), 3.95–4.1(m, 3H), 5.1(m, 1H), 5.2–5.3(m, 3H), 5.8(m, 1H), 6.9–7.9(m, 10H).

The (2RS,4SR)-4-[3-(7-fluoronaphth-2-ylmethoxy)phenyl]-4-hydroxy-2-methyltetrahydropyran, used as a starting material, was obtained as follows:

Using the procedure described in Exampe 5, 3-bromophenol was reacted with benzyl bromide to give 3-benzyloxybromobenzene (97%), as a white solid.

Using the procedure described in the portion of Example 1 which is concerned with the preparation of starting materials, a Grignard reagent was prepared from 3-benzyloxybromobenzene (10.5 g) and 2-methyltetrahydropyran-4-one (2.28 g) was added. The mixture was stirred at ambient temperature for 3 hours, acidified by the addition of 2N hydrochloric acid solution and extracted with ethyl acetate. Column chromatography, using a 10:3 v/v mixture of toluene and ethyl acetate as eluent, gave a less polar isomer, (2RS,4SR)-4-(3-benzyloxyphenyl)-4-hydroxy-2-methyltetrahydropyran (2.45 g, 41%), as an oil, NMR Spectrum (CDCl$_3$, delta values) 1.2(d, 3H), 1.6–1.8(m, 4H),2.0–2.2(m, 1H), 3.9–4.1(m, 3H), 5.1(s, 2H), 6.85–7.45(m, 9H); and a more polar isomer, (2SR,4SR)-4-(3-benzyloxyphenyl)-4-hydroxy-2-methyltetrahydropyran (1.38 g, 23%), as an oil, NMR Spectrum (CDCl$_3$, delta values) 1.2(d, 3H), 1.6–2.05(m, 4H), 2.3–2.45(m, 1H), 3.3–3.5(m, 2H), 3.9–4.0(m, 1H), 5.1(s, 2H), 6.9–7.5(m, 9H).

After repetition of the above steps, a mixture of the (2RS,4SR)-isomer (5.1 g), 10% palladium-on-charcoal catalyst (0.5 g) and ethanol (100 ml) was stirred under an atmosphere of hydrogen for 15 hours. The mixture was filtered and the filtrate was evaporated. There was thus obtained (2RS,4SR)-4-hydroxy-4-(3-hydroxyphenyl)-2-methyltetrahydropyran (3 g, 84%), as a white solid.

Using the procedure described in Example 5, a portion (0.6 g) of the product so obtained was reacted with 2-bromomethyl-7-fluoronaphthalene (0.76 g) to give the required starting material (0.83 g, 79%), as an oil.

NMR Spectrum (CDCl$_3$, delta values) 1.2(d, 3H), 1.6–1.75(m, 4H), 2.05–2.2(m, 1H), 4.0(m, 3H), 5.25(s, 2H), 6.9–7.9(m, 10H).

l. Allyl bromide was used as the alkylating agent. The product displayed the following characteristic NMR signals (CDCl$_3$, delta values) 1.15(d, 3H), 1.6–2.05(m, 4H), 3.6(m, 2H), 3.85–4.1(m, 3H), 5.05–5.3 (m, 4H), 5.75–5.95(m, 1H), 6.9–7.9(m, 9H).

The (2RS,4SR)-4-[3-(6,7-difluoronaphth-2-ylmethoxy)phenyl]-4-hydroxy-2-methyltetrahydropyran, used as a starting material, was obtained as follows:

Using the procedure described in Example 5 (2RS,4SR)-4-hydroxy-4-(3-hydroxyphenyl)-2-methyltetrahydropyran (0.3 g) was reacted with 2-bromomethyl-6,7-difluoronaphthalene (0.41 g) to give the required starting material (0.33 g, 60%), as an oil.

NMR Spectrum (CDCl$_3$, delta values) 1.2(d, 3H), 1.55–1.8(m, 4H), 2.0–2.2(m, 1H), 3.9(m, 3H), 5.2(s, 2H), 6.9–7.8(m, 9H).

m. Ethyl iodide was used as the alkylating agent, potassium hydroxide as the base and dimethylsulphoxide as the solvent, and the procedure described in the 3rd paragraph of the portion of Note e. below Table IV in Example 15 was utilised. The product displayed the following characteristic NMR signals (CDCl$_3$, delta values) 1.2(m, 5H), 1.5(t, 3H), 1.9(m, 2H), 2.9(m, 2H), 3.85(m, 3H), 5.2(s, 2H), 6.18(m, 2H), 6.85(m, 1H), 7.5(m, 3H), 7.87(m, 4H).

EXAMPLE 45

The procedure described in Example 5 was repeated using the appropriate alkyl bromide and the appropriate phenol. There were thus obtained the compounds described in the following table:

TABLE X

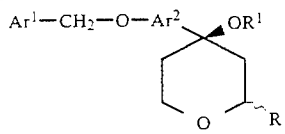

| Ex. 45 Compd. No. | Ar¹ | Ar² | R¹ | R | m.p. (°C.) | Yield (%) |
|---|---|---|---|---|---|---|
| 1[a] | 7-fluoronaphth-2-yl | 1,3-phenylene | Me | alpha-Me | oil | 77 |
| 2[b] | 7-fluoronaphth-2-yl | 1,3-phenylene | Me | beta-Me | oil | 58 |
| 3[c] | 7-fluoronaphth-2-yl | 1,3-phenylene | Et | alpha-Me | oil | 54 |
| 4[d] | 7-methylnaphth-2-yl | 1,3-phenylene | Me | alpha-Me | oil | 80 |
| 5[e] | 7-methylnaphth-2-yl | 1,3-phenylene | Me | beta-Me | oil | 48 |
| 6[f] | 7-methylnaphth-2-yl | 1,3-phenylene | Et | alpha-Me | oil | 51 |
| 7[g] | 7-fluoronaphth-2-yl | 5-fluoro-1,3-phenylene | Me | alpha-Me | oil | 83 |
| 8[h] | 7-fluoronaphth-2-yl | 5-fluoro-1,3-phenylene | Me | beta-Me | oil | 85 |
| 9[i] | 7-fluoronaphth-2-yl | 5-fluoro-1,3-phenylene | Et | alpha-Me | oil | 86 |
| 10[j] | 7-fluoronaphth-2-yl | 5-trifluoro-methyl-1,3-phenylene | Me | alpha-Me | oil | 86 |
| 11[k] | 7-fluoronaphth-2-yl | 5-trifluoro-methyl-1,3-phenylene | Me | beta-Me | oil | 80 |
| 12[l] | 7-fluoronaphth-2-yl | 5-trifluoro-methyl-1,3-phenylene | Et | alpha-Me | oil | 85 |
| 13[m] | 7-methylnaphth-2-yl | 5-trifluoro-methyl-1,3-phenylene | Me | alpha-Me | oil | 79 |

NOTES a. The product displayed the following characteristic NMR signals (CDCl₃, delta values) 1.2(d, 3H), 1.55(m, 2H), 1.95(m, 2H), 2.95(s, 3H), 3.9(m, 3H), 5.25(s, 2H), 6.9–7.9(m, 10H).

The (2RS,4SR)-4-(3-hydroxyphenyl)-4-methoxy-2-methyltetrahydropyran, used as a starting material, was obtained as follows:

Using the procedure described in Example 3, (2RS,4SR)-4-(3-benzyloxyphenyl)-4-hydroxy-2-methyltetrahydropyran (1.22 g; obtained as described within Note k. below Table IX in Example 44) was reacted with methyl iodide (0.5 ml), to give (2RS,4SR)-4-(3-benzyloxyphenyl)-4-methoxy-2-methyltetrahydropyran (0.84 g, 66%), as an oil.

Using the procedure also described within that Note k., the product so obtained was hydrogenolysed to give the required starting material (0.49 g, 82%), as an oil.

NMR Spectrum (CDCl₃, delta values) 1.2(d, 3H), 1.52–1.65(m, 1H), 1.92–2.03(m, 3H), 3.0(s, 3H), 3.87–3.97(m, 3H), 5.36(s, 1H), 6.73–7.27(m, 4H).

b. The product displayed the following characteristic NMR signals (CDCl₃, delta values) 1.15(d, 3H), 1.6(t, 1H), 1.9(m, 1H), 2.3(t, 2H), 2.85(s, 3H), 3.35(m, 2H), 3.9(d, 1H), 5.2(s, 2H), 6.9–7.9(m, 10H).

The (2SR,4SR)-4-(3-hydroxyphenyl)-4-methoxy-2-methyltetrahydropyran used as a starting material, was obtained using the procedures described in Note a. above except that (2SR,4SR)-4-(3-benzyloxyphenyl)-4-hydroxy-2-methyltetrahydropyran (1.38 g) was used as the starting material. There was thus obtained the required starting material (0.52 g, 50%), as an oil.

c. The product displayed the following characteristic NMR signals (CDCl₃, delta values) 1.05(t, 3H), 1.2(d, 3H), 1.55(t, 1H), 1.9(m, 3H), 3.05(q, 2H), 3.9(m, 3H), 5.2(s, 2H), 6.9–7.05(m, 3H), 7.1–7.3(m, 2H), 7.4–7.5(m, 2H), 7.8(m, 3H).

The (2RS,4SR)-4-ethoxy-4-(3-hydroxyphenyl)-2-methyltetrahydropyran, used as a starting material, was obtained by repeating the procedure described in Note a. above, except that ethyl iodide was used in place of methyl iodide. There was thus obtained the required starting material in 52% yield, as an oil.

NMR Spectrum (CDCl₃, delta values) 1.1(t, 3H), 1.2(d, 3H), 1.5–1.65(m, 2H), 1.9–2.0(m, 2H), 3.1(m, 2H), 3.9(m, 3H), 6.75–7.25(m, 4H).

d. The product displayed the following characteristic NMR signals (CDCl₃, delta values), 1.2(d, 3H), 1.5(m, 2H), 1.9–2.0 (m, 2H), 2.5(s, 3H), 2.95(s, 3H), 3.9(m, 3H), 5.2(s, 2H), 6.9–7.85(m, 10H).

e. The product displayed the following characteristic NMR signals (CDCl₃, delta values) 1.15(d, 3H), 1.6–2.0(m, 2H), 2.35(m, 2H), 2.5(s, 3H), 2.85(s, 3H), 3.4(m, 2H), 3.9(m, 1H), 5.2(s, 2H), 6.9–7.8(m, 10H).

f. The product displayed the following characteristic NMR signals (CDCl₃, delta values) 1.1(t, 3H), 1.2(d, 2H), 1.5–1.6(m, 1H), 1.9–2.0(m, 3H), 2.5(s, 3H), 3.0–3.1(m, 2H), 3.9(m, 3H), 5.2(s, 2H), 6.9–7.85(m, 10H).

g. The product displayed the following characteristic NMR signals (CDCl₃, delta values) 1.20(d, 3H), 1.54(m, 1H), 1.86–1.98(m, 3H), 2.96(s, 3H), 3.84–3.91(m, 3H), 5.2(s, 2H), 6.65(m, 1H), 6.73(m, 1H), 6.85(m, 1H), 7.1–7.9(m, 6H).

h. The product displayed the following characteristic NMR signals (CDCl₃, delta values) 1.18(d, 3H), 1.61(d of d's, 1H), 1.90(m, 1H), 2.2–2.37(m, 2H), 2.88(s, 3H), 3.3–3.42(m, 2H), 3.9–3.99(m, 1H), 5.21(s, 2H), 6.69(m, 1H), 6.77(m, 1H), 6.87(t, 1H), 7.1–7.9(m, 6H).

i. The product displayed the following charcteristic NMR signals (CDCl₃, delta values) 1.10(t, 3H), 1.23(d, 3H), 1.52(d of d's, 1H), 1.84–2.01(m, 3H), 3.06(q, 2H), 3.81–4.01(m, 3H), 5.20(s, 2H), 6.63(m, 1H), 6.72(m, 1H), 7.2–7.9(m, 6H).

The (2RS,4SR)-4-ethoxy-4-(5-fluoro-3-hydroxyphenyl)-2-methyltetrahydropyran used as a starting material was obtained as follows:

The procedure described in the portion of Example 3 which is concerned with the preparation of starting materials was repeated except that the diastereoisomers were not separated.

Using the procedure described in the 3rd paragraph of Note e. below Table IV in Example 15, the mixture of isomers (4.5 g) was reacted with ethyl iodide to give, after chromatography eluting with a 19:1 v/v mixture of toluene and ethyl acetate, a less polar isomer, (2RS,4SR)-4-(3-benzyloxy-5-fluorophenyl)-4-ethoxy-2-methyltetrahydropyran (0.7 g, 14%), as an oil; and a more polar isomer, the corresponding (2SR,4SR)-isomer (2.6 g, 52%), as an oil.

Using the procedure described within Note k. below Table IX in Example 44, the less polar isomer was hydrogenolysed to give the required starting material (0.52 g, 96%), as an oil.

NMR Spectrum (CDCl₃, delta values) 1.1(m, 6H), 1.54(d of d's, 1H), 1.84-2.04(m, 3H), 3.13(q, 2H), 3.82-4.04(m, 3H), 6.47(m, 1H), 6.63-6.77(m, 2H).

j. The product displayed the following characteristic NMR signals (CDCl₃, delta values) 1.2(d, 3H), 1.55(m, 1H), 1.9(m, 3H), 3.0(s, 3H), 3.9(m, 3H), 5.3(s, 2H), 7.1-7.3(m, 4H), 7.4-7.55(m, 2H), 7.8-7.9(m, 3H).

The (2RS,4SR)-4-(3-hydroxy-5-trifluoromethylphenyl)-4-methoxy-2-methyltetrahydropyran, used as a starting material, was obtained as follows:

The procedure described in the second paragraph of Note e. below Table IV in Example 15 was repeated, except that 3-benzyloxy-5-trifluoromethylbromobenzene (8.3 g) was used and 2-methyltetrahydropyran-4-one was used in place of tetrahydropyran-4-one. There were thus obtained a less polar isomer, (2RS,4SR)-4-(3-benzyloxy-5-trifluoromethylphenyl)-4-hydroxy-2-methyltetrahydropyran (1.44 g, 16%), as an oil, NMR Spectrum (CDCl₃, delta values, characteristic signals only) 1.25(d, 3H), 3.95(m, 3H), 5.1(s, 2H), 7.0-7.5(m, 8H); and a more polar isomer, the corresponding (2SR,4SR)-isomer (2.66 g, 30%), as an oil.

NMR Spectrum (CDCl₃, delta values) 1.2(d, 3H), 1.6-2.1(m, 3H), 2.2-2.4(m, 2H), 3.4(m, 2H), 3.9-4.05(m, 1H), 5.1(s, 2H), 7.15-7.5(m, 8H).

Using the procedure described in Example 3, the (2RS,4SR)-isomer (1.4 g) was reacted with methyl iodide to give (2RS,4SR)-4-(3-benzyloxy-5-trifluoromethylphenyl)-4-methoxy-2-methyltetrahydropyran (0.9 g, 68%). as an oil.

NMR Spectrum (CDCl₃, delta values) 1.2(d, 3H), 1.55(m, 1H), 1.85-2.0(m, 3H), 2.95(s, 3H), 3.8-4.0(m, 3H), 5.1(s, 2H), 7.1-7.5(m, 8H).

Using the procedure described within Note k. below Table IX in Example 44, the product so obtained was hydrogenolysed to give the required starting material (0.63 g, 90%), as a solid.

NMR Spectrum (CDCl₃, delta values) 1.2(d, 3H), 1.6(m, 2H), 2.0(m, 3H), 3.0(s, 3H), 3.85-4.0(m, 3H), 7.0-7.2(m, 3H).

k. The product displayed the following characteristic NMR signals (CDCl₃, delta values) 1.2(d, 3H), 1.65(m, 1H), 1.9-2.05(m, 1H), 2.35(m, 2H), 2.9(s, 3H), 3.35(m, 2H), 3.95(m, 1H), 5.3(s, 2H), 7.1-7.9(m, 9H).

The (2SR,4SR)-4-(3-hydroxy-5-trifluoromethylphenyl)-4-methoxy-2-methyltetrahydropyran, used as a starting material, was obtained using the procedures described in the last two paragraphs of Note j. above but taking the (2SR,4SR)-more polar isomer described therein as starting material. There was thus obtained the required starting material (88%), as an oil.

NMR Spectrum (CDCl₃, delta values) 1.25(m, 3H), 1.6-1.8(m, 1H), 1.9-2.1(1H), 2.35(m, 2H), 2.9(s, 3H), 3.4(m, 2H), 3.95-4.1(m, 1H), 7.0-7.2(m, 3H).

l. The product displayed the following characteristic NMR signals (CDCl₃, delta values) 1.1(t, 3H), 1.2(d, 3H), 1.55(m, 1H), 1.9-2.05(m, 3H), 3.1(m, 2H), 3.9(m, 3H), 5.28(s, 2H), 7.1-7.9(m, 9H).

The (2RS,4SR)-4-ethoxy-4-(3-hydroxy-5-trifluoromethylphenyl)-2-methyltetrahydropyran, used as a starting material, was obtained by repeating the procedure described in the last two paragraphs of Note j. above, except that ethyl iodide was used in place of methyl iodide. There was thus obtained the required starting material in 56% yield, as an oil.

NMR Spectrum (CDCl₃, delta values) 1.1-1.3(m, 6H), 1.55(m, 1H), 1.9-2.05(m, 3H), 3.05-3.2(m, 2H), 3.85-4.05(m, 3H), 5.65(m, 1H), 7.0-7.2(m, 3H).

m. The product displayed the following characteristic NMR signals (CDCl₃, delta values) 1.2(d, 3H), 1.55(m, 2H), 1.9-2.0(m, 2H), 2.5(s, 3H), 2.95(s, 3H), 3.85(m, 3H), 5.25(s, 2H), 7.1-7.9(m, 9H).

EXAMPLE 46

The procedure described in Example 5 was repeated except that (2RS,4SR)-4-ethoxy-4-(5-fluoro-3-hydroxyphenyl)-2-methyltetrahydropyran was used as the phenol component. There was thus obtained (2RS,4SR)-4-ethoxy-4-[5-fluoro-3-(3-phenylprop-2-ynyloxy)phenyl]-2-methyltetrahydropyran (41%), as an oil.

NMR Spectrum (CDCl₃, delta values) 1.1-1.2(m, 6H), 1.46-1.59(m, 2H), 1.87-2.0(m, 2H), 3.11(q, 2H), 3.86-3.96(m, 3H), 4.90(s, 2H), 6.6-6.8(m, 2H), 6.87(s, 1H), 7.25-7.45(m, 5H).

EXAMPLE 47

The procedure described in Example 5 was repeated except that (2SR,4SR)-4-ethoxy-4-(5-fluoro-3-hydroxyphenyl)-2-methyltetrahydropyran was used as the phenol component. There was thus obtained (2SR,4SR)-4-ethoxy-4-[5-fluoro-3-(3-phenylprop-2-ynyloxy)phenyl]-2-methyltetrahydropyran (61%), as an oil.

NMR Spectrum (CDCl₃, delta values) 1.01(t, 3H), 1.18(d, 3H), 1.63(m, 1H), 1.96(m, 1H), 2.31(m, 2H), 3.07(q, 2H), 3.36-3.47(m, 2H), 3.92-3.96(m, 1H), 4.91(s, 2H), 6.67-6.82(m, 2H), 6.91(s, 1H), 7.25-7.45(m, 5H).

The (2SR,4SR)-4-ethoxy-4-(5-fluoro-3-hydroxyphenyl)-2-methyltetrahydropyran, used as a starting material, was obtained by hydrogenolysis of a solution of (2SR,4SR)-4-(3-benzyloxy-5-fluorophenyl)-4-ethoxy-2-methyltetrahydropyran (2.6 g, described in Note i. below Table X in Example 45) in ethanol (25 ml) in the presence of 10% palladium-on-charcoal catalyst (0.26 g). The mixture was filtered and the filtrate was evaporated. There was thus obtained the required starting material (1.69 g, 89%), as an oil.

NMR Spectrum (CDCl₃, delta values) 1.04(t, 3H), 1.21(d, 3H), 1.69(d of d's, 1H), 1.98(m, 1H), 2.21-2.4(m, 2H), 3.12(q, 2H), 3.3-3.55(m, 2H), 3.98(m, 1H), 6.51(m, 1H), 6.7(m, 1H), 6.77(s, 1H).

EXAMPLE 48

Using the procedure described in Example 3, 4-(3-benzyloxyphenyl)-4-hydroxy-2,2-dimethyltetrahydropyran (1.14 g) was reacted with methyl iodide (0.25 ml) to give 4-(3-benzyloxyphenyl)-4-methoxy-2,2-dimethyltetrahydropyran (1.06 g, 89%), as an oil.

NMR Spectrum (CDCl₃, delta values) 1.18(s, 3H), 1.45(s, 3H), 1.71(d, 1H), 1.93-2.03(m, 3H), 2.92(s, 3H), 3.66-3.77(m, 1H), 3.94-4.10(m, 1H), 5.07(s, 2H), 6.88(d, 1H), 6.97(d, 1H), 7.02(s, 1H), 7.15-7.46(m, 6H).

The 4-(3-benzyloxyphenyl)-4-hydroxy-2,2-dimethyltetrahydropyran, used as a starting material, was obtained as follows:

A mixture of 2,3-dihydro-2,2-dimethylpyran-4-one (2.72 g, *J. Org. Chem.*, 1963, 687), 10% palladium-on-charcoal catalyst (0.27 g) and ethanol (80 ml) was stirred under an atmosphere of hydrogen for 6 hours. The mixture was filtered and the filtrate was evaporated. There was thus obtained 2,2-dimethyltetrahydropyran-4-one (2.05 g, 74%), as a liquid.

IR Spectrum 1730 cm⁻¹ (C=O).

Using the procedure described in the 2nd paragraph of the portion of Example 3 which is concerned with the preparation of starting materials, 3-benzyloxybromobenzene (1.34 g) was reacted with 2,2-dimethyltetrahydropyran-4-one (0.65 g) to give 4-(3-benzyloxyphenyl)-4-hydroxy-2,2-dimethyltetrahydropyran (1.14 g, 72%), as an oil.

NMR Spectrum (CDCl₃, delta values) 1.20(s, 3H), 1.50(s, 3H), 1.52(m, 1H), 1.57–1.73(m, 1H), 1.73–1.85(d, 2H), 2.08–2.27(m, 1H), 3.70–3.83(m, 1H), 4.09–4.24(d of t's, 1H), 5.08(s, 2H), 6.88(d of d's, 1H), 7.07(d, 1H), 7.14(t, 1H), 7.22–7.50(m, 6H).

EXAMPLE 49

Using the procedure described in Example 5, 2-bromomethylnaphthalene (0.245 g) was reacted with 4-(3-hydroxyphenyl)-4-methoxy-2,2-dimethyltetrahydropyran (0.25 g) to give 4-methoxy-2,2-dimethyl-4-[3-(naphth-2-ylmethoxy)phenyl]tetrahydropyran (0.38 g, 95%), as an oil.

NMR Spectrum (CDCl₃, delta values) 1.17(s, 3H), 1.45(s, 3H), 1.60(d, 1H), 1.96–2.04(m, 3H), 2.92(s, 3H), 3.71(m, 1H), 4.06(m, 1H), 5.24(s, 2H), 6.92(m, 1H), 6.97(m, 1H), 7.0(t, 1H), 7.28(t, 1H), 7.46–7.57(m, 3H), 7.82–7.89(m, 4H).

The 4-(3-hydroxyphenyl)-4-methoxy-2,2-dimethyltetrahydropyran, used as a starting material, was obtained as follows:

A mixture of 4-(3-benzyloxyphenyl)-4-methoxy-2,2-dimethyltetrahydropyran (1.06 g), 10% palladium-on-charcoal catalyst (0.44 g) and isopropanol (45 ml) was stirred under an atmosphere of hydrogen for 3 hours. The mixture was filtered and the filtrate was evaporated to give the required starting material (0.74 g, 96%), which was used without further purification.

EXAMPLE 50

Using the procedure described in Example 5, 7-fluoro-2-bromomethylnaphthalene (0.23 g) was reacted with 4-(3-hydroxyphenyl)-4-methoxy-2,2-dimethyltetrahydropyran (0.21 g) to give 4-[3-(7-fluoronaphth-2-ylmethoxy)phenyl]-4-methoxy-2,2-dimethyltetrahydropyran (0.35 g, 86%), as an oil.

NMR Spectrum (CDCl₃, delta values) 1.2(s, 3H), 1.49(s, 3H), 1.69–1.75(d, 1H), 1.9–2.1(m, 3H), 2.95(s, 3H), 3.65–3.75(m, 1H), 3.9–4.1(m, 1H), 5.25(s, 2H), 6.9–7.9(m, 10H).

EXAMPLE 51

The procedure described in Example 3 was repeated using the appropriate alkyl halide and the appropriate alcohol. There were thus obtained the compounds described in the following table:

TABLE XI

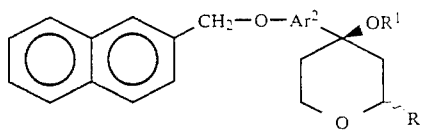

| Ex. 51 Compd. No. | Ar² | R¹ | R | m.p. (°C.) | Yield (%) |
|---|---|---|---|---|---|
| 1ᵃ | 1,3-phenylene | Me | alpha-ethyl | oil | 83 |
| 2ᵇ | 1,3-phenylene | Me | beta-ethyl | oil | 71 |
| 3ᶜ | 1,3-phenylene | Et | alpha-ethyl | oil | 63 |
| 4ᵈ | 1,3-phenylene | allyl | alpha-ethyl | oil | 67 |
| 5ᵉ | 5-fluoro-1,3-phenylene | Me | alpha-ethyl | oil | 39 |
| 6ᶠ | 5-fluoro-1,3-phenylene | allyl | alpha-ethyl | oil | 84 |
| 7ᵍ | 5-fluoro-1,3-phenylene | allyl | beta-ethyl | oil | 18 |
| 8ʰ | 5-trifluoromethyl-1,3-phenylene | allyl | alpha-ethyl | oil | 28 |
| 9ⁱ | 1,3-phenylene | Me | alpha-n-propyl | oil | 72 |
| 10ʲ | 1,3-phenylene | Me | beta-n-propyl | oil | 85 |
| 11ᵏ | 1,3-phenylene | allyl | alpha-n-propyl | oil | 65 |
| 12ˡ | 1,3-phenylene | allyl | beta-n-propyl | oil | 69 |
| 13ᵐ | 5-fluoro-1,3-phenylene | Me | alpha-n-propyl | oil | 48 |
| 14ⁿ | 5-fluoro-1,3-phenylene | Me | beta-n-propyl | oil | 53 |
| 15ᵒ | 5-fluoro-1,3-phenylene | allyl | alpha-n-propyl | oil | 48 |
| 16ᵖ | 5-fluoro-1,3-phenylene | allyl | beta-n-propyl | oil | 64 |

NOTES a. Methyl iodide was used as the alkylating agent. The product displayed the following characteristic NMR signals (CDCl₃, delta values) 0.9(t, 3H), 1.2–2.1(m, 6H), 2.9(s, 3H), 3.65(m, 1H), 3.9(m, 2H), 5.2(s, 2H), 6.9–7.9(m, 1H).

The (2RS,4SR)-2-ethyl-4-hydroxy-4-[3-(naphth-2-ylmethoxy)phenyl]tetrahydropyran, used as a starting material, was obtained by repeating the procedure described in the portion of Note a. below Table IX in Example 44, except that 2-ethyltetrahydropyran-4-one (Chem. Ber., 1955, 88, 1053) was used in place of 2-methyltetrahydropyran-4-one. There were thus obtained: a less polar isomer, (2RS,4SR)-2-ethyl-4-hydroxy-4-[3-(naphth-2-ylmethoxy)phenyl]tetrahydropyran in 26% yield, m.p. 85°–87° C., i.e. the 2-ethyl and 4-hydroxy substituents are in trans-relationship; and a more polar isomer, (2SR,4SR)-2-ethyl-4-hydroxy-4-[3-(naphth-2-ylmethoxy)phenyl]tetrahydropyran in 21% yield, m.p. 73°–75° C., i.e. the 2-ethyl and 4-hydroxy substituents are in a cis-relationship.

b. The product displayed the following characteristic NMR signals (CDCl₃, delta values) 0.9(t, 3H), 1.2–2.5(m, 6H), 2.85(s, 3H), 3.15(m, 1H), 3.4(m, 1H), 3.95(m, 1H), 5.2(s, 2H), 6.9–7.9(m, 11H).

The (2SR,4SR)-isomer, described in Note a. above, was used as the required starting material.

c. Ethyl iodide was used as the alkylating agent. The product displayed the following characteristic NMR signals (CDCl₃, delta values) 0.9–2.05(m's, 12H), 3.1(q, 2H), 3.7(m, 1H), 3.9(m, 2H), 5.25(s, 2H), 6.9–7.9(m, 11H).

d. Allyl bromide was used as the alkylating agent. The product displayed the following charcteristic NMR signals (CDCl₃, delta values) 0.95(t, 3H), 1.4–2.1(m, 6H), 3.6(m, 2H), 3.65(m, 1H), 3.9(m, 2H), 5.1–5.3(m, 4H), 5.75–5.95(m, 1H), 6.9–7.9(m, 11H).

e. Methyl iodide was used as the alkylating agent. The product displayed the following characteristic NMR signals (CDCl₃, delta values) 0.9(t, 3H), 1.4–2.0(m, 6H), 2.9(s, 3H), 3.4(m, 2H), 3.95(m, 1H), 5.2(s, 2H), 6.65-7.9(m, 10H).

The (2RS,4SR)-2-ethyl-4-[5-fluoro-3-(naphth-2-ylmethoxy)phenyl]-4-hydroxytetrahydropyran, used as a starting material, was obtained using 5-fluoro-3-(naphth-2-ylmethoxy)bromobenzene and 2-ethyltetrahydropyran-4-one as the starting materials and using the procedure described in the portion of Note a. below Table IX in Example 44. There were thus obtained: a less polar isomer, (2RS,4SR)-2-ethyl-4-[5-fluoro-3-(naphth-2-ylmethoxy)phenyl]-4-hydroxytetrahydrofuran in 13% yield, as an oil; and a more polar isomer, the corresponding (2SR,4SR)-isomer, in 12% yield, as an oil.

f. Allyl bromide was used as the alkylating agent. The product displayed the following characteristic NMR signals (CDCl$_3$, delta values) 0.9(t, 3H), 1.5(m, 4H), 1.9(m, 2H), 3.6(m, 2H), 3.7(m, 1H), 3.9(m, 2H), 5.2(m, 4H), 5.84(m, 1H), 6.6-7.9(m, 10H).

g. Allyl bromide was used as the alkylating agent. The product displayed the following charcteristic NMR signals (CDCl$_3$, delta values) 0.9(t, 3H), 1.4(m, 2H), 1.65(m, 1H), 1.95(m, 1H), 2.28(m, 2H), 3.0-3.4(m, 2H), 3.5(m, 2H), 3.9(m, 1H), 5.05(m, 2H), 5.2(s, 2H), 5.7(m, 1H), 6.6-7.9(m, 10H).

The (2SR,4SR)-isomer, described in Note e above, was used as the required starting material.

h. Allyl bromide was used as the alkylating agent. The product displayed the following characteristic NMR signals (CDCl$_3$, delta values) 0.95(t, 3H), 1.4-2.1(m, 8H), 3.6(m, 1H), 3.9(m, 2H), 5.2(m, 2H), 5.8(m, 1H), 5.3(s, 2H), 7.1-7.9(m, 10H).

The (2RS,4SR)-2-ethyl-4-hydroxy-4-[3-(naphth-2-ylmethoxy)-5-trifluoromethylphenyl]tetrahydropyran, used as a starting material, was obtained, using the procedure described in the portion of Note a. below Table IX in Example 44, and using 3-(naphth-2-ylmethoxy)-5-trifluoromethylbromobenzene and 2-ethyltetrahydropyran-4-one as the starting materials. There were thus obtained: a less polar isomer (2RS,4SR)-2-ethyl-4-hydroxy-4-[3-(naphth-2-ylmethoxy)-5-trifluorophenyl]tetrahydropyran in 4% yield, as an oil; and a more polar isomer, the corresponding (2SR,4SR)-isomer, in 11% yield, as an oil.

i. Methyl iodide was used as the alkylating agent. The product displayed the following characteristic NMR signals (CDCl$_3$, delta values) 0.9(t, 3H), 1.4(m, 4H), 1.55(m, 2H), 1.95(m, 2H), 3.0(s, 3H), 3.85(m, 3H), 5.2(s, 2H), 7.0-7.9(m, 11H).

The (2RS,4SR)-4-hydroxy-4-[3-(naphth-2-ylmethoxy)phenyl]-2-n-propyltetrahydropyran, used as a starting material, was obtained by repeating the procedure described in the portion of Note a. below Table IX in Example 44, except that 2-n-propyltetrahydropyran-4-one (*Chem. Ber.*, 1955, 88, 1053) was used in place of 2-methyltetrahydropyran-4-one. There were thus obtained: a less polar isomer, (2RS,4SR)-4-hydroxy-4-[3-(naphth-2-ylmethoxy)phenyl]-2-n-propyltetrahydropyran in 18% yield, as an oil; and a more polar isomer, the corresponding (2SR,4SR)-isomer in 11% yield, as an oil.

j. The product displayed the following characteristic NMR signals (CDCl$_3$, delta values) 0.9(t, 3H), 1.4(m, 4H), 2.0-2.4(m, 4H), 2.9(m, 2H), 3.4(m, 2H), 3.9(m, 1H), 5.2(s, 2H), 7.0-7.9(m, 11H).

The (2SR,4SR)-isomer, described in Note i. above, was used as the required starting material.

k. Allyl bromide was used as the alkylating agent. The product displayed the following characteristic NMR signals (CDCl$_3$, delta values) 0.9(t, 3H), 1.45(m, 6H), 1.95(m, 2H), 3.6(m, 2H), 3.9(m, 3H), 5.2(m, 4H), 5.8(m, 1H), 7.0-7.9(m, 11H).

l. The product displayed the following charcteristic NMR signals (CDCl$_3$, delta values) 0.9(t, 3H), 1.4(m, 4H), 1.7-1.9(m, 2H), 2.34(m, 2H), 3.4(m, 2H), 3.5(m, 2H), 3.9(m, 1H), 5.1(m, 2H), 5.2(s, 2H), 5.7(m, 1H), 7.0-7.9(m, 11H).

m. Methyl iodide was used as the alkylating agent. The product displayed the following characteristic NMR signals (CDCl$_3$, delta values) 0.9(t, 3H), 1.4(m, 4H), 1.5-1.9(m, 4H), 3.0(s, 3H), 3.8(m, 3H), 5.2(s, 2H), 6.6-7.9(m, 10H).

The (2RS,4SR)-4-[5-fluoro-3-(naphth-2-ylmethoxy)phenyl]-4-hydroxy-2-n-propyltetrahydropyran, used as a starting material, was obtained, using the procedure described in the portion of Note a. below Table IX in Example 44, and using 5-fluoro-3-(naphth-2-ylmethoxy)bromobenzene and 2-n-propyltetrahydropyran-4-one as the starting materials. There were thus obtained: a less polar isomer, (2RS,4SR)-4-[5-fluoro-3-(naphth-2-ylmethoxy)phenyl]-4-hydroxy-2-n-propyltetrahydropyran in 17% yield, as an oil; and a more polar isomer, the corresponding (2SR,4SR)-isomer, in 10% yield, as an oil.

n. The product displayed the following characteristic NMR signals (CDCl$_3$, delta values) 0.9(t, 3H), 1.5-1.9(m, 6H). 2.28(m, 2H) 2.9(s, 3H), 3.3(m, 2H), 3.9(m, 1H), 5.2(s, 2H), 6.6-7.9(m, 10H).

o. Allyl bromide was used as the alkylating agent. The product displayed the following characteristic NMR signals (CDCl$_3$, delta values) 0.9(t, 3H), 1.4-1.9(m, 8H), 3.6(m, 2H), 3.9(m, 3H), 5.2(m, 4H), 5.7(m, 3H), 6.6-7.9(m, 10H).

p. The product displayed the following charcteristic NMR signals (CDCl$_3$, delta values) 0.9(t, 3H), 1.4(m, 4H), 1.7-1.9(m, 2H), 2.3(m, 2H), 3.4(m, 2H), 3.6(m, 2H), 3.94(m, 1H), 5.1(m, 2H), 5.2(s, 2H), 5.7(m, 1H), 6.7-7.9(m, 10H).

EXAMPLE 52

Using the procedure described in Example 5, 2-bromomethylnaphthalene (0.234 g) was reacted with 4-(3-hydroxyphenyl)-4-methoxy-2,6-dimethyltetrahydropyran (0.2 g, less polar isomer) to give 4-methoxy-2,6-dimethyl-4-[3-(naphth-2-ylmethoxy)phenyl]tetrahydropyran (0.29 g, 92%), m.p. 105°-107° C.

The 4-(3-hydroxyphenyl)-4-methoxy-2,6-dimethyltetrahydropyran (less polar isomer), used as a starting material, was obtained as follows:

A solution of 2,6-dimethyltetrahydropyran-4-one (2.2 g) in tetrahydrofuran (5 ml) was added to a solution of 3-benzyloxyphenylmagnesium bromide [prepared by heating a mixture of 3-benzyloxybromobenzene (5 g), magnesium (0.5 g) and tetrahydrofuran (20 ml)] in tetrahydrofuran and the mixture was stirred at ambient temperature for 3 hours. The mixture was cooled to 5° C., ice (5 ml) and 2N hydrochloric acid solution (25 ml) were added, and the mixture was extracted with ethyl acetate. The organic phase was washed with a saturated sodium chloride solution, dried (MgSO$_4$) and evaporated. The residue was purifed by column chromatography using increasingly polar mixtures of toluene and ethyl acetate as eluent. There were thus obtained two isomers of 4-(3-benzyloxyphenyl)-4-hydroxy-2,6-dimethyltetrahydropyran: a less polar isomer (2.41 g, 45%), NMR Spectrum (CDCl$_3$, delta values) 1.2-1.3(d, 6H), 1.6(broad s, 1H), 1.7(m, 4H), 3.95-4.1(m, 2H), 5.1(s, 2H), 6.9-7.5(m, 9H); and a more polar isomer (1.57 g, 29%), NMR Spectrum (CDCl$_3$, delta values) 1.2(d, 6H), 1.55-1.9(m, 3H), 2.3-2.4(m, 2H), 3.3-3.5(m, 2H), 5.1(s, 2H), 6.9-7.5(m, 9H).

Using the procedure described in Example 3, the less polar isomer so obtained was reacted with methyl iodide to give 4-(3-benzyloxyphenyl)-4-methoxy-2,6-dimethyltetrahydropyran (80%), as an oil.

Using the procedure described within Note k. below Table IX in Example 44, the product so obtained was hydrogenolysed to give the required starting material (92%), as an oil.

EXAMPLE 53

Using the procedure described in Example 5, 7-fluoro-2-bromomethylnaphthalene (0.265 g) was reacted with 4-(3-hydroxyphenyl)-4-methoxy-2,6-dimethyltetrahydropyran (0.225 g, less polar isomer) to give 4-[3-(7-fluoronaphth-2-ylmethoxy)phenyl]-4-methoxy-2,6-dimethyltetrahydropyran (0.37 g, 93%), as an oil.

NMR Spectrum (CDCl$_3$, delta values) 1.2(d, 6H), 1.5-1.6(m, 3H), 1.9-2.1(d, 1H), 3.0(s, 3H), 3.85-4.05(m, 2H), 5.2(s, 2H), 6.8-7.9(m, 10H).

EXAMPLE 54

Using the procedure described in Example 5, 7-fluoro-2-bromomethylnaphthalene (0.5 g) was reacted with 4-(3-hydroxyphenyl)-4-methoxy-2,6-dimethyltetrahydropyran (0.45 g, more polar isomer) to give 4-[3-(7-fluoronaphth-2-ylmethoxy)phenyl]-4-methoxy-2,6-dimethyltetrahydropyran (0.74 g, 77%), as an oil which crystallised on standing, m.p. 77° C.

The 4-(3-hydroxyphenyl)-4-methoxy-2,6-dimethyltetrahydropyran (more polar isomer), used as a starting material, was obtained as follows:

Using the procedure described in Example 3, the more polar isomer of 4-(3-benzyloxyphenyl)-4-hydroxy-2,6-dimethyltetrahydropyran (described in the portion of Example 52 which is concerned with the preparation of starting materials) was reacted with methyl iodide to give 4-(3-benzyloxyphenyl)-4-methoxy-2,6-dimethyltetrahydropyran, (77%, more polar isomer), as an oil.

Using the procedure described within Note k. below Table IX in Example 44, the product so obtained was hydrogenolysed to give the required starting material (93%), as an oil.

EXAMPLE 55

Using the procedure described in Example 5, 4-(5-fluoro-3-hydroxyphenyl)-4-methoxytetrahydropyran was reacted with 5-bromo-2-bromomethylnaphthalene to give 4-[3-(5-bromonaphth-2-ylmethoxy)-5-fluorophenyl]-4-methoxytetrahydropyran in 52% yield, as an oil.

NMR Spectrum (CDCl$_3$, delta values) 1.8-2.1(m, 4H), 2.95(s, 3H), 3.75-3.90(m, 4H), 5.25(s, 2H), 6.6-8.25(m, 9H).

The 5-bromo-2-bromomethylnaphthalene, used as a starting material, was obtained as follows:

6-Methyl-1-naphthoic acid (6 g; J. Amer. Chem. Soc., 1941, 63, 1857) was added to thionyl chloride (50 ml) and the mixture was heated to reflux for 30 minutes. The solution was evaporated to give 6-methyl-1-naphthoyl chloride.

A solution of a mixture of the product so obtained and 2,2'-azobisisobutyronitrile (1.62 g) in bromotrichloromethane (5 ml) was added dropwise to a suspension of the sodium salt of 2-mercaptopyridine-N-oxide (4.84 g) in bromotrichloromethane (50 ml) which was stirred and heated to 100° C. The mixture was heated to 100° C. for 2 hours and then stirred at ambient temperature for 16 hours. The mixture was partitioned between methylene chloride and water. The organic layer was washed with 2N aqueous hydrochloric acid solution, with 2N aqueous sodium hydroxide solution and with water, dried (MgSO$_4$) and evaporated. The residue was purified by column chromatography using hexane as eluent to give 1-bromo-6-methylnaphthalene (2.79 g, 40%), as a liquid.

A mixture of a portion (1 g) of the product so obtained, N-bromosuccinimide (0.81 g), 2,2'-azobisisobutyronitrile (0.05 g) and carbon tetrachloride (25 ml) was heated to reflux and irradiated with light from a 275 watt bulb for 1 hour. The mixture was cooled to ambient temperature and filtered. The filtrate was evaporated and the residue was purified by column chromatography using hexane as eluent. There was thus obtained the required starting material (0.84 g, 61%), m.p. 110°-114° C.

EXAMPLE 56

Using the procedure described in Example 5, 4-(5-fluoro-3-hydroxyphenyl)-4-methoxytetrahydropyran was reacted with 2-bromomethyl-5-trifluoromethylnaphthalene to give 4-[5-fluoro-3-(5-trifluoromethylnaphth-2-ylmethoxy)phenyl]-4-methoxytetrahydropyran in 36% yield, as an oil.

NMR Spectrum (CD$_3$SOCD$_3$, delta values) 1.8-2.0 (m, 4H), 2.85 (s, 3H), 3.4-3.7 (m, 4H), 5.25 (s, 2H), 6.75-7.0 (m, 3H), 7.6-8.3 (m, 6H).

The 2-bromomethyl-5-trifluoromethylnaphthalene, used as a starting material, was obtained as follows:

Sodium trifluoroacetate (4.41 g) and cuprous iodide (3.08 g) were added in turn to a solution of 1-bromo-6-methylnaphthalene (1.79 g) in N,N-dimethylacetamide (36 ml) and the mixture was heated to reflux for 10 hours. The mixture was cooled to ambient temperature and filtered. The filtrate was evaporated and the residue was partitioned between diethyl ether and water. The organic layer was washed with water and with a saturated aqueous sodium chloride solution, dried (MgSO$_4$) and evaporated. The residue was purified by column chromatography using hexane as eluent. There was thus obtained 6-methyl-1-trifluoromethylnaphthalene (1 g, 59%), as an oil.

Using a similar procedure to that described in the last paragraph of Example 55 above, except that the reaction mixture was heated to reflux for 24 hours, the product so obtained was brominated to give the required starting material (0.7 g, 52%), m.p. 48°-65° C.

EXAMPLE 57

Using the procedure described in Example 3, (2R,4S)-4-hydroxy-2-methyl-4-[3-(naphth-2-ylmethoxy)phenyl]tetrahydropyran was reacted with methyl iodide to give (2R,4S)-4-methoxy-2-methyl-4-[3-naphth-2-ylmethoxy)phenyl]tetrahydropyran in 82% yield, m.p. 60°-62° C., [α]$^{20}$= −2.5° (chloroform, c=2 g/100 ml).

The (2R,4S)-4-hydroxy-2-methyl-4-[3-(naphth-2-ylmethoxy)phenyl]tetrahydropyran, used as a starting material, was obtained as follows:

Using the procedure described in the portion of Example 3 which is concerned with the preparation of starting materials, 3-(naphth-2-ylmethoxy)bromobenzene was converted into 3-(naphth-2-ylmethoxy)phenyl-lithium which was reacted with (−)-(R)-2-methyl-tetrahydropyran-4-one (*J. Amer. Chem. Soc.*, 1982, 104, 4670). There were thus obtained:

a less polar isomer, (2R,4S)-4-hydroxy-2-methyl-4-[3-(naphth-2-ylmethoxy)phenyl]tetrahydropyran, in 20% yield, m.p. 94°–96° C., i.e. the 2-methyl and 4-hydroxy groups are in a trans-relationship; and a more polar isomer, (2R,4R)-4-hydroxy-2-methyl-4-[3-(naphth-2-ylmethoxy)phenyl]tetrahydropyran, in 22% yield, m.p. 105°–109° C., i.e. the 2-methyl and 4-hydroxy groups are in a cis-relationship.

EXAMPLE 58

Using the procedure described in Example 3, (2R,4R)-4-hydroxy-2-methyl-4-[3-(naphth-2-ylmethoxy)phenyl]tetrahydropyran was reacted with methyl iodide to give (2R,4R)-4-methoxy-2-methyl-4-[3-(naphth-2-ylmethoxyphenyl]tetrahydropyran in 73% yield, as an oil. $[\alpha]^{20} = +8.5°$ (chloroform, c=2 g/100 ml).

NMR Spectrum (CDCl$_3$, delta values) 1.2(d, 3H), 1.6–2.4(m, 4H), 2.8(s, 3H), 3.4(m, 2H), 3.9(m, 4H), 5.2(s, 2H), 6.9–8.0(m, 11H).

EXAMPLE 59

A mixture of 4-methoxy-4-[3-(naphth-2-ylmethoxy)phenyl]thiacyclohexane (0.364 g; Example 2, Compound No. 3), m-chloroperbenzoic acid (0.344 g) and methylene chloride (4 ml) was stirred at ambient temperature for 4 hours. The mixture was partitioned between methylene chloride and a saturated aqueous sodium chloride solution. The organic phase was washed with a saturated aqueous sodium chloride solution, dried (MgSO$_4$) and evaporated. The residue was purified by column chromatography using initially a 4:1 v/v mixture of methylene chloride and diethyl ether and then a 4:1 v/v mixture of methylene chloride and acetone as eluent. There were thus obtained:

4-methoxy-4-[3-(naphth-2-ylmethoxy)phenyl]thiacyclohexane 1-oxide 0.1 g, 25%), m.p. 141°–142° C.; and 4-methoxy-4-[3-(naphth-2-ylmethoxy)phenyl]thiacyclohexane 1,1-dioxide (0.1 g, 25%), m.p. 110°–111° C.

EXAMPLE 60

The following illustrate representative pharmaceutical dosage forms containing the compound of formula I, or a pharmaceutically-acceptable salt salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 mg |
| Lactose Ph.Eur | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | mg/ml |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | mg/ml |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | mg/ml |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

Sheet 1/2

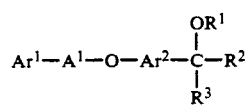

I

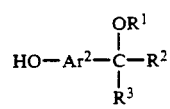

II

-continued
CHEMICAL FORMULAE

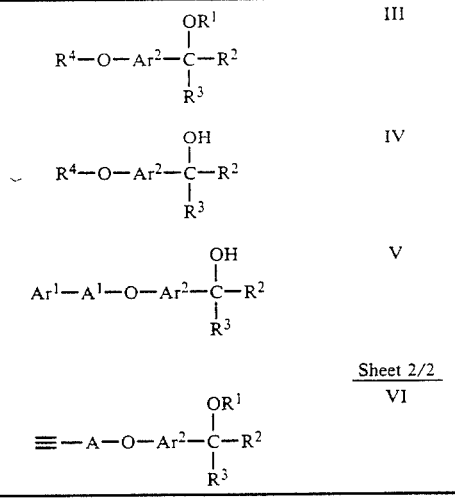

Sheet 2/2

What we claim is:

1. A heterocyclic derivative of the formula I

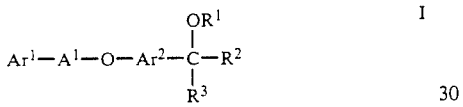

wherein $Ar^1$ is phenyl or naphthyl which may optionally bear one or more substituents selected from amino, halogeno, hydroxy, carboxy, cyano, (1-6C)alkyl, (2-6C)alkenyl, (2-6C)alkynyl, (1-4C)alkoxy, (1-4C)alkylthio, (1-4C)alkysulphinyl, (1-4C)alkylsulphonyl, (1-4C)alkylamino, di-[(1-4C)alkyl]amino, (1-4C)alkoxycarbonyl, (2-4C)alkanoyl, (2-4C)alkanoylamino, hydroxy-(1-4C)alkyl, fluoro-(1-4C)alkyl, amino-(1-4C)alkyl, cyano-(1-4C)alkyl and cyano-(1-4C)alkoxy;

wherein $A^1$ is (1-6C)alkylene, (3-6C)alkenylene, (3-6C)alkynylene or cyclo(3-6C)alkylene;

wherein $Ar^2$ is phenylene which may optionally bear one or two substituents selected from halogeno, hydroxy, amino, nitro, cyano, carbamoyl, ureido, (1-4C)alkyl, (3-4C)alkenyloxy, (1-4C)alkoxy, (1-4C)alkylthio, (1-4C)alkylsulphinyl, (1-4C)alkylsulphonyl, (1-4C)alkylamino, di-[(1-4C)alkyl]amino, fluoro-(1-4C)alkyl, (1-4C)alkoxycarbonyl, N-[(1-4C)alkyl]carbamoyl, N,N-di-[(1-4C)alkyl]carbamoyl, (2-4C)alkanoylamino, cyano-(1-4C)alkoxy, carbamoyl-(1-4C)alkoxy, (1-4C)alkoxycarbonyl-(1-4C)alkoxy, hydroxy-(2-4C)alkylamino, cyano-(1-4C)alkylamino, carboxy-(1-4C)alkylamino and (1-4C)alkoxycarbonyl-(1-4C)alkylamino;

wherein $R^1$ is hydrogen, (1-6C)alkyl, (3-6C)alkenyl, (3-6C)alkynyl, cyano-(1-4C)alkyl or (2-4C)alkanoyl, or $R^1$ is benzoyl which may optionally bear a substituent selected from halogeno, (1-4C)alkyl and (1-4C)alkoxy; and wherein $R^2$ and $R^3$ together form a group of the formula $-A^2-X-A^3-$ which, together with the carbon atom to which $A^2$ and $A^3$ are attached, defines a ring having 6 ring atoms, wherein $A^2$ and $A^3$, which may be the same or different, each is (1-4C)alkylene and X is oxy, and which ring may bear one, two or three substituents, which may be the same or different, selected from hydroxy, (1-4C)alkyl, (1-4C)alkoxy, (3-4C)alkenyloxy and (3-4C)alkynyloxy;

or a pharmaceutically-acceptable salt thereof.

2. A heterocyclic derivative of the formula I as claimed in claim 1 wherein $Ar^1$ is phenyl or naphthyl which may optionally bear one or more substituents selected from halogeno, hydroxy, carboxy, cyano, (1-4C)alkyl, (2-4C)alkenyl, (2-4C)alkynyl, (1-4C)alkoxy, (1-4C)alkylthio, (1-4C)alkysulphinyl, (1-4C)alkylsulphonyl, (1-4C)alkylamino, di-[(1-4C)alkyl]amino, (1-4C)alkoxycarbonyl, (2-4C)alkanoyl, hydroxy-(1-4C)alkyl and fluoro-(1-4C)alkyl; wherein $A^1$ is (1-6C)alkylene, (3-6C)alkenylene, (3-6C)alkynylene or cyclo(3-6C)alkylene;

wherein $Ar^2$ is phenylene which may optionally bear one or two substituents selected from halogeno, hydroxy, amino, nitro, cyano, carbamoyl, (1-4C)alkyl, (3-4C)alkenyl, (1-4C)alkoxy, (1-4C)alkylthio, (1-4C)alkylsulphinyl, (1-4C)alkysulphonyl, (1-4C)alkylamino, di-[(1-4C)alkyl]amino, fluoro-(1-4C)alkyl, (1-4C)alkoxycarbonyl, N-[(1-4C)alkyl]carbamoyl, N,N-di-[(1-4C)alkyl]carbamoyl, (2-4C)alkanoylamino, cyano-(1-4C)alkoxy, carbamoyl-(1-4C)alkoxy and (1-4C)alkoxycarbonyl-(1-4C)alkoxy;

wherein $R^1$ is hydrogen, (1-6C)alkyl, (3-6C)alkenyl, (3-6C)alkynyl, cyano-(1-4C)alkyl or (2-4C)alkanoyl, or $R^1$ is benzoyl which may optionally bear a substituent selected from halogeno, (1-4C)alkyl and (1-4C)alkoxy; and wherein $R^2$ and $R^3$ together a group of the formula $-A^2-X-A^3-$ which, together with the carbon atom to which $A^2$ and $A^3$ are attached, defines a ring having 6 ring atoms, wherein $A^2$ and $A^3$, which may be the same or different, each is (1-4C)alkylene and X is oxy;

or a pharmaceutically-acceptable salt thereof.

3. A heterocyclic derivative of the formula I as claimed in claim 1 wherein $Ar^1$ is phenyl or naphth-2-yl which may optionally bear one or two substituents selected from amino, fluoro, chloro, bromo, cyano, methyl, ethyl, propyl, isopropyl, butyl, tert-butyl, methoxy, methylthio, methylsulphinyl, methylsulphonyl, difluoromethyl, trifluoromethyl, cyanomethyl, 1-cyanoethyl, 2-cyanoprop-2-yl, cyanomethoxy and 2-cyanoethoxy;

$A^1$ is methylene, 1-propenylene or 1-propynylene;

$Ar^2$ is 1,3-phenylene or 1,4-phenylene which may optionally bear one substituent selected from fluoro, hydroxy, amino, nitro, ureido, methoxy, methylamino, dimethylamino, trifluoromethyl, acetamido, cyanomethoxy, 2-hydroxyethylamino, cyanomethylamino and carboxymethylamino;

$R^1$ is hydrogen, methyl, ethyl, allyl or 2-propynyl; and $R^2$ and $R^3$ together form a group of the formula $-A^2-X-A^3-$ which, together with the carbon atom to which $A^2$ and $A^3$ are attached, defines a ring having 6 ring atoms, wherein $A^2$ is ethylene, $A^3$ is ethylene, and X is oxy, and which ring may bear one or two substituents, which may be the same or different, selected from hydroxy, methyl, ethyl, propyl and methoxy; or a pharmaceutically-acceptable salt thereof.

4. A heterocyclic derivative of the formula I as claimed in claim 1 wherein
  Ar¹ is phenyl or naphth-2-yl which may optionally bear one or two substituents selected from fluoro, chloro, bromo, cyano, methyl, ethyl, tert-butyl, methylthio, methylsulphinyl, difluoromethyl, trifluoromethyl and cyanomethoxy;
  A¹ is methylene or 1-propynylene;
  Ar² is 1,3-phenylene which may optionally bear one substituent selected from fluoro, amino, nitro, ureido, dimethylamino, trifluoromethyl and cyanomethylamino;
  R¹ is methyl, ethyl or allyl; and
  R² and R³ together form a group of the formula —A²-X-A³- which, together with the carbon atom to which A² and A³ are attached, defines a ring having 6 ring atoms, wherein A² is ethylene, A³ is ethylene and X is oxy, and which ring may bear a methyl or ethyl substituent alpha to X;
or a pharmaceutically-acceptable salt thereof.

5. A heterocyclic derivative of the formula I as claimed in claim 1 wherein
  Ar¹ is phenyl, 4-fluorophenyl, 2,4-difluorophenyl, 2-chlorophenyl, 3-chlorophenyl, 3,5-dichlorophenyl, 2,5-dimethylphenyl, 4-ethylphenyl, 4-tert-butylphenyl, 4-methylthiophenyl, 4-methylsulphinylphenyl, 2-trifluoromethylphenyl, 2-cyanomethoxyphenyl, 3-cyanomethoxyphenyl, 2-cyano-3-fluorophenyl or 2-methylthio-5-trifluoromethylphenyl;
  A¹ is 1-propynylene;
  Ar² is 1,3-phenylene, 5-fluoro-1,3-phenylene, 5-amino-1,3-phenylene, 5-nitro-1,3-phenylene, 5-ureido-1,3-phenylene, 5-dimethylamino-1,3-phenylene, 5-trifluoromethyl-1,3-phenylene, 5-acetamido-1,3-phenylene, 5-(2-hydroxyethylamino)-1,3-phenylene or 5-cyanomethylamino-1,3-phenylene;
  R¹ is methyl, ethyl or allyl; and
  R² and R³ together form a group of the formula —A²-X-A³- which, together with the carbon atom to which A² and A³ are attached, defines a ring having 6 ring atoms, wherein each of A² and A³ is ethylene and X is oxy, and which ring may bear a methyl or ethyl substituent alpha to X;
or a pharmaceutically-acceptable salt thereof.

6. A heterocyclic derivative of the formula I as claimed in claim 1 wherein
  Ar¹ is naphth-2-yl, 7-fluoronaphth-2-yl, 6,7-difluoronaphth-2-yl, 7-methylnaphth-2-yl, 7-difluoromethylnaphth-2-yl, 5-bromonaphth-2-yl or 5-trifluoromethylnaphth-2-yl;
  A¹ is methylene;
  Ar² is 1,3-phenylene, 5-fluoro-1,3-phenylene or 5-trifluoromethyl-1,3-phenylene;
  R¹ is methyl, ethyl or allyl; and
  R² and R³ together form a group of the formula —A²-X-A³- which, together with the carbon atom to which A² and A³ are attached, defines a ring having 6 ring atoms, wherein each of A² and A³ is ethylene and X is oxy, and which ring may bear a methyl or ethyl substituent alpha to X;
or a pharmaceutically-acceptable salt thereof.

7. A heterocyclic derivative of the formula I as claimed in claim 1 selected from the group consisting of:
  4-methoxy-4-[3-(naphth-2-ylmethoxy)phenyl]tetrahydropyran,
  (2RS,4SR)-4-[5-fluoro-3-(3-phenylprop-2-ynyloxy)phenyl]-4-methoxy-2-methyltetrahydropyran,
  4-[5-fluoro-3-(3-phenylprop-2-ynyloxy)phenyl]-4-methoxytetrahydropyran,
  4-[5-amino-3-(3-phenylprop-2-ynyloxy)phenyl]-4-methoxytetrahydropyran,
  4-methoxy-4-[3-(3-phenylprop-2-ynyloxy)-5-trifluoromethylphenyl]tetrahydropyran,
  4-[5-fluoro-3-(3-(4-fluorophenyl)prop-2-ynyloxy)phenyl]-4-methoxytetrahydropyran,
  4-[5-(2-hydroxyethylamino)-3-(3-phenylprop-2-ynyloxy)phenyl]-4-methoxytetrahydropyran,
  4-methoxy-4-[3-(3-phenylprop-2-ynyloxy)-5-ureidophenyl]tetrahydropyran,
  4-[3-(3-(2-chlorophenyl)prop-2-ynyloxy)-5-fluorophenyl]-4-methoxytetrahydropyran,
  4-[5-fluoro-3-(3-(2-trifluoromethyl)phenylprop-2-ynyloxy)phenyl]-4-methoxytetrahydropyran,
  4-[3-(3-(3,5-dichlorophenyl)prop-2-ynyloxy)-5-fluorophenyl]-4-methoxytetrahydropyran,
  4-[3-(7-fluoronaphth-2-ylmethoxy)-5-trifluoromethylphenyl]-4-methoxytetrahydropyran,
  4-allyloxy-4-[3-(7-fluoronaphth-2-ylmethoxy)-5-trifluoromethylphenyl]tetrahydropyran,
  4-[3-(5-bromonaphth-2-ylmethoxy)-5-fluorophenyl]-4-methoxytetrahydropyran,
  (2RS,4SR)-4-[3-(7-fluoronaphth-2-ylmethoxy)phenyl]-4-methoxy-2-methyltetrahydropyran,
  (2RS,4SR)-4-methoxy-2-methyl-4-[3-(7-methylnaphth-2-ylmethoxy)phenyl]tetrahydropyran,
  (2RS,4SR)-4-[3-(7-fluoronaphth-2-ylmethoxy)-5-trifluoromethylphenyl]-4-methoxy-2-methyltetrahydropyran,
  (2RS,4SR)-4-ethoxy-4-[3-(7-fluoronaphth-2-ylmethoxy)-5-trifluoromethylphenyl]-2-methyltetrahydropyran,
  (2RS,4SR)-4-[5-fluoro-3-(7-fluoronaphth-2-ylmethoxy)phenyl]-4-methoxy-2-methyltetrahydropyran,
  (2RS,4SR)-4-ethoxy-4-[5-fluoro-3-(7-fluoronaphth-2-ylmethoxy)phenyl]-2-methyltetrahydropyran,
  (2RS,4SR)-4-allyloxy-4-[3-(7-fluoronaphth-2-ylmethoxy)phenyl]-2-methyltetrahydropyran and
  (2RS,4SR)-4-allyloxy-2-ethyl-4-[3-(naphth-2-ylmethoxy)phenyl]tetrahydropyran. or a pharmaceutically-acceptable salt thereof.

8. A pharmaceutical composition suitable for use in providing inhibition of 5-lipoxygenase which comprises an effective amount of a heterocyclic derivative of the formula I, or a pharamaceutically-acceptable salt thereof, as claimed in any one of claims 1 to 7 in association with a pharmaceutically-acceptable diluent or carrier.

9. A method of treating a disease or medical condition mediated alone or in part by one or more leukotrienes which comprises administering to a warm-blooded animal requiring such treatment a 5-lipoxygenase-inhibitory amount of a heterocyclic derivative of the formula I, or a pharmaceutically-acceptable salt thereof, as claimed in any one of claims 1 to 7.

* * * * *